US007163817B2

(12) United States Patent
Sahni et al.

(10) Patent No.: US 7,163,817 B2
(45) Date of Patent: Jan. 16, 2007

(54) CLOT-SPECIFIC STREPTOKINASE PROTEINS POSSESSING ALTERED PLASMINOGEN ACTIVATION CHARACTERISTICS AND A PROCESS FOR THEIR PREPARATION

(76) Inventors: Girish Sahni, Institute of Microbial Technology, Sector 39A, Union Territory of Chandigarh-160036 (IN); Rajesh Kumar, Institute of Microbial Technology, Sector 39A, Union Territory of Chandigarh-160036 (IN); Chaiti Roy, Institute of Microbial Technology, Sector 39A, Union Territory of Chandigarh-160036 (IN); Kammara Rajagopal, Institute of Microbial Technology, Sector 39A, Union Territory of Chandigarh-160036 (IN); Deepak Nihalani, Institute of Microbial Technology, Sector 39, Union Territory of Chandigarh-160036 (IN); Vasudha Sundaram, Institute of Microbial Technology, Sector 39A, Union Territory of Chandigarh-160036 (IN); Mahavir Yadav, Institute of Microbial Technology, Sector 39A, Union Territory of Chandigarh-160036 (IN)

( * ) Notice: Subject to any disclaimer, the term of this patent is extended or adjusted under 35 U.S.C. 154(b) by 0 days.

(21) Appl. No.: 09/940,235

(22) Filed: Aug. 27, 2001

(65) Prior Publication Data
US 2003/0059921 A1   Mar. 27, 2003

Related U.S. Application Data

(63) Continuation of application No. 09/471,349, filed on Dec. 23, 1999, now abandoned.

(30) Foreign Application Priority Data
Dec. 24, 1998   (IN) .............................. 3825/DEL/98

(51) Int. Cl.
  *C12N 9/48* (2006.01)
  *C12P 21/00* (2006.01)
  *C12P 21/06* (2006.01)
(52) U.S. Cl. .................... 435/212; 435/69.1; 435/69.6; 435/69.7; 435/70.1; 435/71.1
(58) Field of Classification Search ................ 435/216, 435/183
  See application file for complete search history.

(56) References Cited

U.S. PATENT DOCUMENTS 5,026,772 A * 6/1991 Kobayashi et al. ........ 525/54.1
5,151,412 A * 9/1992 Brown ........................... 514/8
5,187,098 A   2/1993 Malke et al. ............. 435/320.1
5,434,073 A * 7/1995 Dawson et al. ............. 435/216
5,772,996 A * 6/1998 Atkinson ................... 424/94.4
6,054,312 A * 4/2000 Larocca et al. .......... 435/320.1

FOREIGN PATENT DOCUMENTS

EP           0 397 366      11/1990
WO        WO 91/17765      11/1991

OTHER PUBLICATIONS

Wishart et al, A single mutation converts a novel phosphotyrosine binding domain into a dual-specificity phosphatase.J Biol Chem. Nov. 10, 1995;270(45):26782-5.*
Witkowski et al, Conversion of a beta-ketoacyl synthase to a malonyl decarboxylase by replacement of the active-site cysteine with glutamine. Biochemistry. Sep. 7, 1999;38(36):11643-50.*
Goldstein et al A chimeric streptokinase with unexpected fibrinolytic selectivity. Thromb Haemost. Sep. 1996;76(3):429-38.*
EMBL database ID No. HSFIBI Jul. 16, 1988 Gronostajski et al.*
U.S. Appl. No. 10/631,588 Sahni et al, filed Jul. 31, 2003. STIC in house alignment of SEQ ID No.: 2 and SEQ ID No.: 11.*
Kornblihtt et al., Primary structure of human fibronectin: differential splicing may generate at least 10 polypeptides from a single gene. EMBO J. Jul. 1985;4(7):1755-9.*
Banerjee et al, Streptokinase—a clinically useful thrombolytic agent.Biotechnol Adv. Feb. 2004:22(4):287-307. Review.*
Jackson et al, Active streptokinase from the cloned gene in *Streptococcus sanguis* is without the carboxy-terminal 32 residues. Biochemistry. Jan. 14, 1986;25(1):108-14.*
Johnson et al, Influence of primary sequence transpositions on the folding pathways of ribonuclease T1.Biochemistry. Aug. 6, 1996;35(31):10223-33.*
Galye et al, Identification of regions in interleukin-1 alpha important for activity.□□J Biol Chem. Oct. 15, 1993;268(29):22105-11.*
Whisstock et al, Prediction of protein function from protein seqeunce and structure.□□Q Rev Biophys. Aug. 2003;36(3):307-40. Review.*
Lucas et al., The binding of human plasminogen to fibrin and fibrinogen. J Biol Chem. Apr. 10, 1983;258(7):4249-56.*
Williams et al., Solution structure of a pair of fibronectin type 1 modules with fibrin binding activity. J Mol Biol. Jan. 28, 1994;235(4):1302-11.*
Huston et al., Protein engineering of antibody binding sites: recovery of specific activity in an anti-digoxin single-chain Fv analogue produced in *Escherichia coli*. Proc Natl Acad Sci U S A. Aug. 1988;85(16):5879-83.*

(Continued)

*Primary Examiner*—Sheridan Swope
(74) *Attorney, Agent, or Firm*—Sughrue Mion, PLLC

(57) ABSTRACT

The invention disclosed herein provides clot specific streptokinase proteins possessing altered plasminogen characteristics, including enhanced fibrin selectivity. The kinetics of plasminogen activation by these proteins are distinct from those of natural streptokinase, in that there is a temporary delay or lag in the initial rate of catalytic conversion of plasminogen to plasmin. Also disclosed are processes for preparing the proteins.

3 Claims, 26 Drawing Sheets

OTHER PUBLICATIONS

Castellino, "Recent Advances in the Chemistry of the Fibrinolytic System", *Chemical Reviews;* vol. 81, No. 5; pp. 431-446 (1981).

Fay et al., "Functional Analysis of the Amino- and Carboxyl-Termini of Streptokinase", *Thromb Haemost;* vol. 79, No. 5; pp. 985-991 (1998).

Fears, "Binding of plasminogen activators to fibrin: characterization and pharmacological consequences", *Biochem. J.;* vol. 261, No. 2; pp. 313-324 (1989).

Hagenson et al., "Expression of streptokinase in *Pichia pastoris* yeast", *Enzyme Microb. Technol.;* vol. 11, No. 10; pp. 650-656 (1989).

Jackson et al., "Complete Amino Acid Sequence of streptokinase and Its Homology with Serine Proteases", *Biochemistry;* vol. 21, No. 25; pp. 6620-6625 (1982).

Kim et al., "C-Terminal Peptide Of Streptokinase, Met369-Pro373, Is Important In Plasminogen Activation", *Biochemistry and Molecular Biology International;* vol. 40, No. 5; pp. 939-945 (1996).

Lee et al., "Identification Of The Functional Importance Of Valine-19 Residue In Streptokinase By N-Terminal Deletion And Site-Directed Mutagenesis", *Biochemistry and Molecular Biology International;* vol. 41, No. 1; pp. 199-207; (1997).

Lin et al., "Mutation of Lysines in a Plasminogen Binding Region of Streptokinase Identifies Residues Important for Generating a Functional Activator Complex", *Biochemistry;* vol. 35, No. 51; pp. 16879-16885 (1996).

Malke et al., "Expression of a streptokinase gene from *Streptococcus equisimilis* in *Streptococcus sanguis*", *Molecular & General Genetics;* vol. 196, No. 1; pp. 360-363 (1984).

Matsuka et al., "The $NH_2$-terminal Fibrin-binding Site of Fibronectin Is Formed by Interacting Fourth and Fifth Finger Domains", *The Journal of Biological Chemistry;* vol. 269, No. 13; pp. 9539-9546 (1994).

Malke et al., "Streptokinase: Cloning, expression, and excretion by *Escherichia coli*", *Proc. Natl. Acad. Sci USA;* vol. 81, No. 10; pp. 3557-3561 (1984).

Nihalani et al., "Mapping of the plasminogen binding site of streptokinase with short synthetic peptides", *Protein Science;* vol. 6, No. 6; pp. 1284-1292 (1997).

Rostagno et al., "Further Characterization of the $NH_2$-terminal Fibrin-binding Site of Fibronectin", *The Journal of Biological Chemistry;* vol. 269, No. 50; pp. 31938-31945 (1994).

Ruoslahti, "Fibronectin and Its Receptors", *Ann. Rev. Biochem.;* vol. 57; pp. 375-413 (1988).

Smith et al., "Fibrinolysis with acyl-ezymes: a new approach to thrombolytic therapy", *Nature;* vol. 290, No. 9; pp. 505-508 (1981).

Verheijen et al., "Involvement of finger domain and kringle 2 domain of tissue-type plasminogen activator in fibrin binding and stimulation of activity by fibrin", *The EMBO Journal;* vol. 5, No. 13; pp. 3525-3530 (1986).

Wong et al., "Engineering and Production of Streptokinase in a *Bacillus subtilis* Expression-Secretion System", *Applied and Environmental Microbiology;* vol. 60, No. 2; pp. 517-523 (1994).

Pilar Alcala, et al., "Engineering of *Escherichia coli* β-galactosidase for solvent display of a Functional scFV Antibody Fragment," *Federation of Europeam Biochemical Societies*, pp. 115-118 (2002).

Sven-Olof Enfors, "Control of in vivo Proteolysis in the Production of Recombinant Proteins," *TibTech,* vol. 10: pp. 310-315 (1992).

CF Ford, et al., Fusion Tails for the Recovery and Purification of Recombinar Proteins, *Protein Expr Purification,* pp. 95-107 (1991).

Richard J. Jenny, et al., "A Critical Review of the Methods for Cleavage of Fusion Proteins with Thrombin and Factor Xa," *Protein Expression and Purification,* vol.: 31 pp. 1-11(2003).

Shannon A. Marshall, et al. "Rational Design and Engineering of Therapeutic Proteins," *Drug Discovery Today,* vol. 8, No. 5 pp. 212-221 (2003).

Didier Picard, "Regulation of Protein Function Through Expression of Chimaeric Proteins," *Current Opinion in Biotechnology,* vol.: 5 p. 511-515 (1994).

Jackson, Kenneth W., et al., "Streptokinase and Staphylokinase," Academic Press vol.; 80 pp. 387-394 (1981).

Kim, Dong Min, et al. "Asp41-His48 Region of Streptokinase Is Important in Binding to a Substrate Plasminogen," *Thrombosis Research* vol. 99 pp. 93-98 (2000).

Lee, Byeong Ryong, et al., "Site-Specific Alteration of GLY-24 in Streptokinase: Its Effect on Plasminogen Activation," *Biochemical and Biophysical Research Communications* vol. 165, No. 3 pp. 1085-1090 (1989).

Malke, Horst, "Polymorphism of the Streptokinase Gene: Implications for the Pathogenesis of Post-Streptococcal Glomerulonephritis," *Gustav Fischer Verlag* vol. 278 pp. 246-257 (1993).

Nihalani, Deepak, et al., "Streptokinase Contains Two Independent Plasminogen-Binding Sites," *Academic Press, Inc.* vol. 217 pp. 1245-1254 (1995).

Potts, Jennifer R., et al., "Solution Structure of the N-Terminal F1 Module Pair from Human Fibronection," *Biochemistry* vol. 38 pp. 8304-8312 (1999).

Reed, Guy L., et al., "Identification of a Plasminogen Binding Region in Streptokinase That Is Necessary for the Creation of a Functional Streptokinase-Plasminogen Activator Complex," *Biochemistry* vol. 34 pp. 10266-10271 (1995).

Saksela Olli, "Radical Caseinolysis in Agarose: A Simple Method for Detection of Plasminogen Activator in the Presence of Inhibitory Substances and Serum," *Biochemistry* pp. 276-282 (1981).

Shi, Suey-Yueh, et al., "Function of Streptokinase Fragments in Plasminogen Activation," *Biochemistry Journal* pp. 235-241 (1994).

Wang, Xiaoqiang, et al., "Crystal Structure of the Catalytic Domain of Human Plasmin Complexed with Streptokinase," *Science Magazine* vol. 281 pp. 1662-1665 (1998).

Welfle, K., et al., "Conformation and Stability of Streptokinases From Nephritogenic and Nonnephritogenic Strains of Streptococci," *Wiley-Liss, Inc.* vol. 27 pp. 26-35 (1997).

Williams, Michael J., et al., "Secondary Structure of a Pair of Fibronectin Type 1 Modules by Two-Dimensional Nuclear Magnetic Resonance," *Biochemistry* vol. 32 pp. 7388-7395 (1993).

Young, Kung-Chia, et al., "Interaction of Streptokinase and Plasminogen," The Journal of Biological Chemistry vol. 270 pp. 29601-29606 (1995).

\* cited by examiner (A) FBD(1,2) fused at the C-terminal of SK

| SK | 1 | 2 |

(B) FBD(4,5) fused at the C-terminal of SK

| SK | 4 | 5 |

(C) FBD(4,5) fused at the N-terminal of SK

| 4 | 5 | SK |

(D) FBD(4,5) fused at both the C as well as N-terminals of SK

| 4 | 5 | SK | 4 | 5 |

FIG. 3-1

```
1/1                                    31/11
ATT GCT GGA CCT GAG TGG CTG CTA GAC CGT CCA TCT GTC AAC AAC AGC CAA TTA GTT GTT
ile ala gly pro glu trp leu leu asp arg pro ser val asn asn ser gln leu val val
61/21                                  91/31
AGC GTT GCT GGT ACT GTT GAG GGG ACG AAT CAA GAC ATT AGT CTT AAA TTT TTT GAA ATC
ser val ala gly thr val glu gly thr asn gln asp ile ser leu lys phe phe glu ile
121/41                                 151/51
GAT CTA ACA TCA CGA CCT GCT CAT GGA GGA AAG ACA GAG CAA GGC TTA AGT CCA AAA TCA
asp leu thr ser arg pro ala his gly gly lys thr glu gln gly leu ser pro lys ser
181/61                                 211/71
AAA CCA TTT GCT ACT GAT AGT GGC GCG ATG TCA CAT AAA CTT GAG AAA GCT GAC TTA CTA
lys pro phe ala thr asp ser gly ala met ser his lys leu glu lys ala asp leu leu
241/81                                 271/91
AAG GCT ATT CAA GAA CAA TTG ATC GCT AAC GTC CAC AGT AAC GAC GAC TAC TTT GAG GTC
lys ala ile gln glu gln leu ile ala asn val his ser asn asp asp tyr phe glu val
301/101                                331/111
ATT GAT TTT GCA AGC GAT GCA ACC ATT ACT GAT CGA AAC GGC AAG GTC TAC TTT GCT GAC
ile asp phe ala ser asp ala thr ile thr asp arg asn gly lys val tyr phe ala asp
361/121                                391/131
AAA GAT GGT TCG GTA ACC TTG CCG ACC CAA CCT GTC CAA GAA TTT TTG CTA AGC GGA CAT
lys asp gly ser val thr leu pro thr gln pro val gln glu phe leu leu ser gly his
421/141                                451/151
GTG CGC GTT AGA CCA TAT AAA GAA AAA CCA ATA CAA AAC CAA GCG AAA TCT GTT GAT GTG
val arg val arg pro tyr lys glu lys pro ile gln asn gln ala lys ser val asp val
481/161                                511/171
GAA TAT ACT GTA CAG TTT ACT CCC TTA AAC CCT GAT GAC GAT TTC AGA CCA GGT CTC AAA
glu tyr thr val gln phe thr pro leu asn pro asp asp asp phe arg pro gly leu lys
541/181                                571/191
GAT ACT AAG CTA TTG AAA ACA CTA GCT ATC GGT GAC ACC ATC ACA TCT CAA GAA TTA CTA
asp thr lys leu leu lys thr leu ala ile gly asp thr ile thr ser gln glu leu leu
601/201                                631/211
GCT CAA GCA CAA AGC ATT TTA AAC AAA AAC CAC CCA GGC TAT ACG ATT TAT GAA CGT GAC
ala gln ala gln ser ile leu asn lys asn his pro gly tyr thr ile tyr glu arg asp
661/221                                691/231
TCC TCA ATC GTC ACT CAT GAC AAT GAC ATT TTC CGT ACG ATT TTA CCA ATG GAT CAA GAG
ser ser ile val thr his asp asn asp ile phe arg thr ile leu pro met asp gln glu
721/241                                751/251
TTT ACT TAC CGT GTT AAA AAT CGG GAA CAA GCT TAT AGG ATC AAT AAA AAA TCT GGT CTG
phe thr tyr arg val lys asn arg glu gln ala tyr arg ile asn lys lys ser gly leu
781/261                                811/271
AAT CAA GAA ATA AAC AAC ACT GAC CTG ATC TCT GAG AAA TAT TAC GTC CTT AAA AAA GGG
asn gln glu ile asn asn thr asp leu ile ser glu lys tyr tyr val leu lys lys gly
841/281                                871/291
GAA AAG CCG TAT GAT CCC TTT GAT CGC AGT CAC TTG AAA CTG TTC ACC ATC AAA TAC GTT
glu lys pro tyr asp pro phe asp arg ser his leu lys leu phe thr ile lys tyr val
901/301                                931/311
GAT GTC GAT ACC AAC GAA TTG CTA AAA AGT GAG CAG CTC TTA ACA GCT AGC GAA CGT AAC
asp val asp thr asn glu leu leu lys ser glu gln leu leu thr ala ser glu arg asn
```

FIG. 3-2

```
961/321                                     991/331
TTA GAC TTC AGA GAT TTA TAC GAT CCT CGT GAT AAG GCT AAA CTA CTC TAC AAC AAT CTC
leu asp phe arg asp leu tyr asp pro arg asp lys ala lys leu leu tyr asn asn leu
1021/341                                    1051/351
GAT GCT TTT GGT ATT ATG GAC TAT ACC TTA ACT GGA AAA GTA GAG GAT AAT CAC GAT GAC
asp ala phe gly ile met asp tyr thr leu thr gly lys val glu asp asn his asp asp
1081/361                                    1111/371
ACC AAC CGT ATC ATA ACC GTT TAT ATG GGC AAG CGA CCC GAA GGA GAG AAT GCT AGC TAT
thr asn arg ile ile thr val tyr met gly lys arg pro glu gly glu asn ala ser tyr
1141/381                                    1171/391
CAT TTA GCC TAT GAT AAA GAT CGT TAT ACC GAA GAA GAA CGA GAA GTT TAC AGC TAC CTG
his leu ala tyr asp lys asp arg tyr thr glu glu glu arg glu val tyr ser tyr leu
1201/401                                    1231/411
CGT TAT ACA GGG ACA CCT ATA CCT GAT AAC CCT AAC GAC AAA TAA
arg tyr thr gly thr pro ile pro asp asn pro asn asp lys OCH
```

FIG. 6

```
1/1                                           31/11
CAG GCT CAG CAA ATG GTT CAG CCC CAG TCC  CCG GTG GCT GTC ACT CAA AGC AAG CCC GGT
gln ala gln gln met val gln pro gln ser  pro val ala val ser gln ser lys pro gly
61/21                                         91/31
TGT TAT GAC AAT GGA AAA CAC TAT CAG ATA  AAT CAA CAG TGG GAG CGG ACC TAC CTA GGT
cys tyr asp asn gly lys his tyr gln ile  asn gln gln trp glu arg thr tyr leu gly
121/41                                        151/51
AAT GTG TTG GTT TGT ACT TGT TAT GGA GGA  AGC CGA GGT TTT AAC TGC GAA AGT AAA CCT
asn val leu val cys thr cys tyr gly gly  ser arg gly phe asn cys glu ser lys pro
181/61                                        211/71
GAA GCT GAA GAG ACT TGC TTT GAC AAG TAC  ACT GGG AAC ACT TAC CGA GTG GGT GAC ACT
glu ala glu glu thr cys phe asp lys tyr  thr gly asn thr tyr arg val gly asp thr
241/81                                        271/91
TAT GAG CGT CCT AAA GAC TCC ATG ATC TGG  GAC TGT ACC TGC ATC GGG GCT GGG CGA GGG
tyr glu arg pro lys asp ser met ile trp  asp cys thr cys ile gly ala gly arg gly
301/101                                       331/111
AGA ATA AGC TGT ACC ATC GCA AAC CGC TGC  CAT GAA GGG GGT CAG TCC TAC AAG ATT GGT
arg ile ser cys thr ile ala asn arg cys  his glu gly gly gln ser tyr lys ile gly
361/121                                       391/131
GAC ACC TGG AGG AGA CCA CAT GAG ACT GGT  GGT TAC ATG TTA GAG TGT GTG TGT CTT GGT
asp thr trp arg arg pro his glu thr gly  gly tyr met leu glu cys val cys leu gly
421/141                                       451/151
AAT GGA AAA GGA GAA TGG ACC TGC AAG CCC  ATA GCT GAG AAG TGT TTT GAT CAT GCT GCT
asn gly lys gly glu trp thr cys lys pro  ile ala glu lys cys phe asp his ala ala
481/161                                       511/171
GGG ACT TCC TAT GTG GTC GGA GAA ACG TGG  GAG AAG CCC TAC CAA GGC TGG ATG ATG GTA
gly thr ser tyr val val gly glu thr trp  glu lys pro tyr gln gly trp met met val
541/181                                       571/191
GAT TGT ACT TGC CTG GGA GAA GGC AGC GGA  CGC ATC ACT TGC ACT TCT AGA AAT AGA TGC
asp cys thr cys leu gly glu gly ser gly  arg ile thr cys thr ser arg asn arg cys
601/201                                       631/211
AAC GAT CAG GAC ACA AGG ACA TCC TAT AGA  ATT GGA GAC ACC TGG AGC AAG AAG GAT AAT
asn asp gln asp thr arg thr ser tyr arg  ile gly asp thr trp ser lys lys asp asn
661/221                                       691/231
CGA GGA AAC CTG CTC CAG TGC ATC TGC ACA  GGC AAC GGC CGA GGA GAG TGG AAG TGT GAG
arg gly asn leu leu gln cys ile cys thr  gly asn gly arg gly glu trp lys cys glu
721/241                                       751/251
AGG CAC ACC TCT GTG CAG ACC ACA TCG AGC  GGA TCT GGC CCC TTC ACC GAT GTT CGT
arg his thr ser val gln thr thr ser ser  gly ser gly pro phe thr asp val arg
```

FIG. 11

```
              10         20         30         40         50
         GCACCCGTGG CCAGGACCCA ACGCTGCCCG AGATCTCGAT CCCGCGAAAT
   51    TAATACGACT CACTATAGGG AGACCACAAC GGTTTCCCTC TAGAAATAAT
  101    TTTGTTTAAC TTTAAGAAGG AGATATACCA TGATTGCTGG ACCTGAGTGG
  151    CTGCTAGACC GTCCATCTGT CAACAACAGC CAATTGGTTG TTAGCGTTGC
  201    TGGTACTGTT GAGGGGACGA ATCAAGACAT TAGTCTTAAA TTTTTTGAAA
  251    TCGATCTAAC ATCACGACCT GCTCATGGAG GAAAGACAGA GCAAGGCTTA
  301    AGTCCAAAAT CAAAACCATT TGCTACTGAT AGTGGCGCGA TGTCACATAA
  351    ACTTGAGAAA GCTGACTTAC TAAAGGCTAT TCAAGAACAA TTGATCGCTA
  401    ACGTCCACAG TAACGACGAC TACTTTGAGG TCATTGATTT TGCAAGCGAT
  451    GCAACCATTA CTGATCGAAA CGGCAAGGTC TACTTTGCTG ACAAAGATGG
  501    TTCGGTAACC TTGCCGACCC AACCTGTCCA AGAATTTTTG CTAAGCGGAC
  551    ATGTGCGCGT TAGACCATAT AAAGAAAAAC CAATACAAAA CCAAGCAAA
  601    TCTGTTGATG TGGAATATAC TGTACAGTTT ACTCCCTTAA ACCCTGATGA
  651    CGATTTCAGA CCAGGTCTCA AAGATACTAA GCTATTGAAA ACACTAGCTA
  701    TCGGTGACAC CATCACATCT CAAGAATTAC TAGCTCAAGC ACAAAGCATT
  751    TTAAACAAAA ACCACCCAGG CTATACGATT TATGAACGTG ACTCCTCAAT
  801    CGTCACTCAT GACAATGACA TTTTCCGTAC GATTTTACCA ATGGATCAAG
  851    AGTTTACTTA CCGTGTTAAA AATCGGGAAC AAGCTTATAG GATCAATAAA
  901    AAATCTGGTC TGAATGAAGA AATAAACAAC ACTGACCTGA TCTCTGAGAA
  951    ATATTACGTC CTTAAAAAAG GGGAAAAGCC GTATGATCCC TTTGATCGCA
 1001    GTCACTTGAA ACTGTTCACC ATCAAATACG TTGATGTCGA TACCAACGAA
 1051    TTGCTAAAAA GTGAGCAGCT CTTAACAGCT AGCGAACGTA ACTTAGACTT
 1101    CAGAGATTTA TACGATCCTC GTGATAAGGC TAAACTACTC TACAACAATC
 1151    TCGATGCTTT TGGTATTATG GACTATACCT TAACTGGAAA AGTAGAGGAT
 1201    AATCACGATG ACACCAACCG TATCATAACC GTTTATATGG GCAAGCGACC
 1251    CGAAGGAGAG AATGCTAGCT ATCATTTAGC CTATGATAAA GATCGTTATA
 1301    CCGAAGAAGA ACGAGAAGTT TACAGCTACC TGCGTTATAC AGGGACACCT
 1351    ATACCTGATA ACCCTAACGA CAAATAA
```

ΔG=−10.3Kcal/mol

ΔG=−5.0Kcal/mol

FIG. 14

```
             10         20         30         40         50
        TAATACGACT CACTATAGGG AGACCACAAC GGTTTCCCTC TAGAAATAAT
  51    TTTGTTTAAC TTTAAGAAGG AGATATACCA TGATAGCTGG TCCTGAATGG
 101    CTACTAGATC GTCCTTCTGT AAATAACAGC CAATTGGTTG TTAGCGTTGC
 151    TGGTACTGTT GAGGGGACGA ATCAAGACAT TAGTCTTAAA TTTTTTGAAA
 201    TCGATCTAAC ATCACGACCT GCTCATGGAG GAAAGACAGA GCAAGGCTTA
 251    AGTCCAAAAT CAAAACCATT TGCTACTGAT AGTGGCGCGA TGTCACATAA
 301    ACTTGAGAAA GCTGACTTAC TAAAGGCTAT TCAAGAACAA TTGATCGCTA
 351    ACGTCCACAG TAACGACGAC TACTTTGAGG TCATTGATTT TGCAAGCGAT
 401    GCAACCATTA CTGATCGAAA CGGCAAGGTC TACTTTGCTG ACAAAGATGG
 451    TTCGGTAACC TTGCCGACCC AACCTGTCCA AGAATTTTTG CTAAGCGGAC
 501    ATGTGCGCGT TAGACCATAT AAAGAAAAAC CAATACAAAA CCAAGCGAAA
 551    TCTGTTGATG TGGAATATAC TGTACAGTTT ACTCCCTTAA ACCCTGATGA
 601    CGATTTCAGA CCAGGTCTCA AAGATACTAA GCTATTGAAA ACACTAGCTA
 651    TCGGTGACAC CATCACATCT CAAGAATTAC TAGCTCAAGC ACAAAGCATT
 701    TTAAACAAAA ACCACCCAGG CTATACGATT TATGAACGTG ACTCCTCAAT
 751    CGTCACTCAT GACAATGACA TTTTCCGTAC GATTTTACCA ATGGATCAAG
 801    AGTTTACTTA CCGTGTTAAA AATCGGGAAC AAGCTTATAG GATCAATAAA
 851    AAATCTGGTC TGAATGAAGA AATAAACAAC ACTGACCTGA TCTCTGAGAA
 901    ATATTACGTC CTTAAAAAAG GGGAAAAGCC GTATGATCCC TTTGATCGCA
 951    GTCACTTGAA ACTGTTCACC ATCAAATACG TTGATGTCGA TACCAACGAA
1001    TTGCTAAAAA GTGAGCAGCT CTTAACAGCT AGCGAACGTA ACTTAGACTT
1051    CAGAGATTTA TACGATCCTC GTGATAAGGC TAAACTACTC TACAACAATC
1101    TCGATGCTTT TGGTATTATG GACTATACCT TAACTGGAAA AGTAGAGGAT
1151    AATCACGATG ACACCAACCG TATCATAACC GTTTATATGG GCAAGCGACC
1201    CGAAGGAGAG AATGCTAGCT ATCATTTAGC CTATGATAAA GATCGTTATA
1251    CCGAAGAAGA ACGAGAAGTT TACAGCTACC TGCGTTATAC AGGGACACCT
1301    ATACCTGATA ACCCTAACGA CAAATAA
```

FIG. 17B

```
              10         20         30         40         50
        TTTGTTTAAC TTTAAGAAGG AGATATACCA TGATAGCTGG TCCTGAATGG
   51   CTACTAGATC GTCCTTCTGT AAATAACAGC CAATTGGTTG TTAGCGTTGC
  101   TGGTACTGTT GAGGGGACGA ATCAAGACAT TAGTCTTAAA TTTTTTGAAA
  151   TCGATCTAAC ATCACGACCT GCTCATGGAG GAAAGACAGA GCAAGGCTTA
  201   AGTCCAAAAT CAAAACCATT TGCTACTGAT AGTGGCGCGA TGTCACATAA
  251   ACTTGAGAAA GCTGACTTAC TAAAGGCTAT TCAAGAACAA TTGATCGCTA
  301   ACGTCCACAG TAACGACGAC TACTTTGAGG TCATTGATTT TGCAAGCGAT
  351   GCAACCATTA CTGATCGAAA CGGCAAGGTC TACTTTGCTG ACAAAGATGG
  401   TTCGGTAACC TTGCCGACCC AACCTGTCCA AGAATTTTTG CTAAGCGGAC
  451   ATGTGCGCGT TAGACCATAT AAAGAAAAAC CAATACAAAA CCAAGCGAAA
  501   TCTGTTGATG TGGAATATAC TGTACAGTTT ACTCCCTTAA ACCCTGATGA
  551   CGATTTCAGA CCAGGTCTCA AAGATACTAA GCTATTGAAA ACACTAGCTA
  601   TCGGTGACAC CATCACATCT CAAGAATTAC TAGCTCAAGC ACAAAGCATT
  651   TTAAACAAAA ACCACCCAGG CTATACGATT TATGAACGTG ACTCCTCAAT
  701   CGTCACTCAT GACAATGACA TTTTCCGTAC GATTTTACCA ATGGATCAAG
  751   AGTTTACTTA CCGTGTTAAA AATCGGGAAC AAGCTTATAG GATCAATAAA
  801   AAATCTGGTC TGAATGAAGA AATAAACAAC ACTGACCTGA TCTCTGAGAA
  851   ATATTACGTC CTTAAAAAAG GGGAAAAGCC GTATGATCCC TTTGATCGCA
  901   GTCACTTGAA ACTGTTCACC ATCAAATACG TTGATGTCGA TACCAACGAA
  951   TTGCTAAAAA GTGAGCAGCT CTTAACAGCT AGCGAACGTA ACTTAGACTT
 1001   CAGAGATTTA TACGATCCTC GTGATAAGGC TAAACTACTC TACAACAATC
 1051   TCGATGCTTT TGGTATTATG GACTATACCT TAACTGGAAA AGTAGAGGAT
 1101   AATCACGATG ACACCAACCG TATCATAACC GTTTATATGG GCAAGCGACC
 1151   CGAAGGAGAG AATGCTAGCT ACCATTTAGC TGGTGGTGGC CAGGCGCAAC
 1201   AGATTGTACC CATAGCTGAG AAGTGTTTTG ATCATGCTGC TGGGACTTCC
 1251   TATGTGGTCG GAGAAACGTG GGAGAAGCCC TACCAAGGCT GGATGATGGT
 1301   AGATTGTACT TGCCTGGGAG AAGGCAGCGG ACGCATCACT TGCACTTCTA
 1351   GAAATAGATG CAACGATCAG GACACAAGGA CATCCTATAG AATTGGAGAC
 1401   ACCTGGAGCA AGAAGGATAA TCGAGGAAAC CTGCTCCAGT GCATCTGCAC
 1451   AGGCAACGGC CGAGGAGAGT GGAAGTGTGA GAGGCACACC TCTGTGCAGA
 1501   CCACATCGAG CGGATCTGGC CCCTTCACCG ATGTTCGTTA G
```

FIG. 19B

```
             10         20         30         40         50
        GCAACCCCGC CAGCCTAGCC GGGTCCTCAA CGACAGGAGC ACGATCATGC
  51    GCACCCGTGG CCAGGACCCA ACGCTGCCCG AGATCTCGAT CCCGCGAAAT
 101    TAATACGACT CACTATAGGG AGACCACAAC GGTTTCCCTC TAGAAATAAT
 151    TTTGTTTAAC TTTAAGAAGG AGATATACCA TGATTGCTGG ACCTGAGTGG
 201    CTGCTAGACC GTCCATCTGT CAACAACAGC CAATTGGTTG TTAGCGTTGC
 251    TGGTACTGTT GAGGGGACGA ATCAAGACAT TAGTCTTAAA TTTTTTGAAA
 301    TCGATCTAAC ATCACGACCT GCTCATGGAG GAAAGACAGA GCAAGGCTTA
 351    AGTCCAAAAT CAAAACCATT TGCTACTGAT AGTGGCGCGA TGTCACATAA
 401    ACTTGAGAAA GCTGACTTAC TAAAGGCTAT TCAAGAACAA TTGATCGCTA
 451    ACGTCCACAG TAACGACGAC TACTTTGAGG TCATTGATTT TGCAAGCGAT
 501    GCAACCATTA CTGATCGAAA CGGCAAGGTC TACTTTGCTG ACAAAGATGG
 551    TTCGGTAACC TTGCCGACCC AACCTGTCCA AGAATTTTTG CTAAGCGGAC
 601    ATGTGCGCGT TAGACCATAT AAAGAAAAAC CAATACAAAA CCAAGCGAAA
 651    TCTGTTGATG TGGAATATAC TGTACAGTTT ACTCCCTTAA ACCCTGATGA
 701    CGATTTCAGA CCAGGTCTCA AAGATACTAA GCTATTGAAA ACACTAGCTA
 751    TCGGTGACAC CATCACATCT CAAGAATTAC TAGCTCAAGC ACAAAGCATT
 801    TTAAACAAAA ACCACCCAGG CTATACGATT TATGAACGTG ACTCCTCAAT
 851    CGTCACTCAT GACAATGACA TTTTCCGTAC GATTTTACCA ATGGATCAAG
 901    AGTTTACTTA CCGTGTTAAA AATCGGGAAC AAGCTTATAG GATCAATAAA
 951    AAATCTGGTC TGAATGAAGA AATAAACAAC ACTGACCTGA TCTCTGAGAA
1001    ATATTACGTC CTTAAAAAAG GGGAAAAGCC GTATGATCCC TTTGATCGCA
1051    GTCACTTGAA ACTGTTCACC ATCAAATACG TTGATGTCGA TACCAACGAA
1101    TTGCTAAAAA GTGAGCAGCT CTTAACAGCT AGCGAACGTA ACTTAGACTT
1151    CAGAGATTTA TACGATCCTC GTGATAAGGC TAAACTACTC TACAACAATC
1201    TCGATGCTTT TGGTATTATG GACTATACCT TAACTGGAAA AGTAGAGGAT
1251    AATCACGATG ACACCAACCG TATCATAACC GTTTATATGG GCAAGCGACC
1301    CGAAGGAGAG AATGCTAGCT ATCATTTAGC CGGTGGTGGT CAGGCGCAGC
1351    AAATGGTTCA GCCCCAGTCC CCGGTGGCTG TCAGTCAAAG CAAGCCCGGT
1401    TGTTATGACA ATGGAAAACA CTATCAGATA AATCAACAGT GGGAGCGGAC
1451    CTACCTAGGT AATGTGTTGG TTTGTACTTG TTATGGAGGA AGCCGAGGTT
1501    TTAACTGCGA AAGTAAACCT GAAGCTGAAG AGACTTGCTT TGACAAGTAC
1551    ACTGGGAACA CTTACCGAGT GGGTGACACT TATGAGCGTC CTAAAGACTC
1601    CATGATCTGG GACTGTACCT GCATCGGGGC TGGGCGAGGG AGAATAAGCT
1651    GTACCATCTA A
```

FIG. 21B

```
              10         20         30         40         50
   1  TCGCTTCACG TTCGCTCGCG TATCGGTGAT TCATTCTGCT AACCAGTAAG
  51  GCAACCCCGC CAGCCTAGCC GGGTCCTCAA CGACAGGAGC ACGATCATGC
 101  GCACCCGTGG CCAGGACCCA ACGCTGCCCG AGATCTCGAT CCCGCGAAAT
 151  TAATACGACT CACTATAGGG AGACCACAAC GGTTTCCCTC TAGAAATAAT
 201  TTTGTTTAAC TTTAAGAAGG AGATATACCA TGGTGCAAGC ACAACAGATT
 251  GTACCCATAG CTGAGAAGTG TTTTGATCAT GCTGCTGGGA CTTCCTATGT
 301  GGTCGGAGAA ACGTGGGAGA AGGCAGCGGA CGCATCACTT GCACTTCTAG
 351  AAATAGATGC AACGATCAGG ACACAAGGAC ATCCTATAGA ATTGGAGACA
 401  CCTGGAGCAA GAAGGATAAT CGAGGAAACC TGCTCCAGTG CATCTGCACA
 451  GGCAACGGCC GAGGAGAGTG GAAGTGTGAG AGGCACACCT CTGTGCAGAC
 501  CACATCGAGC GGATCTGGCC CCTTCACCGA TGTTCGTATT GCTGGACCTG
 551  AGTGGCTGCT AGACCGTCCA TCTGTCAACA ACAGCCAATT GGTTGTTAGC
 601  GTTGCTGGTA CTGTTGAGGG GACGAATCAA GACATTAGTC TTAAATTTTT
 651  TGAAATCGAT CTAACATCAC GACCTGCTCA TGGAGGAAAG ACAGAGCAAG
 701  GCTTAAGTCC AAAATCAAAA CCATTTGCTA CTGATAGTGG CGCGATGTCA
 751  CATAAACTTG AGAAAGCTGA CTTACTAAAG GCTATTCAAG AACAATTGAT
 801  CGCTAACGTC CACAGTAACG ACGACTACTT TGAGGTCATT GATTTTGCAA
 851  GCGATGCAAC CATTACTGAT CGAAACGGCA AGGTCTACTT TGCTGACAAA
 901  GATGGTTCGG TAACCTTGCC GACCCAACCT GTCCAAGAAT TTTTGCTAAG
 951  CGGACATGTG CGCGTTAGAC CATATAAAGA AAAACCAATA CAAAACCAAG
1001  CGAAATCTGT TGATGTGGAA TATACTGTAC AGTTTACTCC CTTAAACCCT
1051  GATGACGATT TCAGACCAGG TCTCAAAGAT ACTAAGCTAT TGAAAACACT
1101  AGCTATCGGT GACACCATCA CATCTCAAGA ATTACTAGCT CAAGCACAAA
1151  GCATTTTAAA CAAAAACCAC CCAGGCTATA CGATTTATGA ACGTGACTCC
1201  TCAATCGTCA CTCATGACAA TGACATTTTC CGTACGATTT TACCAATGGA
1251  TCAAGAGTTT ACTTACCGTG TTAAAAATCG GGAACAAGCT TATAGGATCA
1301  ATAAAAAATC TGGTCTGAAT GAAGAAATAA ACAACACTGA CCTGATCTCT
1351  GAGAAATATT ACGTCCTTAA AAAAGGGGAA AAGCCGTATG ATCCCTTTGA
1401  TCGCAGTCAC TTGAAACTGT TCACCATCAA ATACGTTGAT GTCGATACCA
1451  ACGAATTGCT AAAAAGTGAG CAGCTCTTAA CAGCTAGCGA ACGTAACTTA
1501  GACTTCAGAG ATTTATACGA TCCTCGTGAT AAGGCTAAAC TACTCTACAA
1551  CAATCTCGAT GCTTTTGGTA TTATGGACTA TACCTTAACT GGAAAAGTAG
1601  AGGATAATCA CGATGACACC AACCGTATCA TAACCGTTTA TATGGGCAAG
1651  CGACCCGAAG GAGAGAATGC TAGCTATCAT TTAGCCTATG ATAAAGATCG
1701  TTATACCGAA GAAGAACGAG AAGTTTACAG CTACCTGCGT TATACAGGGA
1751  CACCTATACC TGATAACCCT AACGACAAAT AA
```

FIG. 22B

```
              10         20         30         40         50
   1    CGAAGACCAT TCATGTTGTT GCTCAGGTCG CAGACGTTTT GCAGCAGCAG
  51    TCGCTTCACG TTCGCTCGCG TATCGGTGAT TCATTCTGCT AACCAGTAAG
 101    GCAACCCCGC CAGCCTAGCC GGGTCCTCAA CGACAGGAGC ACGATCATGC
 151    GCACCCGTGG CCAGGACCCA ACGCTGCCCG AGATCTCGAT CCCGCGAAAT
 201    TAATACGACT CACTATAGGG AGACCACAAC GGTTTCCCTC TAGAAATAAT
 251    TTTGTTTAAC TTTAAGAAGG AGATATACCA TGGTGCAAGC ACAACAGATT
 301    GTACCCATAG CTGAGAAGTG TTTTGATCAT GCTGCTGGGA CTTCCTATGT
 351    GGTCGGAGAA ACGTGGGAGA AGGCAGCGGA CGCATCACTT GCACTTCTAG
 401    AAATAGATGC AACGATCAGG ACACAAGGAC ATTCCTATAGA ATTGGAGACA
 451    CCTGGAGCAA GAAGGATAAT CGAGGAAACC TGCTCCAGTG CATCTGCACA
 501    GGCAACGGCC GAGGAGAGTG GAAGTGTGAG AGGCACACCT CTGTGCAGAC
 551    CACATCGAGC GGATCTGGCC CCTTCACCGA TGTTCGTATT GCTGGACCTG
 601    AGTGGCTGCT AGACCGTCCA TCTGTCAACA ACAGCCAATT GGTTGTTAGC
 651    GTTGCTGGTA CTGTTGAGGG GACGAATCAA GACATTAGTC TTAAATTTTT
 701    TGAAATCGAT CTAACATCAC GACCTGCTCA TGGAGGAAAG ACAGAGCAAG
 751    GCTTAAGTCC AAAATCAAAA CCATTTGCTA CTGATAGTGG CGCGATGTCA
 801    CATAAACTTG AGAAAGCTGA CTTACTAAAG GCTATTCAAG AACAATTGAT
 851    CGCTAACGTC CACAGTAACG ACGACTACTT TGAGGTCATT GATTTTGCAA
 901    GCGATGCAAC CATTACTGAT CGAAACGGCA AGGTCTACTT TGCTGACAAA
 951    GATGGTTCGG TAACCTTGCC GACCCAACCT GTCCAAGAAT TTTTGCTAAG
1001    CGGACATGTG CGCGTTAGAC CATATAAAGA AAAACCAATA CAAAACCAAG
1051    CGAAATCTGT TGATGTGGAA TATACTGTAC AGTTTACTCC CTTAAACCCT
1101    GATGACGATT TCAGACCAGG TCTCAAAGAT ACTAAGCTAT TGAAAACACT
1151    AGCTATCGGT GACACCATCA CATCTCAAGA ATTACTAGCT CAAGCACAAA
1201    GCATTTTAAA CAAAAACCAC CCAGGCTATA CGATTTATGA ACGTGACTCC
1251    TCAATCGTCA CTCATGACAA TGACATTTTC CGTACGATTT TACCAATGGA
1301    TCAAGAGTTT ACTTACCGTG TTAAAAATCG GGAACAAGCT TATAGGATCA
1351    ATAAAAAATC TGGTCTGAAT GAAGAAATAA ACAACACTGA CCTGATCTCT
1401    GAGAAATATT ACGTCCTTAA AAAAGGGGAA AAGCCGTATG ATCCCTTTGA
1451    TCGCAGTCAC TTGAAACTGT TCACCATCAA ATACGTTGAT GTCGATACCA
1501    ACGAATTGCT AAAAAGTGAG CAGCTCTTAA CAGCTAGCGA ACGTAACTTA
1551    GACTTCAGAG ATTTATACGA TCCTCGTGAT AAGGCTAAAC TACTCTACAA
1601    CAATCTCGAT GCTTTTGGTA TTATGGACTA TACCTTAACT GGAAAAGTAG
1651    AGGATAATCA CGATGACACC AACCGTATCA TAACCGTTTA TATGGGCAAG
1701    CGACCCGAAG GAGAGAATGC TAGCTACCAT TTAGCTGGTG GTGGCCAGGC
1751    GCAACAGATT GTACCCATAG CTGAGAAGTG TTTTGATCAT GCTGCTGGGA
1801    CTTCCTATGT GGTCGGAGAA ACGTGGGAGA AGCCCTACCA AGCCTGGATG
1851    ATGGTAGATT GTACTTGCCT GGGAGAAGGC AGCGGACGCA TCACTTGCAC
1901    TTCTAGAAAT AGATGCAACG ATCAGGACAC AAGGACATCC TATAGAATTG
1951    GAGACACCTG GAGCAAGAAG GATAATCGAG GAAACCTGCT CCAGTGCATC
2001    TGCACAGGCA ACGGCCGAGG AGAGTGGAAG TGTGAGAGGC ACACCTCTGT
2051    GCAGACCACA TCGAGCGGAT CTGGCCCCTT CACCGATGTT CGTTAG
```

CLOT-SPECIFIC STREPTOKINASE PROTEINS POSSESSING ALTERED PLASMINOGEN ACTIVATION CHARACTERISTICS AND A PROCESS FOR THEIR PREPARATION

This application is a continuation of application Ser. No. 09/471,349, filed Dec. 23, 1999, which is abandoned.

FIELD

The present invention relates to novel clot specific streptokinase proteins possessing altered plasminogen characteristics. The invention further relates to a process for the preparation of the said proteins. The streptokinases so produced have properties of enhanced fibrin selectivity as well as kinetics of plasminogen activation that are distinct from that of natural streptokinase in being characterized by a temporary delay, or lag, of several minutes in the initial rate of the catalytic conversion of plasminogen to plasmin (a process termed hereafter as "PG activation").

The advantage of this invention lies in the presence of these two properties in these chimeric (or hybrid) proteins together i.e. fibrin affinity and an initial lag in plasminogen activation. In other words, the hybrid protein molecules disclosed in this invention are both fibrin specific and display "delayed-action" thrombolysis. This confers on these novel proteins the ability to bind tightly with fibrin, the proteinaceous substance of blood clots soon after their introduction into the vascular system without significantly activating the circulating blood plasminogen to plasmin, thus aiding in the localization of the PG activation process to the site of the pathological thrombus. Thus, once the PG activation lag is overcome within a few minutes' of the exposure of the hybrid proteins to plasminogen, they can easily activate the plasminogen in the immediate vicinity of the thrombus in a manner essentially similar to that of natural i.e. unmodified streptokinase, thereby obviating the systemic PG activation frequently encountered during clinical use of streptokinases. These new hybrid proteins can therefore be used to advantage for thrombolytic therapy for various kinds of cardiovascular disorders.

BACKGROUND

In recent years, thrombolytic therapy with fibrinolytic agents, such as Streptokinase (SK), tissue plasminogen activator (TPA) or urokinase (UK) has revolutionized the clinical management of diverse circulatory diseases e.g., deep-vein thrombosis, pulmonary embolism and myocardial infarction. These agents exert their fibrinolytic effects through activation of plasminogen (PG) in the circulation by cleavage of the scissile peptide bond between residues 561 and 562 in PG. As a result, inactive zymogen is transformed to its active form, the serine protease, plasmin (PN), which then acts on fibrin to degrade the latter into soluble degradation products. It may be mentioned here that PN, by itself, is incapable of activating PG to PN; this reaction is catalyzed by highly specific proteases like TPA, the SK-plasminogen complex, and UK, all of which possess an unusually narrow protein substrate preference, namely a propensity to cleave the scissile peptide bond in PG. However, unlike UK and TPA, SK has no proteolytic activity of its own, and it activates PG to PN indirectly by first forming a high-affinity equimolar complex with PG, known as the activator complex (reviewed in Castellino, F. J., 1981, *Chem Rev.* 81: 431).

Of the several thrombolytic agents used clinically, SK is probably one of the most-often employed, particularly because of its markedly lower cost when coded to TPA and UK. However, the choice of thrombolytic agent during therapy is dictated by a number of factors besides costs, such as the presence of side-effects and their severity, in vivo metabolic survival of the drug (e.g., circulatory clearance rates), fibrin selectivity and/or affinity, immunological reactivity etc. SK is a highly potent PG activator, and has a relatively long plasma half-life—properties that, together, impart a certain advantage to this drug as compared to its counterparts viz, TPA and UK. However, due to a lack of any appreciable fibrin clot-specificity in the former, the administration of therapeutically effective doses of SK often results in systemic PG activation, resulting in hemorrhagic complications due to the proteolytic degradation of blood factors by the plasmin generated throughout the circulatory system. However, if a fibrin affinity and/or selectivity could be integrated into SK, a molecule which otherwise possesses little fibrin affinity of its own, it would considerably enhance the therapeutic efficacy of this thrombolytic agent. With respect to the other coveted trait in a fibrinolytic agent, such as that described above for TPA above (viz., considerably lowered activity while circulating in the vascular system but enhanced PG activating ability in the presence of fibrin), attempts have been made in the past to produce analogs of SK with greater circulatory half-lives and decreased systemic plasmin generation by incorporating properties such as a slower rate of PG activation into the fibrinolytic agent. One example where this has been successfully accomplished is that of anisoylated streptokinase plasmin activator complex, abbreviated APSAC (sold under the trade-name 'Eminase' by the Beecham pharmaceutical group) (reference: Smith, R. A. G., Dupe, R. J., English P. D., and Green, J., 1981, *Nature* 290:505) in which the catalytically important serine residue of the plasmin component is blocked by reversible acylation. The generalized plasmin activation coincident with the administration of unmodified SK has been reported to be appreciably diminished during thrombolytic therapy with APSAC since the deacylation of the covalently modified serine in the SK-acylated plasmin complex occurs slowly in the vascular systems.

It is thus generally recognized that it will be of significant clinical advantage if SK could be engineered to possess increased fibrin affinity/specificity together with a markedly slower initial rate of activation of PG. Thus, soon after injection into the body, whilst it is still in an inactive or partially active state, such a modified PG activator will bind to the pathological fibrin clot during its initial sojourn through the vascular system in an inactive/partially active state. However, after an initial lag (a property engineered into the derivative/analog through design) it will become fully activated after being sequestered to the fibrin clot by virtue of its fibrin affinity. Thus, the PG activation process will be relatively limited to the immediate vicinity of the clot, thus obviating the systemic PG activation coincident with natural SK administration which has no intrinsic fibrin affinity of its own and which activates PG as soon as it encounters it. In other words, whilst the former property in the novel protein/s would be expected to confer on the thrombolytic agent an ability to target itself to the immediate locale of the pathological clot and thus help build up therapeutically effective concentrations of the activator therein, the initially slow kinetics of PG activation would result in an overall diminished generation of free plasmin in the circulation. The net result shall be a continued and more efficient fibrinolysis at the target sustained by considerably lowered therapeutically effective dosages of the thrombolytic agent.

In the past, the gene encoding for SK has been isolated from its natural source (*Streptococcus* species) and cloned into several heterologous micro-organisms such as yeast (Hagenson, M. J., Holden, K. A., Parker, K. A., Wood, P. J., Cruze, J. A., Fuke. M., Hopkins, T. R., Stroman D. W., 1989, *Enzyme. Microb. Technol.* 11:650), bacteria viz., *E. coli* (Malke, H, Ferretti, J. J., 1984, *Proc. Nat'l Acad. Sci.* 81: 3557), alternate species of *Streptococcus* (Malke, H., Gerlach, D., Kohler, W., Ferretti, J. J., 1984, *Mol. Gen. Genet.* 196:360), and *Bacillus* (Wong, S. L., Ye, R., Nathoo S., 1994, *Applied and Env. Microbiol* 1:517). In addition, genetically modified SK derivatives containing "Kringle" type fibrin binding domains derived from plasminogen, and methods of obtaining the same by rDNA techniques, have been described (EU 0397 366 A1). However, since five such Kringle regions are already present in the natural SK-PG activator complex, being an integral part of PG in the activator complex, the advantages gained from further addition of such domains are likely to be minimal. Hence, there is a need to impart a qualitatively different fibrin-affinity and/or specificity to the activator complex. particularly a type associated with TPA, a very effective thrombolytic agent possessing much greater fibrin affinity than SK. TPA is known to contain a fibrin-associating "finger" domain, which is structurally and functionally very similar to the fibrin-binding domains present in fibronectin, a multi-functional protein with ability to interact with a number of other proteins besides fibrin e.g., collagen, heparin, actin etc (reviewed in Ruoslahti, E., 1988, *Ann. Rev. Biochem.* 57:375). Methods for the imaging of fibrin-containing substances, such as pathological clots and/or atherosclerotic plaques in vivo by using large radio-labeled polypeptides derived from fibronectin, and bearing these FBDs (fibrin binding domains) have been disclosed (see: PCT WO 91/17765); this patent also discloses chemically cross-linked FBD-containing polypeptides and a thrombolytic agent (SK) to effect thrombus-targeted fibrinolysis. The chemical cross-link procedure resulted in the generation of a complex mixture of heterogeneously cross-linked molecules with variable FBD and SK content, since the bifunctional agents used for chemical cross-link essentially cross-link any of the large number of lysine side-chains present in the participating molecules viz. SK and HPG. Thus, this procedure generates mixturs of molecules with undefined location of the cross-links between the molecules e.g. both dimmers and mummers with both homo- (e.g.,. SK—SK or FBD—FBD types) and hetero-crosslinked molecules with varying sites of cross-links are expected to be formed. In addition, it is noteworthy that the SK molecules chemically cross-linked with fibrin binding polypeptides disclosed in this patent showed an overall level of PG activator activity essentially comparable to that of unmodified SK, and no alteration was observed in the rate of PG activation, or the presence of an initial lag in the PG activation kinetics. It is quite clear that this invention related to the preparation of a heterogeneous population of cross-liked molecules with structures essentially undefined with respect to the cross-links' locations, and without any cross-correlation between the different structures in the ensemble of molecules and their corresponding functional properties. This is a serious limitation in the description of a drug intended for therapeutic application, in general, and with respect to the exact nature of the structure-function correlation in the collection of the cross-linked molecules, in particular.

In the past, hybrid SK derivatives with "kringle" type fibrin binding domains derived from human plasmin(ogen) fused to the former, and methods of obtaining the same by rDNA techniques, have been described (EU 0397 366 A1 and U.S. Pat. No. 5,187,098). However, five such Kringle regions are already present in the natural SK-Plasmin(ogen) activator complex, as noted before, being an integral part of PG in the activator complex, which has a weak fibrin affinity at best (Fears, R., 1989., *Biochem. J.* 261: 313). Hence, there is a need to impart a qualitatively different fibrin-affinity and/or specificity to the activator complex and utilize the affinity so imparted to obtain SK derivatives that display functional characteristics that help avoid the immediate activation of plasminogen upon contact with the latter.

Certain proteins are known to contain fibrin-associating "finger" domain/s, such as those present in fibronectin, a multi-functional protein with ability to interact with a number of other proteins besides fibrin e.g., collagen, heparin, actin etc (reviewed in Ruoslahti, E., 1988, *Ann. Rev. Biochem.* 57:375). TPA also possesses a "finger" the fibrin binding domain (FBD) that greatly helps in its fibrin association (Verheijen J. H. et al., 1986., *EMBO J.* vol. 5, pp. 3525). Methods for the imaging of fibrin-containing substances, such as pathological clots and/or atherosclerotic plaques in vivo by using large radio-labeled polypeptides derived from fibronectin, and bearing these FBDs have been disclosed (see: PCT WO 91/17765); this patent also discloses chemically cross-linked FBD-containing polypeptides and a thrombolytic agent (SK) to effect thrombus-targeted fibrinolysis. However, it is noteworthy that the SK molecules chemically cross-inked with fibrin binding polypeptides showed an overall level of PG activator activity essentially comparable to that of unmodified SK, and no alteration was observed in the rate of PG activation or the presence of an initial lag in the PG activation kinetics. Besides, the cross-linking procedure resulted in the generation of a complex mixture of heterogeneously cross-linked molecules with variable FBD and SK content, since the bifunctional agents essentially cross-linked any of the large number of lysine side-chains present in the participating molecules viz. SK and HPG likely generating both dimers and multimers with both homo- (e.g., SK—SK or FBD—FBD types) and hetero-crosslinked molecules. Moreover, this invention essentially disclosed the preparation of a heterogeneous population of chimeric molecules between SK and fibrin binding polypeptide with undefined covalent structures with respect to the sites of crosslinking as well as types of polymers so formed i.e. whether homo- (SK—SK or FBD—FBD typos) or hetero-types, so that any meaningful structure-functional cross-correlation between the different structures in the ensemble and their corresponding functional properties cannot be obtained. This is a serious limitation in a drug intended for therapeutic application particularly one administered through a parenteral route in human beings.

In contrast, the present invention provides novel clot-specific streptokinase proteins possessing altered plasminogen activation characteristics and a process for the preparation of different types of said proteins by recombinant DNA technology which have been designed using precisely defined elements of DNA polynucleotides that encode for fibrin binding domain and SK or their modified forms. The hybrid proteins so formed thus have two very important structural as well as functional elements, namely SK or its modified forms, and 'finger' type fibrin binding domain/s attached to each other through covalent peptide bonds in a predefined and predetermined order of juxtaposition with rest to each other (see FIG. 1 for types of such constructs, and the rationale for their construction, which is provided below) so that the hybrid, or chimeric, proteins so produced after expression in a suitable system possess discrete, definable covalent structures. In other words, the novel hybrid proteins contain SK or functionally relevant parts thereof, connected through polypeptide linkage/s with the relevant protein domains of human fibronectin that are capable of independently conferring fibrin affinity to the resultant hybrids in such a manner that the hybrid protein/s specifically display altered plasminogen activation characteristics. The latter is marked by the presence of an initial period of lag of several minutes' duration in the rate of PG activation by the hybrid SK derivatives (viz., time-delayed PG activation), which is followed by high rates of PG activation akin to that displayed by unmodified SK. In other words, the duration of the initial lag, which vanes depending on the type of hybrid construct, is rapidly followed by PC activation rates closely similar to that of natural type SK. Their simultaneous presence of the afore-mentioned two distinct biochemical properties in the same clot-dissolver protein molecule renders these hybrid streptokinases as very useful drugs for targeted, time-delayed clot lysis during thrombolytic therapy.

The biologically active form of Streptokinase (SK) is either the SK-plasminogen or SK-plasmin molecule/s, formed in the circulatory system by the association of SK with endogenous plasminogen soon after its administration on in vivo. This complex is also known as the activator complex, a highly specific protease that activates substrate molecules of plasminogen to plasmin, which proteolytically digests fibrin and helps restore blood circulation in occluded vessels (Castellino, C. J., 1981., *Chem. Rev.* 81:431). Unlike free SK, which does not possess fibrin affinity, this complex already possesses substantial fibrin affinity of its own due to the "kringle" fibrin binding domains present in the plasmin (ogen). part of the SK-plasmin(ogen) activator complex (Fears R., 1989., *Biochem. J.* 261: 313; see also references cited therein). Nevertheless, unlike other preferred plasminogen activator protein drugs such as tissue plasminogen activator (TPA) which possesses intrinsic fibrin affinity as well as a fibrin dependent plasminogen activation kinetics, the administration of SK during clot dissolution therapy often leads to unwanted systemic activation of plasminogen throughout the circulatory system due to immediate activation of circulating plasminogen, as opposed to the desired activation in and around the fibrin clot occluding the flow of blood through the affected vessel/s.

Thus, it will be of significant clinical advantage if SK could be engineered to posse increased fibrin affinity/specificity together with a markedly slower initial rate of activation of plasminogen (PG), but becoming capable of activating plasminogen in a manner similar to that of unmodified SK after an initial hiatus. Thus, soon after injection into the body, whilst it is still in an inactive or partially active state, the engineered SK will bind to the pathological fibrin clot while still in an inactive or partially active state, as it sojourns through the vascular system by virtue of the engineered fibrin affinity. However, after the initial lag in its PG activation kinetics is overcome in a few minutes, it will preferentially become activated in the immediate vicinity of the clot where it is now sequestered, thereby obviating or significantly minimizing the systemic PG activation coincident with natural SK administration which immediately activates PG upon administration. Thus, whilst the former property (of fibrin affinity) would be expected to confer on the new thrombolytic agent an ability to target itself to the immediate locale of the pathological clot and thus help build up therapeutically effective concentrations of the activator therein, the other property (of an initially slow kinetics of PG activation) would result in an overall diminished generation of free plasmin in the circulation. The net result shall be a continued and more efficient fibrinolysis at the target sustained by considerably lowered therapeutically effective dosages of the thrombolytic agent. In conclusion, a fibrin affinity per se in SK has little beneficial consequences (which anyway the SK-PG complex possesses in some measure) unless the systemic PG activation is thwarted and/or delayed An important attribute of the present invention is the preparation of different types of novel and the undisclosed chimeric SK derivatives produced by recombinant DNA technology using defined gene-segments of SK and FBD combined in a pre-designed manner. These novel genetic constructs have been designed using precisely defined DNA elements that encode for SK and fibrin binding domains, or their modified forms so as to retain the functional characteristic of each (PG activation and fibrin affinity, respectively) as well as a characteristically altered PG activation kinetics. The chimeric proteins so produced have two types of elements (SK and the 'finger'-type fibrin binding domains, or there modified forms) in a predefined and predetermined order of juxtaposition with respect to each other, so that the chimeric proteins expressed from these genes possess discrete, definable covalent structures. In other words, the chimeric proteins contain SK or parts thereof, connected through polypeptide linkage with the relevant protein domains that confer fibrin affinity to the resultant hybrids and also specifically result in altered kinetics of PG activation. The latter is characterized by an initial lag, or absence of PG activation, of several minutes duration (viz., time-delayed PG activation), followed by high rates of PG activation akin to that of unmodified SK. The initial lag (which varies from approx. 8 min to 25 min depending on the design of the SK derivative) is rapidly followed by high rate of PG activation closely similar to that displayed by natural type SK. The simultaneous presence of the afore-mentioned two biochemical properties in the same PG activator molecule has not been disclosed in the SK-derived molecules in either of the patent disclosures cited above. In addition, the present patent discloses now combinations of DNA sequences that have been used to express the novel protein molecules with a unique combination of functional properties, mentioned above, which am not disclosed in the other patents.

The rationale for the construction of hybrid SK derivatives as disclosed in the process of the present invention with both fibrin specificity and delayed PG activation kinetics is explained below.

The molecular basis for the fibrin affinity displayed by fibronectin has been studied in some detail in recent years (Matsuka, Y. V., Medved, L. V., Brew, S. A. and Ingham, K. C., 1994, *J. Biol. Chem* 269:9539). Under physiological conditions, FN first interacts reversibly (but with relatively high affinity) with fibrin and is then covalently incorporated into the fibrin clot matrix through clotting factor XIII, a tranglutaminase (reviewed in,. Ruoslahti, E., 1988*, Ann. Rev. Biochem.* 57:375), whose action results in the covalent cross-linking between FN and a lys residue in fibrin(ogen) at the reactive Gln (residue 3) of the former. The region/s responsible for the interaction of FN with fibrin have been identified to reside both in the N-terminal as well as the C-terminal ends of this multi-domain protein. The N-terminal region of FN comprises of five finger modules (FBDs) as well as tranglutaminase cross-linking (TG) site, whereas the C-terminal region, lacking a TG site, contains three modules, as demonstrated by the binding of different polypeptides derived from FN carrying these two broad regions to fibrin-agarose. The exact domains in the N-terminal region responsible for the strong binding of the FN module, and their relative contributions towards this interaction have been analysed closely (Matsuka, Y. V., Medved, L. V., Brew, S. A. and Ingham, K. C., 1994, *J. Biol. Chem*, 269:9539 and Rostagno et al., 1994; *J. Biol. Chem.* 269; 31938) by expressing DNA segments encoding various combinations of the modules in heterologous cells and/or by examining the fibrin binding properties of polypeptide fragments carrying these modules prepared by limited proteolysis of FN. These studies clearly identified that of all the individual modules present in the N-terminal region of FN, the bi-modular arrangement viz., FBD 4 and 5 domains, displayed a fibrin affinity significantly comparable to the interaction of the full-length FN molecule, in contrast to all the other domains either as pairs or individually (including 4 and 5) which displayed poor affinity at 37° C. It is therefore clear from these studies that physiologically effective fibrin binding is not a common property of all the modules, either individually or in pairs, but is principally located in the FBD pair of 4 and 5, and to a relatively lesser extent, in domains 1 and 2.

To achieve the functional objective of an initially time-delayed PG activation kinetics by the hybrid S-K derivatives, our design utilizes the fusion of selected regions of the FBDs of human fibronectin or its homologous sequences present in other proteins with SK (or its partially truncated forms) at strategically useful points so as to kinetically hinder the initial interaction of SK with PG necessary to form the 1:1 stoichiometric activator complex. It is known that of the 414 residues constituting native SK only the first 15 residues and the last 31 residues are expendable, with the resultant truncated polypeptide being nearly as active as the native full-length protein in terms of PG activation ability (Jackson, K. W. and Tang, J. (1982) Biochemistry 21:6620). Further truncation at either end results in drastic decrease in the activity associated with the molecule (Malke, H., Roe, B., and Ferretti, J. J. (1987) In: *Streptococcal Genetics*. Ferretti, J. J., and Curtis, R. III [Ed.] Proc. American Society for Microbiology., Wash. D.C. p. 143). It has been demonstrated that SK interacts with PG through at least two major loci, mapped between residues 16–51 and 230–290 (Nihalani, D., Raghava, G. P. S., and Sahni, G., 1997, Prot. Sci. 6:1284), and probably also the region in and around residues 331–332 (Lin, F. L., Oeun S., Houng, A., and Reed, G. L., 1996, Biochemistry 35:16879); in addition, the sequences at the C-terminal ends, especially before the last 30–32 residues of the native sequence (Kim. I. C., Kim, J. S., Lee, S. H., and Byun, S. M. 1996, Biochem. Mol. Bio. Int. 40:939. Lee, S. H., Jeong, S. T., Kim, I. C. and Byun S. M. 1997 *Biochem. Mol. Bio. Int.* 41:199. Fay, W. P., Bokka, L. V., 1998*, Thromb. Haemost.* 79;985) are important in generating the activator activity associated with the complex. Since a primary consideration in designing the SK-FBD chimeras was the engineering of a decreased, or kinetically slowed, initial PG activation rate, we reasoned that either the C- or N-termini (or both, together) could be utilized to bear the FBDs in the hybrid structures, and that the presence of such extra domains in SK, either full-length or already truncated to the most functionally relevant regions of human fibronectin that can independently bind fibrin under physiological conditions (detailed earlier) and would also suitably retard and/or delay the PG activation rates observed normally with native SK and PG by interfering in the interactions of SK with PG to generate a functional activator complex. If the polypeptide in between these two distinct parts constituting the chimera were sufficiently flexible, proteolytic scission in this region would then result in the removal of the retarding/inhibiting portion (FBD component) from the SK-FBD hybrid and lead to a burst of PG activation after an initial delay. This proteolysis could be mediated by the small amounts of endogenous plasmin generated in the vicinity of the pathological clot by intrinsic plasminogen activator/s of the system, such as TPA, urokinase etc already present in the circulatory system. Indeed, this premise was borne out by experimentation, which showed that the lag times of PG activation by the SK-FBD chimeras disclosed in this invention were directly governed by plasmin-mediated proteolysis of the hybrid proteins leading to the liberation of the FBD portion from the SK-FBD followed by rapid PG activation by the SK. The direct implication of this functional property in a plasminogen activator is that once injected into the body, the protein could then traverse in an inactive state through the circulatory system and bind to the pathological clot by virtue of the fibrin affinity imparted by the fibrin binding domains thereby obviating or minimizing systemic PG activation. Thus, if the thrombolytic agent traverses the circulation prior to this activation (which is known to require 3–5 minutes in the human circulation), the fibrin affinity in the chimera would allow it to bind to the clot, thereby helping to localize the PG activation in and around the immediate vicinity of the thrombus.

The amino acid sequence of human FN is known to be composed of three types of homologous repeats (termed type-1, type-2 and type-3), of which the FBDs at the amino terminus of FN are made of five type-1 repeals, each approximately 50 residues long and containing two disulfide bridges. The C-terminus of FN also has three type-2 homology repeats that are involved in fibrin-FN interactions. Therefore, altogether, a large portion of the FN molecule, representing the several N- and C-terminally located FBDs, could be linked with SK if all of the fibrin interacting regions need to be incorporated into the contemplated SK-FBD chimeras. However, such a design produces a chimeric protein that is not only too bulky, but also decreases the probability for the polypeptide to fold into a biologically active conformation due to the presence of a large number of S—S bridges that may form non-native, intra- and inter-molecular disulfide bonds. Instead, a potentially more worthwhile proposition is to seek miniaturised but, nevertheless, functionally active combinations of selectively truncated regions of SK and/or FBDs.

OBJECTS

The main objective of the invention is to provide a novel chimeric streptokinase-based plasminogen activator protein molecule with advantageous characteristics of improved fibrin affinity and plasminogen activation kinetics characterized by an initial lag of several minutes' duration (5 to 30 minutes) prior to attainment of full-blown capability of PG activation.

Another object is to provide a system for the production of the hybrid polypeptides, which includes DNA segments/polynucleotide blocks encoding the polypeptides, plasmids containing these genetic elements capable of their expression into protein, as well as microorganisms transformed with these plasmids.

Yet another object is to design a process for the production of the hybrid plasminogen activator protein molecules in pure and biologically active form for clinical and research applications.

Another object is to provide an improved process for the intracellular production of large quantities of SK, or its modified forms, in *E. coli* using an altered DNA polynucleotide, and obtain these in a pure and biologically active form.

A further object is to provide pharmaceutical compositions comprising novel chimeric streptokinase-based plasminogen activators of the invention and pharmaceutically acceptable carriers.

SUMMARY

The invention provides hybrid plasminogen activator comprising a polypeptides bond union between streptokinase (SK), or modified forms of SK, or suitable parts thereof, which art capable of plasminogen (PG) activation, with fibrin binding regions of human fibronectin selected from the pair of fibrin binding domains 4 and 5, or domains 1 and 2, or modified forms thereof, to achieve various motifs for joining the fibrin binding domain with streptokinase or its modified forms, so that the hybrid plasminogen activator possesses the ability to bind with fibrin independently and also characteristically retains a plasminogen activation ability which becomes evident only after a pronounce duration, or lag, after exposure of the plasminogen activator to a suitable animal or human plasminogen.

DETAILED DESCRIPTION

The present invention provides a hybrid streptokinase-based plasminogen activator prepared by conventional recombinant DNA techniques e.g., those described in 'Sambrook et al., Molecular Cloning: A Laboratory Manual' (II$^{nd}$ Ed., Cold Spring Harbor Press, 1989) and 'DNA Cloning' (vol. I to III) (Glover, D. M., [Ed.], IRL Press Ltd., London; 1987), among several other manuals/compendia of protocols. and the techniques of protein purification and characterization, in particular the various chromatographic methods employed conventionally for purification and downstream processing of natural and recombinant proteins and enzymes viz, hydrophobic interaction chromatography (HIC), ion-exchange and gel filtration chromatographies, and affinity chromatographic techniques well-known in the field of protein biochemistry (e.g., in this regard, reference may be made to: (i) Protein purification. Principles, high resolution methods and applications Janson, J-C., and Ryden, L., [Ed.], VCH Publishers Inc., New York, 1989; (ii) Process Chromatography: A practical guide. Sofer, G. K., and Nystom, L. E., [Ed.], Academic Press, New York, 1989).

The advantage of the present invention lies in its disclosure of the design of structurally defined hybrid DNA polynucleotide constructs in which the translational in-frame fusion of the DNAs encoding SK or its modified forms, and the minimally essential parts of the fibronectin-encoding DNA polynucleotides essential for significant fibrin affinity on their own, such as those FBDs that possess independent fibrin binding capability (such as finger domains 4 and 5 of human fibronectin) is carried out in such a configuration confers the additional property of a time-delayed plasminogen activation in the resultant hybrid protein molecules. The latter are expressed by translation of the hybrid polynucleotides formed between the SK-encoding DNA and he FBD encoding DNA in a suitable host cell such as a bacterium, yeast, animal, plant cell etc. The resultant hybrid proteins, containing SK and FBD portions fused to each other through polypeptide linkages, can be isolated in pure form by conventional methods of protein purification.

BRIEF DESCRIPTION OF THE DRAWINGS

FIG. 3. DNA and protein sequence of streptokinase of *S. equisimilis* H46A (SEQ ID NOs:1 and 2, respectively) (GeneBank accession number; gb/K02986/STRSKC).

FIG. 6. DNA and protein sequence of the gene-segment encoding for FBDs 1–5 of human fibronectin (SEQ ID NOs:3 and 4, respectively) (the DNA sequence has been obtained from EMBL; the file and accession no.'s are ID-HSFIBI and X02761, K00799, K02273, X00307, X00739.

FIG. 11. Nucleotide sequence of SK-NTRN gene (SEQ ID NO:5).

FIG. 14. Nucleotide sequence of SK-NTR gene (SEQ ID NO:6).

FIG. 17b. DNA sequencing data of SK-FBD(4,5) hybrid cassette in T7 expression vector, pET23(d) (SEQ ID NO:9).

FIG. 19b. DNA sequencing data of SK-FBD(1,2) hybrid cassette in T7 expression vector (SEQ ID NO:10).

FIG. 21b. DNA sequencing data of FBD(4,5)-SK gene block as present in the T7 expression vector pET23(d)-FBD (4,5)-SK (SEQ ID NO:11).

FIG. 22b. DNA sequencing data of FBD(4,5)-SK-FBD (4,5) gene block as present in the T7 expression vector pET23(d)FBD(4,5)-SK-FBD(4,5) (SEQ ID NO:12).

FIG. 24 shows results with: closed triangles, 100 nm SK; open triangles, 50 nm SK; closed circles, 200 nm SK-FBD (4,5); closed squares, 100 nm SK-FBD(4,5); open squares, 50 nm SK-FBD(4,5).

Accordingly, the present invention provides a hybrid plasminogen activator comprising a polypeptide bond union between streptokinase (SK), or modified forms of SK, or suitable parts thereof, which are capable of plasminogen (PG) activation, with fibrin binding regions of human fibronectin selected from the pair of fibrin binding domains 4 and 5, or domains 1 and 2, or modified forms thereof, so that the hybrid plasminogen activator possesses the ability to bind with fibrin independently and also characteristically retains plasminogen activation ability which becomes evident only after a pronounced duration, or lag, after exposure of the plasminogen activator to a suitable animal or human plasminogen. FIG. 1 describes the different designs of the SK-FBD hybrid proteins schematically as disclosed in the invention.

Figures 1, 2:
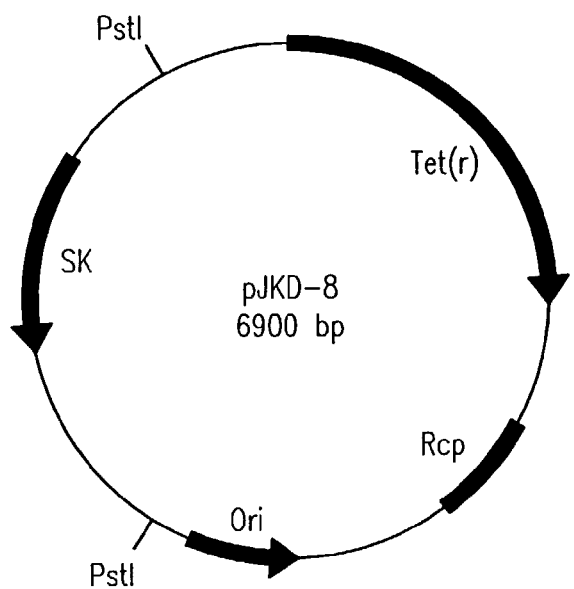
FIG. 1. Schematic representation of different chimeric proteins prepared by the fusion of SK and FBDs.
FIG. 2. Map of plasmid pJKD-8, containing SK gene from *S. equisimilis* H46A.

In an embodiment, the invention provides a hybrid plasminogen activator which caries out plasminogen activation only after a lag period varying between 5 and 30 minutes after exposure of the plasminogen activator to a suitable animal or human plasminogen.

In a further embodiment, the invention provides a DNA segment encoding the hybrid plasminogen activator.

In yet another embodiment, the invention provides an expression vector containing a DNA segment encoding the hybrid plasminogen activator.

In another embodiment, the invention provides prokaryotic or eukaryotic cells, transformed or transfected with expression vectors, and capable of expressing the hybrid plasminogen activators.

The invention further provides a method for the preparation of hybrid plasminogen activators possessing useful plasminogen activation characteristics, said method comprising steps of:

(a) Preparing a first DNA encoding a nucleotide sequence for streptokinase or any of its modified forms, by conventional biochemical or chemical methods or appropriate combinations thereof, to produce a transitional product, which is a polypeptide that can activate plasminogen (b) Preparing a second DNA polynucleotide by known biochemical or chemical methods or appropriate combinations thereof, that encodes for the fibrin binding domains selected from the of fibrin binding domains 4 and 5, or domains 1 and 2, or their modified forms, that are capable of conferring affinity and/or specificity for fibrin, and linking these to another DNA molecule that is capable of undergoing multiplication in a suitable host cell, (c) Construction of hybrid polynucleotides, between the first DNA encoding for streptokinase, or its modified forms; that encode for a polypeptide capable of plasminogen activation, with the second DNA encoding for the fibrin binding domain (FBD) of fibronectin by conventional methods, in the native translational codon frame starting with an initiator codon, and joining of the hybrid polynucleotide into a recipient DNA molecule, such as a plasmid capable of a autonomous replication in a host cell, or capable of integrating into the genomic DNA of a suitable host cell, and expressing the hybrid protein therein, (d) Introducing the DNA containing the hybrid polynucleotide constructs obtained in step (c) into an appropriate host, selected from the group comprising E. coli, Bacillus sp., yeast, fungus, plant, animal cell by conventional methods.

(e) Culturing the host cells expressing the SK-FBD chimeric polynucleotide using known procedures, (f) Isolating components of the culture, selected from extracellular fluid from fermentation, intracellular milieau of the host cell or combinations thereof, that harbour the expressed chimeric polypeptide in an enriched form, and then partially purifying the chimeric polypeptides using conventional procedures selected from the group comprising centrifugation, ultrafiltration, precipitation with salts or organic solvents etc, or chromatography on suitable media, or combinations thereof, (g) Refolding the hybrid polypeptide to a biologically active and structurally intact form, if required, (h) Further purifying the biologically active hybrid polypeptide from the relatively crude or partially pure material/s or call-free lysate obtained at step (f), or (g) above, after refolding, using conventional methods of protein purification, or by affinity chromatography on a suitable matrix comprising immobilized fibrin or fibrinogen, or specific antibodies that recognize and bind with the active, biologically active hybrid proteins, In an embodiment, the invention provides a method for the production of the hybrid plasminogen activator proteins including DNA segments/polynucleotide blocks encoding the polypeptides, plasmids containing these genetic elements capable of their expression into protein, as well as microorganisms or other suitable host cells transformed with these plasmids.

In another embodiment, the invention provides a method for the production of the hybrid plasminogen activator molecules in pure and biologically active farm for clinical and research applications.

In another embodiment, the invention provides a method for the intracellular production of large quantities of SK, or its modified forms in bacteria such as *E. coli*, using a polynucleotide block that is altered as compared to that of the natural DNA sequence encoding for SK or its modified forms, and obtain these in a pure and biologically active form.

Figure 13:
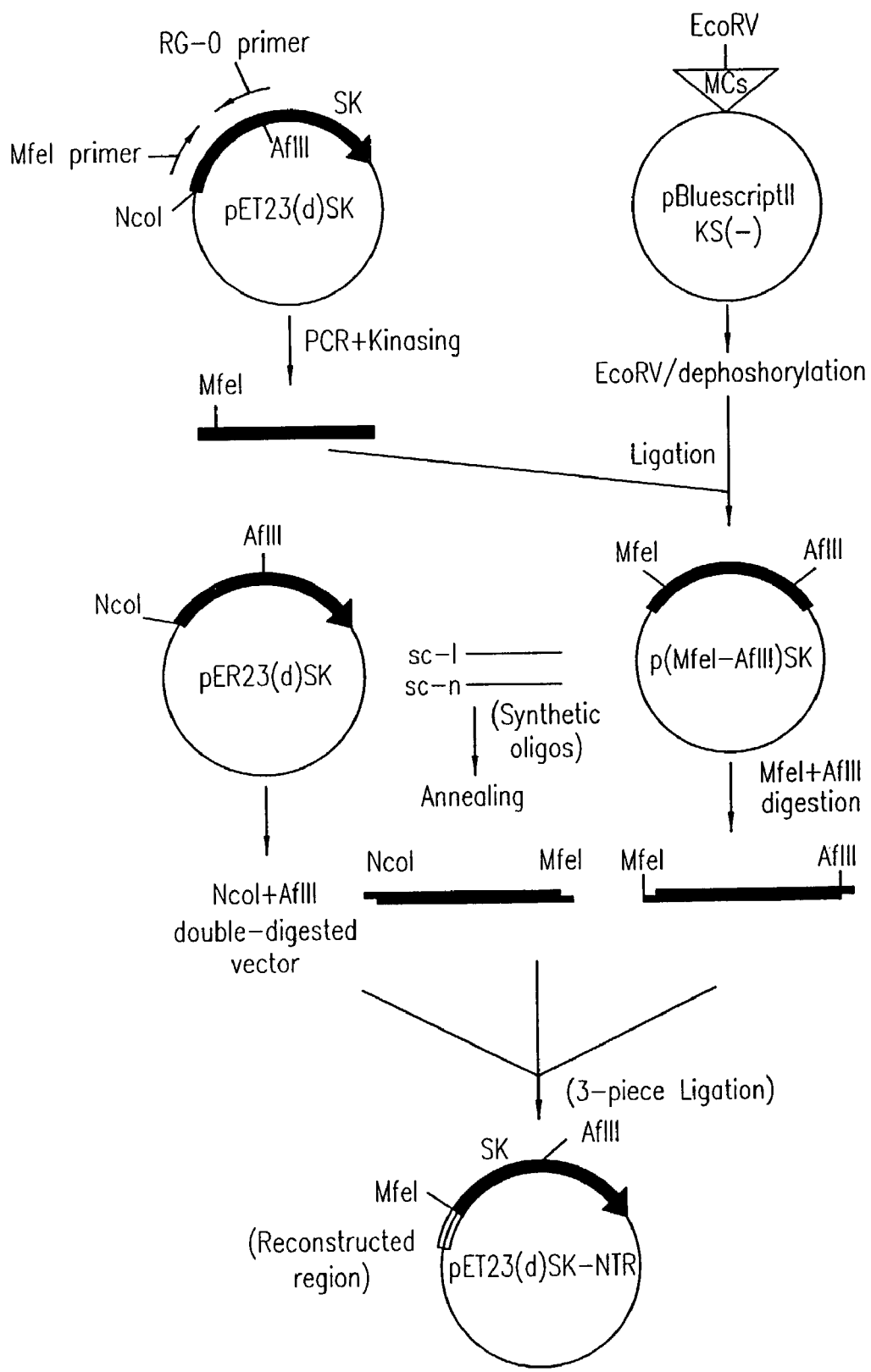
FIG. 13. Schematic flow diagram depicting the main steps in the construction of a plasmid vector [pET23(d)SK-NTR] for the intracellular hyper-expression of a semi-synthetic SK gene in which the 5'-end of the open-reading-fame for SK was selectively modified in a translationally silent manner at the DNA level, so that it encoded for the primary structure of *S. equisimilis* SK.

In yet another embodiment, the invention provides a method wherein the 5'-end of the SK-encoding polynucleotide utilized for expression of SK, or its modified forms such as the SK-FBD chimeric polypeptides, is modified, as exemplified by the DNA sequence provided in FIG. 13, by mutagenesis by known biochemical or chemical DNA synthesis techniques, or their combination, such that the secondary structure-forming capability (e.g., the intramolecular hydrogen bonding capability) of its transcript is diminished, resulting in increased efficiencies of expression of SK or its modified forms such as SK-FBD chimeras in the heterologous host cell.

In another embodiment, the invention provides a method wherein the 5'-end of the SK-encoding DNA or its modified forms such as the SK-FBD chimeric polypeptides, is modified by mutagenesis by known biochemical or chemical DNA synthesis techniques, or a suitable combination thereof, in such manner that the codons utilized in the DNA polynucleotide are compatible with those frequently utilized in *E. coli* or the host cell used for the expression of the genes.

In another embodiment, the invention provides a method wherein the DNA encoding those fibrin binding domains that possess independent fibrin binding capability are fused in the correct translational frame at the 5'-end of the SK-encoding DNA, after a translational start codon, and then expressed into protein of the form exemplified in FIG. 1C, refolded oxidatively and isolated in the purified form, to obtain the desired characteristic in the chimera viz., characteristic PG activation properties characterized by an initial lag in the PG activation rates together with significant fibrin affinity.

In another embodiment, the invention provides a method wherein the fibrin binding domain are fused in-frame at the C-terminal end of the SK, or its modified form, to obtain a hybrid SK-fibrin binding domain protein that contains selected fibrin binding domains at the C-terminal end of the SK portion of the chimera after expression of the hybrid DNA in a suitable host cell. as exemplified in FIGS. 1A and 1B, to obtain the desired characteristic in the chimera viz., characteristic PG activation properties characterized by an initial log in the PG activation rates together with significant fibrin affinity.

In another embodiment, the invention provides a method wherein the fibrin binding domains are fused trough polypeptide linkage at the C-terminal end of the SK devoid of upto 45 amino acids, preferably 31 amino acid residues, Thus, a hybrid SK-FBD protein is generated that contains selected fibrin binding domains fused at the C-terminal end of a truncated SK, thus yielding a chimeric protein that has both fibrin affinity as well as delayed PG activation properties.

In yet another embodiment, the invention provides a method wherein fibrin binding domains are fused at both the ends of SK, or its modified forms that retain a plasminogen activator ability, simultaneously (in the configuration represented as 'FBD-SK-FBD'; as schematically depicted in FIG. 1, D) to achieve the desired functionality in the hybrid construct viz., characteristic plasminogen activation properties characterized by an initial lag in the PG activation rates together with significant fibrin affinity.

In another embodiment, the invention provides a method wherein the novel chimeric polypeptides are expressed in *E. coli* or other suitable host cells.

In another embodiment, the invention provides a method wherein SK or its truncated form/s are fused through polypeptide linkages with the fibrin binding domains known to possess independent fibrin binding capability through a short linker peptide region comprising of a stretch of amino acid sequence that is not conformationally rigid but is flexible, such as those predominantly composed of Gly, Ser, Asn, Gln and similar amino acids.

In another embodiment, the invention provides a method wherein SK or its modified forms are fused with fibrin binding domains through a "linker" peptide composed of amino acid sequences that provide varying levels of local conformational flexibility by incorporating sequences that fold into relatively rigid secondary structures such as beta-turns so as to obtain different chimeric PG activator proteins with desirable initial lag-times in their plasminogen activation kinetics.

In another preferred embodiment, the SK-FBD hybrid polypeptides are expressed in *E. coli* using known plasmids under the control of strong promoters, such as tac, trc, trp, T7 RNA polymerase and the like, which also contain other well known features necessary to effect high level expression of the incorporated DNA polynucleotides encoding for the hybrid Streptokinase-fibrin binding domain polypeptides e.g. Shine-Delgarno sequence, transcription terminating signals etc.

In yet another embodiment, SK or its truncated forms are fused either at the amino- or C-termini, or both through polypeptide linkages with the FBDs known to possess independent fibrin binding capability, such as domains 4 and 5, through short 'linker' regions, as described above, that contain amino acid sequence/s providing varying levels of local conformational flexibility to the linker segment between the SK and FBD portions of the hybrid protein/s.

In yet another embodiment, various chemical or physical agents, such as iso-propyl- beta-D-thio galacto pyranoside (IPTG), lactose, low or high temperature change, changes in salt or pH of medium, ethanol, methanol, and the like, are used to induce high levels of the SK or the various hybrid polypeptides in the host cell in which the hybrid polynucleotides are being expressed.

In another preferred embodiment, the hybrid SK-FBD polynucleotides are expressed in *E. coil*.

In yet another embodiment, the *E. coli* cells are lysed by chemical treatment such as the use of chaotropic salts e.g. guanidinium hydrochloride and the like, to effect the liberation of the SK or its modified hybrid forms, which are then purified using conventional procedures.

In yet another embodiment, the invention provides a method wherein the host *E. coli* cells are lysed by chemical treatment such as chaotropic salts e.g., guanidinium hydrochloride and the like, to effect the liberation of the SK or its modified chimeric forms, follow by purification using conventional methods.

In another embodiment, the invention provides a method wherein the crude, cell-lysates obtained, using either conventional methods or by employing chaotropic salts, from cells elaborating the chimeric polypeptides are subjected to air oxidation to refold the chimeric polypeptides to their biologically active conformations containing the native cystine connectivities.

In another embodiment, the invention provides a method wherein the crude cell-lysates obtained using either conventional methods selected from the group consisting of enzymatic lysis of cells, ultrasonic lysis, lysis by mechanic meal or by employing chaotropic salts, from cells elaborating tho chimeric polypeptides are subjected to oxidation and refolding using a mixture of reduced and oxidized glutathione of a suitable redox potential that allows the chimeric polypeptides to refold to their biologically active conformations.

In yet another embodiment, the invention provides a method wherein the refolding reaction is carried out in the presence of immobilized fibrin to promote a more efficient ligand-induced refolding of the epitopes responsible for fibrin affinity in the said chimeric polypeptides, and consequently higher yields of the biologically active chimeric protein constructs.

In another embodiment, the invention provides a method wherein the biologically active chimeric polypeptides are purified selectively from other proteins or unfolded SK-FBD polypeptides, by affinity chromatography on immobilized fibrin(ogen) e.g. fibrin- or fibrinogen-agarose.

In an other embodiment, the invention provides a method wherein a chimeric plasminogen activator protein is used as a medicant for the treatment or prophylaxis of thrombolytic diseases. The activator may be formulated in accordance with routine procedures as pharmaceutical composition adapted for intravenous administration to human beings, and may contain stabilizers such as human serum albumin, mannitol etc, solubilizing agents, or anesthetic agents such as lignocaine and the like.

In yet another embodiment, the invention provides a pharmaceutical composition comprising a hybrid plasminogen activator and stabilizers such as human serum albumin, mannitol etc, solubilizing agents, anesthetic agents.

In a further embodiment, the pharmaceutical composition of the invention comprises a chimeric plasminogen activator protein used as a medicant for the treatment or prophylaxis of thrombolytic diseases and pharmaceutically acceptable carriers. The activator may be formulated in accordance with routine procedures as pharmaceutical composition adapted for intravenous administration to human beings, and may contain stabilizers such as serum albumin, mannitol etc, solubilizing agents, or anesthetic agents such as lignocaine and the like.

The DNA polynucleotides encoding the various streptokinase-fibrin binding domain hybrid constructs depicted schematically in FIG. 1 be made utilising rDNA and selective DNA amplification techniques (e.g., the well-known polymerase chain reaction technique, abbreviated PCR) (reference, in this regard may be made to: Saiki, R. K. Scharf, S., Faloona, F., Mullis, K. B., Horn, G. T., Erlich, H. A., and Amheim, N., 1985, *Science* 230: 1350; Mullis, K. B., and Faloona, F., 1987, *Methods in Enzymol.* 155:335). The hybrid genes are then expressed in heterologous hosts such as bacteria (e.g. *E. coli*), or other suitable organisms, to obtain the chimeric polypeptides. Bacterial host calls (*E. coli* XL Blue) harbouring the various plasmid constructs expressing the different SK-FBD hybrid proteins (see Examples section) have been deposited in he Microbial Type Culture Collection (MTCC), Institute of Microbial Technology, Chandigarh (a constituent laboratory of C.S.I.R., India). The accession numbers of these constructs are: BPL 0013 for the pET 23(d)-NTR-SK-FBD(4,5) construct (see FIG. 17a for map of this plasmid); BPL 0014 for pET 23(d)-SK-NTR-FBD(1,2) (see FIG. 19a); BPL 0015 for pET23(d)FBD (4,5)-SK (see FIG. 21a for map of this plasmid construct); BPL 0016 for pER23(d)FBD(4,5)-SK-FBD(4,5) (see FIG. 22a for map); 0017 for pET73(d)SK-NTR (see FIG. 13 for map of this plasmid construct). The proteins expressed from these plasmids can be expressed in suitable host cells (e.g. *E. coli* BL 21) and then purified to render them substantially free of other components derived from the host producer cells. In case the polypeptide is expressed in a host system not capable of efficient re-oxidative folding of the primary translational product/s of the hybrid gene e.g. *E. coli*, an intermediate in vitro refolding stop is introduced subsequent to the expression step. Alternatively, the hybrid constructs can be expressed in cell systems capable of efficient oxidative refolding of translational products e.g. yeast, animal cells etc.

The DNA polynucleotide encoding for SK was first cloned in a bacterial plasmid in *E. coli*. after isolation from the wild-type *S. equisimilis* genomic DNA according to known procedures (Malke, H., and Ferretti, J. J., 1984, *Proc. Nat'l Acad. Sci.* 81: 3557) and in recent research publications available in the public domain (Pratap, J., Kaur, J., Rajamohan G., Singh, D., and Dikshit, K. L., 1996, *Biochem, Biophys. Res. Commun.* 227:303). In the process of the present invention, the DNA corresponding to the translational open-reading-frame (ORF) of SK has been further modified with respect to its 5'-coding sequences so that after cloning in an expression vector under the control of a strong promoter, large quantities of biologically active SK are produced intracellularly. The DNA sequence of the SK gene from *Streptococcus* species (American Type Culture Collection accession No. 12449; this strain has served as the producer stain for numerous studies on streptokinase, and is often referred to as *Streptococcus equisimilis* H46A in the scientific literature). The corresponding amino acid sequence of the mature protein are provided in FIG. 3. The restriction enzyme map of the SK-encoding DNA is provided in FIG. 4.

Figure 5:
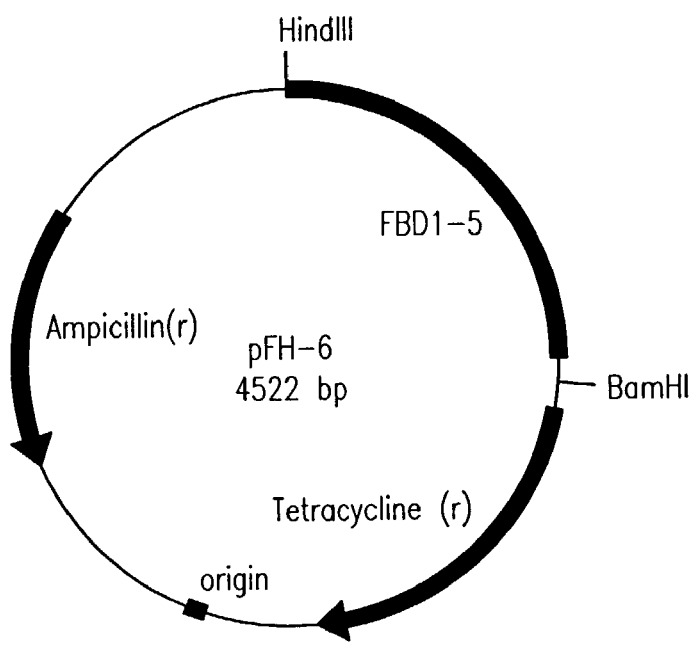
FIG. 5. Map of plasmid pFH-6, containing FBD 1 to 5 encoding sequences according to Kornhblitt, A. R., Umezawa, K., Vibe-Pedersen K. and Baralle, F. E., (1985) *EMBO J.* 4:1755.
Figure 7:
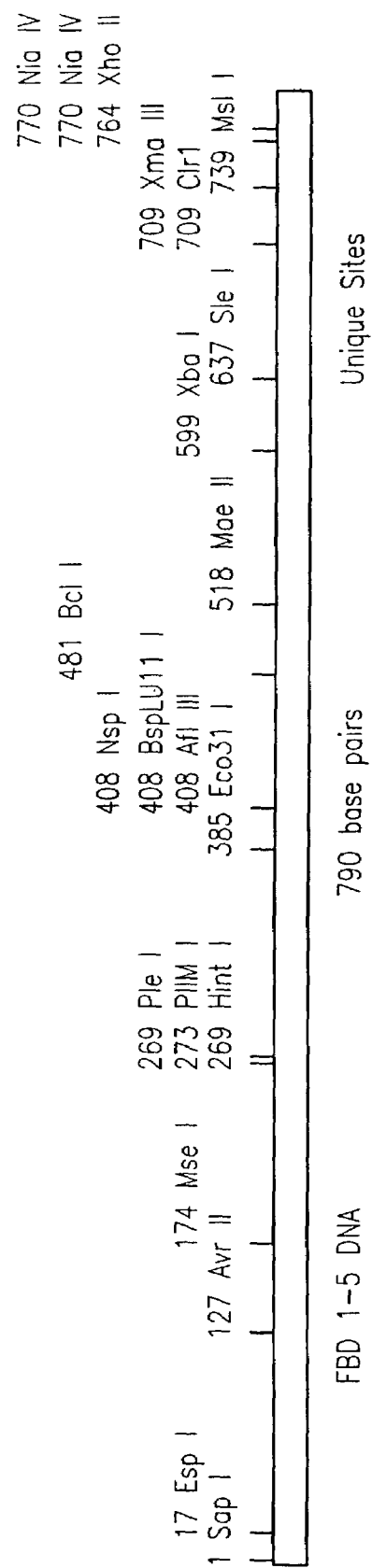
FIG. 7. Restriction enzyme map of DNA encoding the five N-terminally located FBDs of human fibronectin.

The DNA polynucleotide sequences encoding for the fibrin binding domains of human fibronectin were selectively amplified from known plasmids containing cloned cDNA for the FN gene. Kornblihtt, A. R., Vibe-Pedersen, K., and Baralle, F. E., 1983, *Proc. Nat'l. Acad. Sci.* 80:3218. have cloned the cDNA encoding for the human fibronectin (FN) gene in a plasmid vector in *E. coli* (pFH1). This cDNA extends approx. 2.1 kb from the poly-A tail of the mRNA of fibronectin, around one-fourth of the estimated size of the human FN message (approx. 7900 nucleotides). By further mRNA "walking" type of experiments, these investigators carried out the construction of longer cDNA clones using synthetic oligonucleotides complementary the DNA of clone pFH1. By this method, cDNAs corresponding to the complete FN mRNA were prepared and cloned in several vectors (Kornhblitt A. R., Umezawa, K, Vibe-Pedersen, K., and Baralle, F. E., (1985) *EMBO J.* 4:1755). One such plasmid (pFH6) contained the entire sequences coding for the FBDs of the N-terminal region of human FN (as represented in FIG. 5 showing the map of this plasmid, and in FIG. 6 showing the nucleotide and amino acid sequence of the FBD regions contained in this plasmid and FIG. 7 for its restriction enzyme map). Plaid pFH6 served as the source for these sequences in the construction of the SK-FBD hybrids. The fibrin binding domains located in the N-terminal region of human FN gene were selectively amplified by PCR using specially designed oligonucleotide primers that hybridized with DNA sequences flanking the FBD DNA segments to be amplified. These primers also contained non-hybridizing sequences at their 5'-ends that provided the intergenic sequence (i,e. between the SK and FBD DNA) as well as a restriction site through which the amplified DNA could be ligated with the SK gene in-frame in a plasmid vector. The cloned hybrid gene was then expressed in E. coli so as to produce large quantities of the chimeric polypeptide. This protein was then isolated from the E. coli cells and subjected to a process of purification and refolding to a biologically active form. Similarly, different designs of the SK and FBD hybrids were then constructed using recombinant DNA methods, expressed, and isolated in biologically active, purified forms. Analysis of the properties of these proteins established that these indeed possessed the functional properties expected from their design i.e. plasminogen activation ability as well as fibrin selectivity. They also displayed the additional desired property of a very slow initial kinetics of PG activation, which, after a lag varying between 5–30 minutes, depending on the construct, was overcome, leading to high rates of PG activation comparable to native SK.

The invention and its embodiments are illustrated by the follows examples, which should not be deemed to limit the scope of the invention in any manner. Various modifications that may be apparent to those skilled in the art are deemed to fall within the scope of the invention I. General Method Used in Examples.

1. Recombinant DNA methods: In general, the methods and techniques of rDNA well known in the area of molecular biology were utilised. These are readily available from several standard texts and protocol manuals pertaining to this field of the art, for example, Sambrook et al., Molecular Cloning: A Laboratory Manual ($II^{nd}$ edition, Cold Spring Harbor Press, New York., 1989; McPherson, M. J., Quirke, P., and Taylor, G. R., [Ed.] PCR: A Practical Approach. IRL Press, Oxford., 1991). However, pertinent in the context of specific experiments describing the present invention, particularly where modifications were introduced to established procedures, are indicated in the Examples wherever relevant.

2. Casein-plasminogen overlay for detection of SK activity: bacterial colonies producing streptokinase can be routinely detected by overlay of casein and human plasminogen in soft agar (Malke, H., Ferretti, J. J., 1984, Proc. Natl. Aca. Sci. 81:3557). Ten ml soft agarose mixture consisting of 0.8% agarose, 10% skimmed milk approx. 200 ug of human plasminogen, 150 mM NaCl, and 50 M Tris-Cl (pH 8.0) is poured on top of the plates. The plates are incubated at 37° C. for 2–6 h. Positive streptokinase activity is indicated by the appearance of zones of clearance around the colonies (halo formation).

3. Zymography: proteins from total cell lysates are separated on 10% SDS-PAGE. After completion of electrophoresis run gel is washed with 2.5% Triton X-100 to remove any SDS. It is then thoroughly rinsed with standard buffer 0.05 M Tris Cl (pH 7.5) for Triton X-100 removal. The gel is laid on 0.6% agarose plate containing 10% skimmed milk and 0.5 mg/ml human plasminogen. After incubating at 37° C. for 2–3 h, an active SK band is visualized as a clear band.

4. SDS-PAGE analysis of proteins: SDS-PAGE is carried out, essentially according to Laemmli, U.K., 1970, Nature 227:680 with minor modifications, as needed. Briefly, protein samples are prepared by mixing with an equal volume of the 2× sample buffer (0.1 M Tris Cl, pH 6.8; 6% SDS; 30% glycerol; 15% beta-mercaptoethanol and 0.01% Bromophenol Blue dye). Prior to loading onto the gel, the samples are heated in a boiling water bath for 5 min. The discontinuous gel system usually has 5% (acrylamide conc) in the stacking and 10% in the resolving gel. Electrophoresis is carried out using Laemmli buffer at a constant current of 15 mA first, till the samples enter the gel and then 30 mA till the completion. On completion of electrophoresis, gel is immersed in 0.1% coomasie Blue R250 in methanol: acetic acid: water (4:1:5) with gentle shaking and is then destained in destaining solution (20% methanol and 10% glacial acetic acid) till the background becomes clear.

5. Immuno-assay of Western blotted proteins: Western blotting of the proteins from E. coli carrying plasmid encloded intracellular streptokinase is carried as detailed (Towbin, H., Stachelin, T., Gordon, T., 1979, Proc. Natl. Acid. Sci. 76: 4350). The cultures are grown to 600 nm of 0.5–0.6, and are induced with 1–5 mM IPTG. The cells are centrifuged. The pellet is resuspended in cell lysis buffer and the supernatant obtained after high-speed centrifugation. These fractions are resolved on the 10% SDS-PAGE. The gel is equilibrated with the transfer cell buffer (25 mM Tris, 175 mM glycine in 20% methanol) and is blotted electrophoretically on to the nitrocellulose membrane at 50 V for 3 h. The blot is blocked with 5% skimmed milk (Difco) in PBS (Phosphate buffer saline) for 14–16 h at 4° C. The blot is further washed with 0.1% Tween-20 in PBS. The blot is incubated with the anti-SK antibodies (raised against pure S. equisimilis SK in rabbit) in 40 ml of PBS containing 5% skimmed milk for 3 h at room temperature with gentle shaking. The blot is washed with 0.1% Tween 20 in PBS three times for 15 minutes each. Again it is blocked with PBS-skimmed milk for 15 min with gentle shaking at room temperature and further incubated with peroxidase-conjugated goat anti-rabbit immunoglobulins at a dilution of 1:5000 in 20 ml of PBS-skimmed milk (5%) for two 2 h at room temperature with gentle shaking. The filter is again washed with 0.1% Tween 20 in PBS for three times (15 min each). The colour reaction for HRP-linked secondary antibodies is carried out by immersing the blot in 10 ml of reaction buffer solution having 10 mg of DAB (di-amino benzdine) and imidazole each. The reaction is terminated by washing with distilled water.

6. Streptokinase assay using chromogenic peptide substrate: plasminogen activator activity of streptokinase is assayed according to Jackson, K. W., Esmon, N., Tang, T., 1981, Methods in Enzymology 80: 387. One hundred ul of appropriately diluted streptokinase samples, 25 ul of sample buffer (0.15 M Tris-Cl buffer, pH 7.5) and 15 ul of human plasminogen solution (0.5 mg/ml in 0.05 M Tri-Cl, pH 7.5) are mixed together. The tubes are incubated at 37° C. for 15 min, after which 18 ul of NaCl (1.77 M in 0.0.32 M Tris-Cl, pH 7.5) is added. The amount of plasmin generated in the first stage is measured by further addition of 12 ul of plasmin-specific chromogenic substrate, Chromozyme-PL (Boebringer-Mannheim, Germany), 5 mg/ml in water, and the tubes are again incubated at 37° C. for 10 min. After this incubation, 0.4 ml acetic acid (0.2 M) is added to terminate the reaction. The release of yellow-colored 4-nitroaniline is monitored at 405 nm spetrophotometerically. Appropriate dilutions of S. equisimilis streptokinase obtained from WHO, Hertfordshire, U.K. is used as a reference standard for calibration of international units in the unknown preparation. Protein concentration is estimated according to the method of Bradford, M. M., 1976, Anal. Biochem. 72: 248) using BSA as a standard. Bradford's reagent (Biorad Inc., USA) is utilized according to the manufacture's instructions. For estimating the concentration, protein-samples in phosphate buffer are made to 800 ul. To this, 200 ul Bradfor's reagent is added and is mixed thoroughly. The reaction is maintained at room temperature for 5 min and absorbance at 595 nm is monitored. The specific activity for PG activation (I.U./mg protein) of an unknown preparation of SK or SK-FBD is thus determined from the SK assay and protein estimation data.

7. Fibrin clot massy for SK: This test is performed to determine the clot lysis ability of any thrombolytic drug, such as streptokinase, urokinase or tissue plasminogen activator, and is adapted from British Pharmacopia (1980 edition).

Reagents: (i) 100 mM citrate phosphate buffer, pH 7.1 containing 0.8% BSA (referred to as buffer-1). (ii) Bovine fibrinogen (Cohn Fraction-I, obtained from Sigma Chemical Co., St. Louis, USA), 2.5 mg/ml prepared in buffer-1. (iii) Bovine thrombin (obtained from Sigma as a lyophilized powder). Stock solution of SK, 500 I.U./ml, prepared in sterile water and stored in aliquots of 50 ul each at −70° C. Before use, one aliquot is thawed and diluted to 50 I.U./ml in buffer-1. (iv) Human plasminogen (Boehringer Mannheim, Germany) stock 1 mg/ml, prepared in sterile water. Stored in aliquots of 100 ul each at −70° C. (v) Standard SK (from W.H.O., obtained from Dr. P.J. Gaffney, Division of Haematology, N.I.B.S.C., Blanche Lane, Pottes Bar, Hertfordshire, EN 6 3QG, U.K.). The standard SK vial is composed of 700 international units of SK (in lyophilized form alongwith stabilizers). A complete vial should be dissolved in 700 ul of sterile dist. water to obtain a concentration of 1000 I.U./ml. The dissolution should be carried out either at 4° C. or by keeping all the solutions on ice. The dissolved SK is then aliquoted into convenient sizes and stored at −70° C. Prior to carrying out clot lysis assay an aliquot of 1000 I.U./ml (stock) is thawed and diluted further in cold buffer-1 on ice. Dilutions (A to D, below) are prepared serially in the following way using a new pipette tip for each transfer.

A. 10 ul of stock+990 ul of buffer-1=10 I.U./ml.
B. 500 ul of A+500 ul of buffer-1=5 I.U./ml.
C. 500 ul of B+500 ul of buffer-1=2.5 I.U./ml.
D. 500 ul of C+500 ul of buffer-1=1.25 I.U./ml.
(All dilutions are tempered at 37° C. prior to use in the clot test as are the other solutions to be used).

Two hundred ul of each dilution is used in the clot lysis reaction mixture. One unit of SK (present in 200 ul of SK dilution B) is just sufficient to lyse a standard fibrin clot in approximately 5 min at 37° C.

Clot lysis test protocol: (a) Preparation of clot (negative control): During each step, the contents of the tube are gently mixed.

Step 1: add 450 ul of buffer-1 to a small glass tube (0.8 mm internal diameter).
Step 2: add 50 ul of bovine thrombin (50 I.U./ml) solution to the tube.
Step 3: add 100 ul of 1 mg/ml plasminogen to the solution in tube.
Step 4: add 400 ul of 2.5 mg/ml fibrinogen to the solution in tube.

Immediately after step 4, the tube is kept at 37° C. in a water bath without shaking. A standard clot forms within 30–40 seconds. The I.U./ml in the unknown is determined in a similar manner after appropriate dilution.

B) Clot lysis with thrombolytic agent (SK): When clot lysis is to be performed using standard SK, all the steps i.e. 1, 2 and 3 are carried out as described above, except that at step 1, only 250 uL of buffer-1 is added. Also, at step 4, 200 ul from the appropriate dilution of SK containing 1–2 units (as described under Reagents, above) is premixed with 400 ul of fibrinogen solution in a separate eppendorf tube, and rapidly equilibrated to 37° C. in water bath. This mixture is then added to the clotting reaction at step 4, described above. The tube is then incubated as previously. A clot is formed in the same or lesser time as above, but is now followed by its lysis. The time for complete lysis is noted down using a stop watch. The time for lysis depends upon the amount of SK used in the mixture. Lysis time by a particular unit of standard SK (i.e. lysis time of 5 min by 1 I.U. of SK) is taken as a standard. The unknown preparation of SK should be diluted appropriately to obtain a lysis time of approximately 5 min, which can then be used to calculate the units of SK present in that unknown preparation.

8. Kinetic assays for determining the HPG activation by SK or SK-FBD chimeras: A one-stage assay method (Shi. G. Y., Chang B. I., Chen. S. M., Wu, D. H. and Wu, H. L., 1994, *Biochem. J.* 304:235. Wu, H. L., Shi, G. Y., and Bender, M. L., 1987, *Proc. Natl. Acad. Sci.* 84: 8292. Wohl. R. C., Summaria, L., and Robbins, K. C., 1980, *J. Biol. Chem.* 255:2005) was used to measure the activation of HPG by SK or SK-FBDs. Varying concentrations of either SK or SK-FBD chimeric protein (10 nM–200 nM) were added to 100 ul-volume micro-cuvette containing 1 uM of HPG in assay buffer (50 mM Tris-Cl buffer, pH 7.5, containing 0.5 mM chromogenic substrate and 0.1 M NaCl). The protein aliquots were added after addition of all other components into the cuvette and bring the spectrophotometric absorbance to zero. The change in absorbance at 405 nm was then measured as a function of time in a Shimadzu UV-160 model spectrophotometer.

9. Assay for determining the steady-state kinetic constants for HPG activator activity of SK and SK-FBD constructs: To determine the kinetic parameters for HPG activation, fixed amounts of SK or SK-FBD(4–5), 1 nM, were added to the assay buffer containing various concentrations of HPG (ranging from 0.035 to 2.0 uM) in the 100 uL assay cuvette as described above. The change in absorbance was then measured spectrophotometrically at 405 nm for a period of 30–40 min at 22° C. The kinetic parameters for HPG activation were then calculated from inverse, Michaelis-Menton, plots by standard methods (Wohl, R. C., Summaria, L., and Robbins, K. C., 1980, *J. Biol. Chem.* 255:2005).

10. Radioactive fibrin clot preparation: 50 uL ul of (2.5 mg/ml) cold fibrinogen was mixed with 50 ul ($9\times10^5$ cpm) of $^{125}$I-labelled fibrinogen (specific activity $8\times10^5$ cpm/ug of fibrinogen) and added to the mixture of 1.1 uM HPG and 0.25 units of human/bovine thrombin in 0.1 M citrate phosphate buffer, pH 7.5 containing 0.8 percent BSA in a total volume of 1 ml in a glass tube (1.3×12 cm). The clot was formed by incubating the mixture at 37° C. for 2 min. The clot was then washed thrice with 2 ml of TNT buffer (50 mM Tris-Cl buffer, pH 7.5. containing 38 mM NaCl and 0.01 percent Tween-80) for 2 min at 37° C. As required the non-radioactive fibrin clots were prepared by omitting $^{125}$I-labelled fibrinogen from the clotting mixture.

11. Clot lysis in the presence of human plasma: $^{125}$I-fibrin clot lysis was carried out in the presence of 2 ml citrated human plasma containing different concentrations of either SK or SK-FN (ranging from 100 to 200 nM at 37° C. The reaction tubes rotated slowly at 37° C. and 0.1 ml aliquots were removed at regular intervals to measure the soluble $^{125}$I-fibrin degradation products by measuring the amount of radioactivity released using a gamma counter. The total radioactivity of each clot was determined by measuring the radioactivity of the respective tube before taking out any aliquots.

12. Clot lysis in the presence of human fibrinogen: $^{125}$I-fibrin clot lysis was also carried out in the presence of various concentrations of human fibrinogen (ranging from 1 to 4 mg/ml) containing 100 nM of either SK or SK-FN. Clot lysis was also performed in the presence of fixed fibrinogen concentration (2 mg/ml) and different concentrations of SK or SK-FBD protein construct (ranging from 50 to 200 nM). The rations were incubated at 37° C. with gentle shaking and the release of $^{125}$I-fibrin degradation products as a function of time was measured as described previously.

EXAMPLES

Example 1

High Level Intracellular Expression of Biologically Streptokinase in E. coli.

In order to express native-like, full-length S. equisimilis strain H46A Streptokinase intracellularly in E. coli the SK-encoding polynucleotide block was transferred from the plasmid vector construct pJKD-55 by digesting with Nco I and Sal I restriction enzymes (R.E.) which liberated the SK open-reading-frame (ORF). Plasmid pJKD-55 contained the streptokinase gene which was isolated from Streptococcus sp. (ATCC 12449), also referred to conventionally in the scientific literature S. equisimilis strain H46A, by known procedures earlier reported for the molecular cloning of SK gene and its expression in heterologous hosts such as E. coli (Malke, H. and Ferretti, J. J., 1984, Proc. Nat'l Acad. Sci. 81: 3557; Pratap, J., Kaur, J., Rajamohan, G., Singh, D., and Dikshit, K. L., 1996; Biochem. Biophys. Res. Commun. 227: 303). The latter publication describes the procedures by which the SK gene was cloned in E. coli plasmids, such as pJKD-8 and pJKD-55 used herein. (see below).

Figure 8:
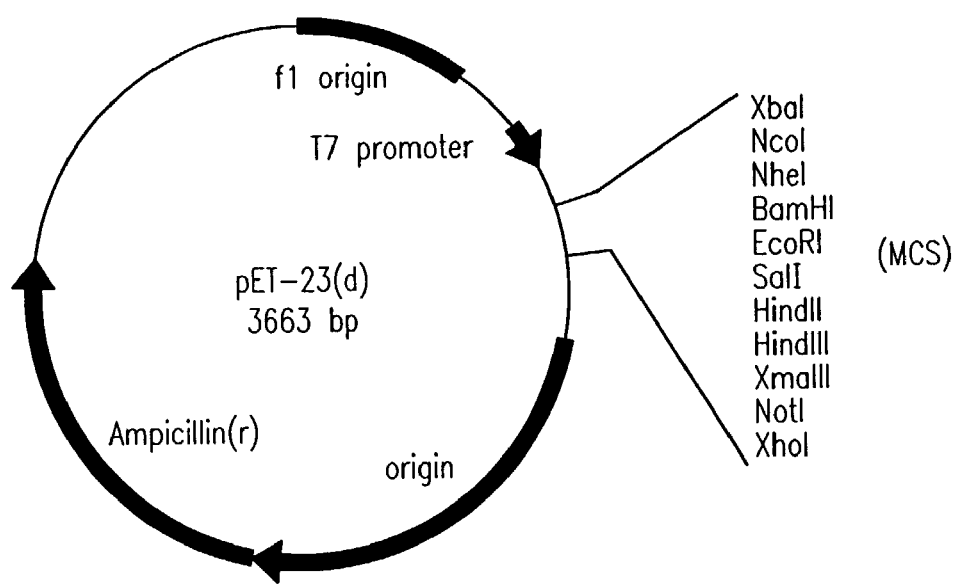
FIG. 8. Map of plasmid pET23(d).
Figure 9:
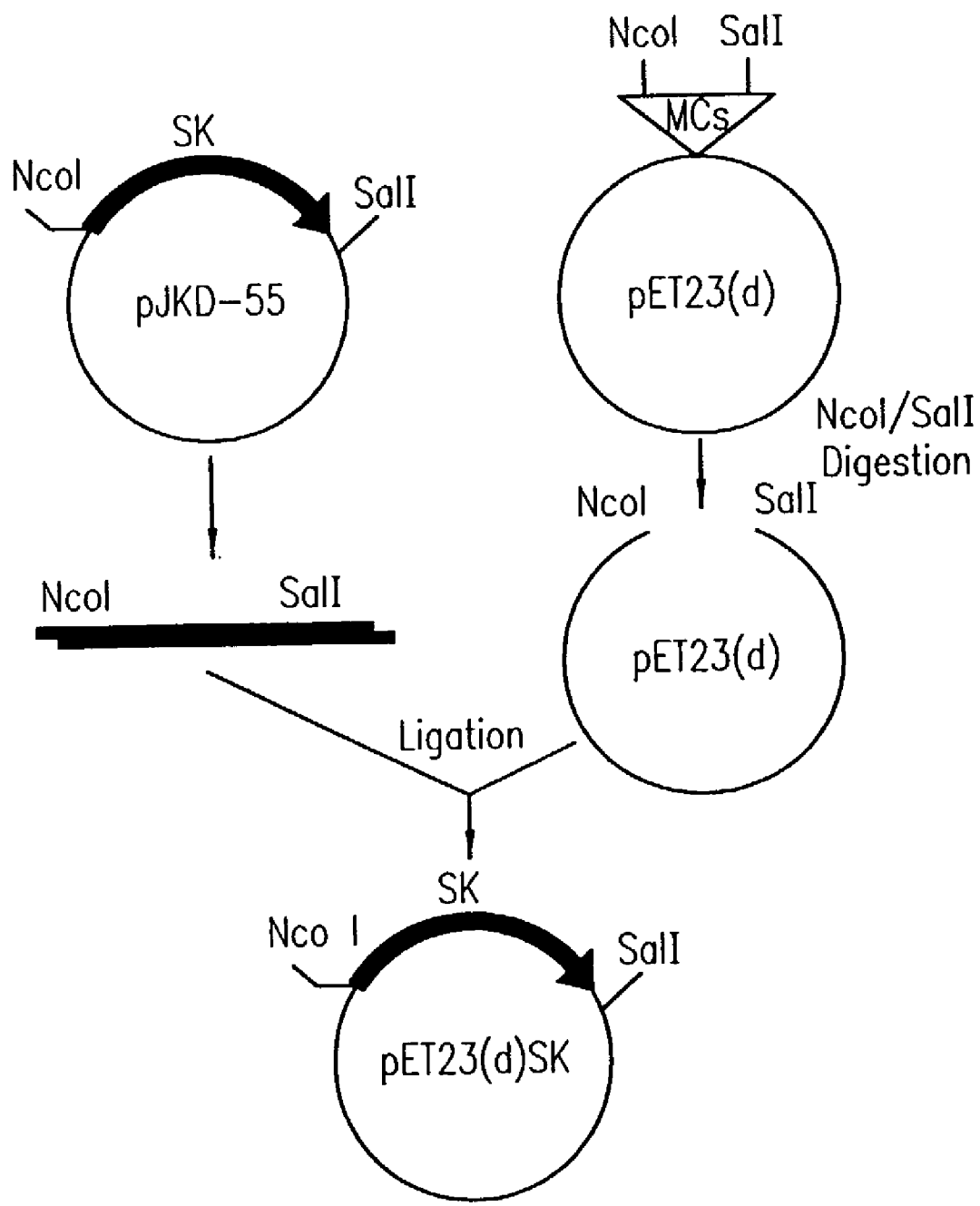
FIG. 9. Flow chart schematically depicting the main steps in the construction of a plasmid vector for the expression of the native SK gene of *S. equisimilis* H46A.

The DNA segment liberated from pJKD-55 by R.E. digestion was then cloned into plasmid pET-23(d) (see FIG. 8 for map of this plasmid) which had also been treated with the same enzymes (Nco I and Sal I) to obtain cohesive ends compatible with those of the SK gene (see FIG. 9 for the scheme used for this purpose). This vector contained an initiation codon in-frame with the Nco I site of pET-23(d). Upon ligation, the SK open-reading-frame could be recreated, but one modified at the N-terminal end, together with an additional ATG at the 5' end emanating from the re-formed Nco I site.

Figure 10:
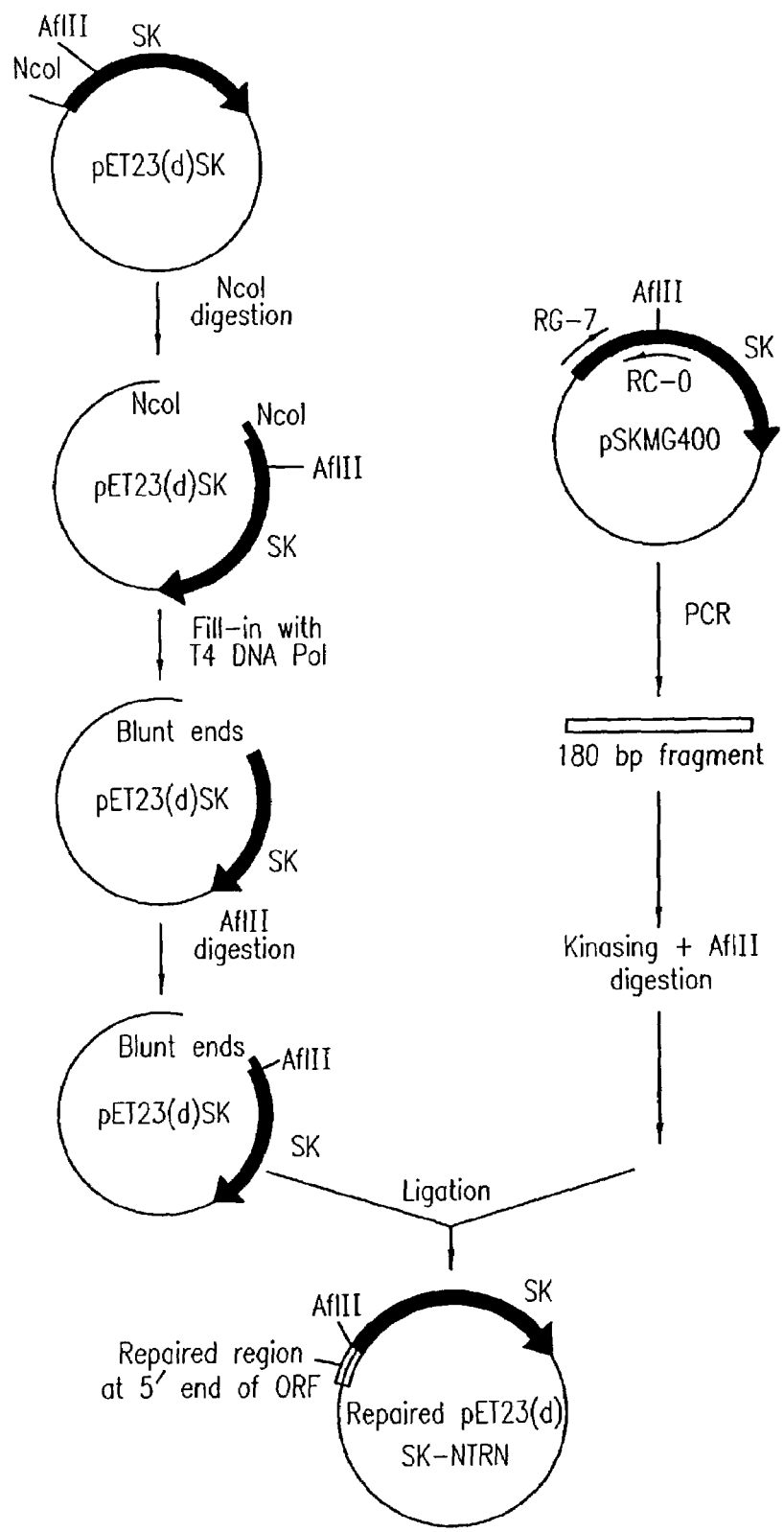
FIG. 10. Flow diagram schematically depicting the main steps involved in the repair of the vector pET23(d)SK i.e construction of expression vector pET23(d)SK-NTRN (NTRN: abbrev. form for N-terminally repaired with native sequence).

The construction of pET23(d)-SK was carried out as follows. Approx. 3 ug each of pET23(d) and pJKD-55 plasmid DNAs were digested (separately) with 20 units each of Sal I (37° C. for 6 h), followed by 15 units each of Nco I in 20 ul reactions at 37° C. for 10 h. After stopping the reactions by heat treatment (65° C., 10 min), followed by phenol-chloroform extraction and ethanol precipitation of the DNA, the digests ware run electrophoretically on a 1.2% agarose gel to isolate the needed DNA fragments i.e. insert, carrying the SK gene from pJKD-55, and the linearized vector pET23(d) [see FIG. 9]. The respective fragments were purified from the gels using the Prep-A-Gene DNA purification kit of BioRad Inc., CA, USA. The insert and double-digested, linearized vector DNAs were then ligated at an approx. 3:1 molar ratio (~350 ng of vector and 400 ng of the insert liberated from pJKD55) in a 20-uL reaction using standard ligation conditions at 16° C. for 12 h. After this duration, the ligase was heat inactivated (60° C., 15 min) and one-fifth of the ligation reaction was directly used to transform E. coli XL-Blue electrocompetent cells using the following electroporation conditions with 2 mm internal diameter electroporation cuvettes (obtained from BioRad Inc., Richmond, Calif., USA): voltage, 2.5 KV, resistance, 200 Ohms, and capacitance 25 uF. Six transformants were picked up from Amp-LB plates on which the transformed cells were plated a various dilutions. Individual colonies were inoculated into 10 ml LB-Amp media to prepare plasmid DNA by standard methods. The isolated plasmids were then screened electrophoretically on the basis of molecular size to identify the positive clone/s. All six clones were positive by this criterion. In order to express full-length SK containing all of the amino acid residues of mature S. equisimilis SK (FIG. 3), the native N-terminal was repaired using a synthetic "cassette" approach (refer to FIG. 10 for the scheme followed for the repair of the SK gene). The portion of the repaired SK gene at the 5' end in pET23(d)SK was obtained through PCR using the primers RG-6 and RG-7 with the following sequence ad target specificity.

RG-7 (Forward Pprimer)
5'-ATT GCT GGA CCT GAG TGG CT-3' (SEQ ID NO:25) (specific for the first seven codons of the SK gene; Cf FIG. 11)

RG-6 (Reverse Pprimer) 5'-TGG TTT TGA TTT TGG ACT-3' (SEQ ID NO:26) (specific for codons 57–62 of SK gene)

The PCR was carried out using as the template, plasmid pSKMG-400, which contained the DNA sequences coding for full-length native SK of Streptococcus sp. (ATCC 12449), also referred to as S. equisimilis H46A as described earlier. This plasmid was constructed by cloning the Nco I-Sal I fragment obtained from pJKD-55 followed by T4 DNA polymerase-catalyzed fill-in of the two ends (to obtain blunt ends) and cloning at the Eco RV site of plasmid BlueScript KS$^-$ (Stratagene Inc., Wis. USA). The two PCR primers were designed to amplify the N-terminal portion of the native SK gene upto a unique restriction site in the gene which could be utilized for recloning the amplified PCR product back into pEET23(d)-SK for expression of protein. Moreover, the 5'end of the RG-7 primer started with ATT, coding for Ile, the first residue of the mature SK-encoding DNA (or gene), so that the PCR-amplified SK-encoding polynucleotide DNA segment could dock in-frame with the nucleotides ATG, formed at the NcoI-cut and refilled end of the expression vector, thus juxtaposing the initiation codon in-frame for the repaired SK ORF. The following PCR conditions were used for the amplification reaction (100 uL total): approx. 10 ng pSKMG-400 as template, 20 pmol each of the RG-6 and RG-7 primers, 1 ul (2.5 units) of pfu DNA polymerase (Stratagene Inc.), 200 uM of each dNTP's, 10 uL of the standard buffer (10× conc. provided by the Stratagene Inc.). The following cycling parameters were used; 'hot start' for 5 minutes at 92° C., denaturation at 92° C. for 1 min, annealing at 50° C. for 1 min and extension at 72 ° C. for 1 min. A total number of 30 cycles, and a final extension of 10 min at 72° C. for allow the completion of any of the incomplete amplified products, were provide. The PCR showed a single band of 160 bp as evidenced by electrophoresis on a 1.2% agarose gel. For cloning the PCR product into pET23(d)-SK vector, approx. 10 ug pET23(d)-SK vector was digested 25 units of NcoI restriction enzyme in a 100 ul reaction using the buffer NEB-4) supplied by New England Biolabs, Inc., and by incubating at 37° C. for 6 h. The completion of NcoI digestion was checked by loading 5 ul of the reaction mixture on a 0.7% agarose gel. After confirming the digestion, the NcoI site was filled-in (i.e. made blunt ended) using T4 DNA polymerase in the presence of all four dNTPs in a 85-ul reaction as follows. Seventy five ul of above-mentioned NcoI digestion mixture was supplemented with 4 ul DTT (100 mM stock), 4 ul dNTP's from a dNTP stock (2 mM), and 2000 Weiss units of T4 DNA polymerase. The reaction was incubated at 37° C. for 1 h after which it was stopped by adding EDTA (10 mM final conc.) and heating at 75° C. for 10 min. The DNA was then ethanol-precipitated. The precipitated DNA was dissolved in 40 ul TE and was digested with Afl II restriction enzyme in a 60-ul reaction at appropriate reaction conditions as recommended by the supplier. Separately, 40 ul of the PCR-amplified DNA reaction, prepared using pSKMG-400 vector as substrate to supplement the deleted portion of the SK gene, was also digested with Afl II restriction enzyme, followed by running on low melting agarose gel (1%) to separate the vector and insert DNA pieces [the insert contained a blunt end, and an Afl II-site compatible cohesive terminus at the other end, thus making it suitable for facile ligation with the vector, which had been similarly treated with NcoI, followed by a fill-in reaction with T4 DNA polymerase to obtain a blunt end, followed by a digestion with Afl II]. The required pieces of DNA were isolated from the electrophoresis gels as small agar blocks after visualization under trans-illuminated UV radiation, and were purified from the agarose by beta-agarase enzyme. One unit of beta-agarase per 100 ul of agarose gel approximately in the 1× beta-agarose buffer (New England Biolabs Inc.) was employed to digest the agarose and to purify the DNA according to the protocol recommended by the supplier (New England Biolabs Inc., USA). The purified DNAs were quantitated and vector and insert were ligated m a 1:5 molar ratio in a 20 ul reaction, carried out at 16° C. for approx. 18 h. For the ligation reaction, 2 ul of 10×ligase buffer, 1 ul of 10 mM rATP stock, and 2000 Weiss units of T4 DNA ligase were use. The DNA the ligation mixture was precipitated with n-butanol, and used directly to transform electrocompetent *E. coli* XL-Blue cells. The transformation mixture was plated on LB-Amp plates. The positive clones (repaired pET23(d)-SK) were screened from the wild-type background on the basis of Nco I digestion (the insertion of the PCR amplified segment in the vector would result in the loss of the Nco I site). Two of the clones (pETSK-NTRN, for 'N-terminally repaired, native') obtained after this screening were further confirmed using Sanger's method of nucleotide sequencing, which showed complete fidelity with the known fill-length native sequence of the *S. equisimilis* SK-encoding DNA (Cf. FIG. 11) except the presence of an extra ATG codon at the 5'-end of the ORF, and no mutation/alteration at the upstream promoter regions or downsteam sequences in the plasmid could be observed DNA from these confirmed clones were then transformed into *E. coli* BI-21 strain, and expression of intracellular SK in liquid culture was examined after induction wit IPTG according to the protocol described earlier, essentially by analyses of cell-lysates on SDS-PAGE. However, no band corresponding to standard SK was visible on SDS-PAGE. The possibility of the presence of low levels of SK was then checked by Western Blotting analysis of the lysates as it is a more sensitive method when compared to a direct examination of the SDS-PAGE gels by Coomasie staining. In this case, indeed, a faint band corresponding to the position of standard SK on the Western blots could be clearly discerned, which showed that the levels of expression of the native SK gene were poor.

Figure 12A:
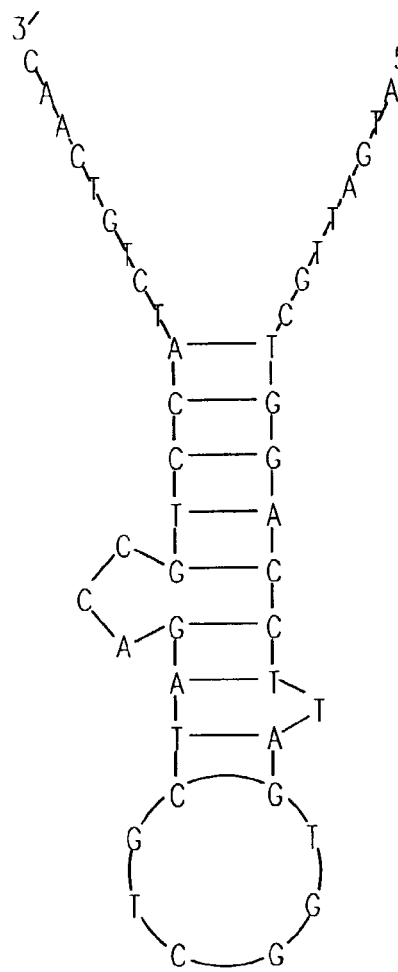
FIG. 12. Predicted secondary structure of native (A) and translationally silently modified (B) 5'-ends of the SK gene sequence (SEQ ID NOs:27 and 28, respectively).
Figure 12B:
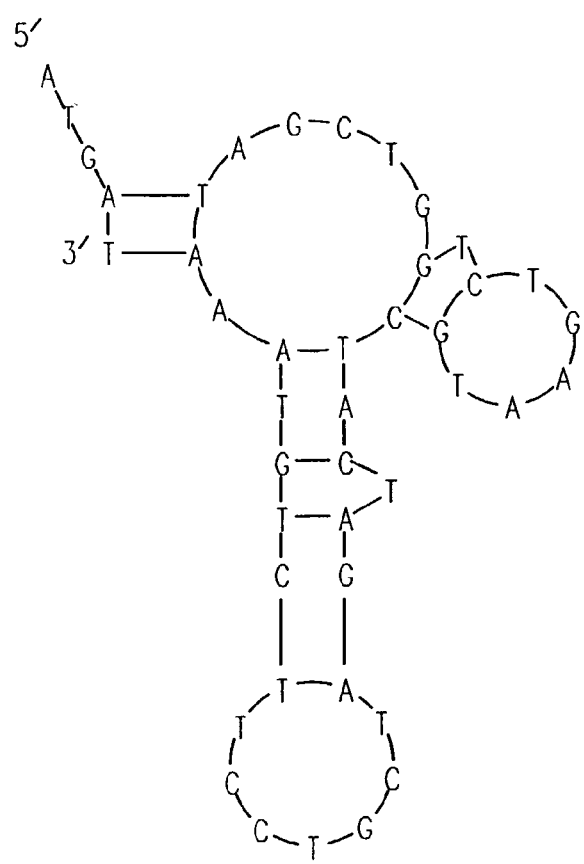

The possibility that the sequences in the native SK-encoding DNA polynucleotide block corresponding to the N-terminal residues could be forming strong secondary structure/s in the encoded mRNA transcripts that might be hindering the expression was examined through computer-assisted analysis using the program DNASIS (version 5.0). This unambiguously demonstrated that the potential for forming highly stable secondary structure by the N-terminal end of the SK gene was appreciably Strong (free energy approximately −10 Kcal/mol; see FIG. 12A). Translationally silent mutagenesis of the. gene at its 5' end was then carried out to disrupt and/or reduce this secondary structure by replacement of GC rich codons (that are more likely to promote secondary structure-formation in the mRNA transcript) with AT-rich codons, wherever possible. Through this procedure several sequence/s, altered specifically at the 5' end and possessing lowered stability (−6 to −5 Kcal/mol) as compared to that of the native sequence, were obtained. One of these sequences, that resulted in maximal al destabilisation of structure-forming potential, to approx. −5 Kcal/mole (FIG. 12B), was chosen for the expression studies.

The preparation of an expression vector containing a full-length, SK-encoding polynucleotide segment but one with a modified (i.e. non-native.) DNA sequence at its 5'-end with less structure-forming potential was carried out as shown schematically in FIG. 13 using a combination of synthetic DNA cassette incorporation and PCR-based strategy. The alternate sequence to be incorporated at 5'-end of the SK gene was provided through two homologous synthetic oligonucleotides (SC-I and SC-II, complementary to each other except for overhangs at the end), whose sequence is shown below. Also indicated in bold type are the altered nucleotides which resulted in a lowering of structure forming potential in the 5'-end of the SK gene.

```
SC-I                                                                  (SEQ ID NO:13)
5'-C ATG ATA GCT GGT CCT GAA TGG CTA CTA GAT CGT CCT TCT GTA AAT AAC AGC C-3'
(Partial NcoI site)

SC-II                                                                 (SEQ ID NO:14)
5'-AA TTG GCT GTT ATT TAC AGA AGG ACG ATC TAG TAG CCA TTC AGG ACC AGC TAT-3'
(Partial MfeI site)
```

These carried two new restriction sites (NcoI and MfeI), introduced by silent mutagenesis using the computer program GMAP (Cf. Raghava and Sahni,. 1994., *BioTechniques* 16: 1116–1123) without altering the amino acid sequence encoded by this segment of DNA so as to facilitate the cloning of the repaired SK-encoding DNA into the expression vector, pET23(d)-SK (see FIG. 13 for the overall cloning scheme for reconstruction of the N-terminal region of *S. equisimilis* SK-encoding DNA). The alterations were carried out in two stages, as depicted schematically in FIG. 14. In Stage I, a translationally silent restriction site (Mfe I) was engineered close to the N-terminal end of the SK gene (overlapping codon numbers 17 and 18 in the native SK sequence; see FIG. 3) since no unique site close to the N-terminal end was available for incorporating a synthetic DNA piece for purposes of altering this region in the plasmid. An upstream PCR prier (termed 'Mfe I primer') incorporating this potential Mfe I site (underlined in the sequence of the primer) was synthesized with the following sequence.

Mfe I primer: 5'-C-AGC-CAA-TTG-GTT-GTT-AGC-GTT-GCT-3' (SEQ ID NO:15)

A synthetic oligonucleotide containing an Afl II site (termed RG-6, which has been described before) was used as the downstream primer.

These two primers were utilized for the amplification of the SK sequences encoding the N-terminal region using pfu DNA polymerase. The following reaction conditions and cycling parameters were used. Pfu polymerase buffer (Stratgene Inc.), 200 uM each of the dNTP's, MfeI and RG-6 primers: 20 pmol each, pET23(d)-SK vector as template (2 ng), Pfu polymerase 1 ul (2.5 units), total reaction volume 100 ul. A 'hot start' was given for 5 min at 95° C., followed by denaturation for 1 min at 95° C., annealing for 1 min at 45° C., and extension for 1 min at 72° C. A final extension at 72° C. for 10 min was also incorporated in the program. As expected from theoretical considerations, a 141-bp long SK region was amplified. The PCR product was phenol-chloroform purified and precipitated using isopropanol after adjusting the salt concentration to 0.3 M with 3 M NaOAC. The precipitated product was dissolved in 25 ul sterile dist. water and kinased in a 30-ul reaction, after adding 3 ul Multicore buffer (Promega Inc., WI. USA), 1 ul (10 units) of T4 PNK (Promega) and 1 ul rATP (10 mM stock). The reaction mixture was incubated at 37° C. for 2 h and then stopped by heat-inactivating at 65° C. for 20 min, and the DNA purified using phenol-chloroform and precipitated with 2 volumes of isopropanol. The pBluescript II KS(-) vector was digested with EcoRV restriction enzyme and then dephosphorylated using CIAP using a standard protocol. Both the kinased PCR product and dephorphorylated pBluescript II vector were quantitated by $A_{260}$ measurements in a 100-uL cuvette, and the vector and insert DNAs were ligated in 1:10 molar ratio of vector:insert by taking 590 ng vector and 280 ng insert in a 20 ul reaction after adding appropriate amount of ligase enzyme (approx. 500 Weiss units) and ligase buffer containing rATP. The ligation reaction was incubated at 16° C. overnight. The ligation mixture was heat inactivated (65° C., 30 min), the DNA was butanol-precipitated, and approx. one-fifth electroporated into E. coli XL-Blue electrocompetent cells. The transformants were screened by plating them on LB-Amp plates. Ten transformants were picked up and inoculated for minipreparation of plasmid DNA. The minipreps were then digested with MfeI and AflII enzymes sequentially to identify the positive clones containing the 141 bp insert. Unmodified pBluescript was kept as control. All the transformants were found to be positive by this criterion. This construct was labelled as p(MfeI-AflII)-SK.

Stage-II: The oligos SC-I and SC-II in equimolar amounts (approx. 270 ng each) in 25 uL were annealed by cooling their mixture from 80° C. to room temperature slowly. Approximately 5 ug of pET 23(d)SK and 10 ug p(MfeI-AflII)-SK vectors were digested with Afl II/Nco I and MfeI/AflII, respectively, for vector and insert preparations. Twenty five units each of MfeI and AflII were used for vector preparation and 50 units were used for insert preparation. The enzymes were added in two shots of 12.5 units and 25 units in each of the reactions. The pET23(d)-SK vector was digested in a 60 ul reaction, and p(MfeI-AflII)SK was digested in a 100-ul reaction. The pET23(d)-SK digestion mixture was run on a 1% low melting agarose gel for vector preparation and the p(MfeI-AflII) SK digestion mixture was run on a 2% agarose gel for isolating the 115 bp insert. Both the vectors and insert bands were cut out from the agarose gel and were purified using beta-agarase and quantitated. Then, a mixture of Nco I and Afl II digested pET23(d)-SK vector, annealed SC-I and SC-II oligos, and Mfe I-Afl II insert of p(Mef I-Afl II)-SK vector were ligated in a 3-piece ligation reaction in a 1:7:5 molar ratio in a 20 ul reaction (see FIG. 13). In the actual reaction, approx. 660 ng of the vector, 92 ng of the insert and 60 ng of the annealed oligos were taken. The mixture was ligated by adding 2000 Weiss units of ligase into the reaction. The reaction was incubated at 16° C. overnight. The ligation mixture was n-butanol-precipitated, dried, redissolved in 10 uL TE and approx. one-third used to transform E. coli XL-1 Blue electrocompetent cells. The transformants were screened on LB-Amp plates. Ten transformants were picked and inoculated for preparation of minipreps. All the minipreps alongwith pET23(d)-SK as control were digested with Nco I enzyme to search for the positive clones. Only one clone, as well as pET23(d)-SK, gave digestion with Nco I which indicated that the remaining 9 clones were positive for the desired construct. One of the clones was then completely sequenced by automated DNA sequencing using Sanger's dideoxy method, which showed that the N-terminal region was now full-length i.e. encoded the native SK sequence plus a N-terminal methionine, containing exactly the sequence expected on the basis of the designed primers, SC-I and SC-II with the altered codons at the 5' end compatible with potential for secondary structure reduction in the mRNA transcripts (see FIG. 14). In addition, the DNA sequencing established that no other mutation was inadvertently introduced in the SK ORF in during the reconstruction protocol. This plasmid vector-construct, termed as pET23(d) SK-NTR (N-terminally reconstructed) has been deposited in the Microbial Type Culture Collection, Chandigarh, India (MTCC) with the accession No. BPL 0017. The plasmid DNA from this clone was then transformed into E. coli BL-21 DE3 strain for expression studies. The E. coli BL-21 cells were grown in liquid culture and induced with 2 mM IPTG at an $OD_{600}$ of ~0.6 for the induction of SK, as detailed earlier. The cells were then pelleted by centrifugation and lysed in SDS-PAGE sample buffer and analysed electrophoretically by SDS-PAGE an 10% acrylamide gel. It was observed that the level of SK (47 kD band) was approx. 25–30 percent of the total soluble proteins, a substantial increase compared to the very low expression observed in the case of the construct with the native N-terminus (pET 23(d)-SK-NTRN).

Example 2

Harvesting of Intracellularly Expressed SK from E. coli, Purification of SK Protein, and Characterisation of Highly Pure and Biologically Active SK.

Glycerol stocks of E. coli BL-21 strain harbouring plasmid pET23(d)SK-NTR, maintained at −70° C., were used to prepare a seed culture by inoculating freshly thawed glycerol stock (approx. 100 uL) into 100 ml of LB medium (in 500 ml conical flask), containing 50 ug/ml of ampicillin. The flask was incubated at 37° C. with shaking on a rotary shaker at 200 r.p.m for 16 h. This culture was used to seed four 2 L Erlenmeyer flasks each containing 500 ml of the same medium (LB-Amp) using 5% (v/v) of inoculum. The flasks were incubated at 37° C. with shaking (200 r.p.m.) for a duration till the absorbance at 600 nm had reached 0.5 –0.6 (~2 h after inoculation). At this time, IPTG was added to the cultures to a final conc. of 2 mM and incubation, as before, continued for a further 3 h. The cultures were then chilled on ice and processed for the next step immediately. The cells from the culture media were harvested by spinning them down by centrifugation at 6000×g in a GS-3 rotor (Servall)

for 30 min at 4° C. The supernatants were discarded and the combine cell-pellets carefully resuspended by vortexing in 65 ml of lysis buffer containing a chaotropic agent for effecting release of the cellular contents. The composition of the cell lysis buffer was as follows (final concentrations are given): 6 M guanidine hydrochloride and 20 mM sodium phosphate buffer, pH 7.2.

The E. coli cell suspension was shaken gently on a rotary shaker at 4° C. for 1 h to effect complete cell lysis. The lysate was then subjected to centrifugation at 4° C. for 15 min at 9000 r.p.m. The clear supernatant (containing approx. 300 mg total protein as determined by Bradford method) was then processed further, as follows (all subsequent steps were conducted at 4° C., and all buffers and other solutions used were also maintained at 4° C.). The supernatant was diluted 6-fold in which the conc. of Gdn.HCl was 1 M; simultaneously, aliquots of a stock solution (0.5 M) of sodium phosphate buffer, pH 7.2, and NaCl (stock conc. 5 M) were added to obtain 20 mM and 0.5 M with respect to sodium phosphate and NaCl, respectively, in the diluted cell lysate supernatant (final volume 200 ml). The mixture was gently swirled for a few minutes, and then loaded onto a 100 ml bed volume (4 cm internal diameter) axial glass column for hydrophobic interaction chromatography (HIC) on phenyl-agarose-6 XL (Affinity Chromatography Ltd., Isle of Man, U.K.) coupled with an automated liquid chromatography work-station (model Biocad Sprint, Perseptive Biosystems, MA, USA) capable of continuous monitoring of effluents at two wavelengths simultaneously, and formation of pre-defined gradients for elution. The column was pre-equilibrated with 0.5 M NaCl in 20 mM sodium phosphate buffer, pH 7.2 (running buffer) onto which the bacterial cell lysate was loaded at a flow rate of 85 ml/h. The flow-through was collected, and the column washed with running buffer (400 ml total) at the same flow rate, followed by the same volume of running buffer devoid of NaCl (washing steps). The SK was then eluted with dist. water (pH 7.0) at a slower flow rate (35 ml/h). All the effluents were collected in fractions (25 ml each) and the SK activity as well as protein content in each fraction was determined. Virtually all of the loaded SK activity was found to bind to the column, less than 5% of that total activity being found in the flow-through and washing. Approximately 85–90% of the-loaded SK activity was recovered at the dist. water elution step. SDS-PAGE analysis showed the presence of a predominant band of 47 kD migrating alongwith native SK (purified from S. equisimilis H46A) run as standard. The SDS-PAGE as well as the activity analysis showed the SK to be 85–90% pure at this stage when compared to the unpurified cell lysate. The SK in the dist. water elute was then made 20 mM in sodium phosphate, pH 7.2 (running buffer) and loaded at a flow rate of approximately 300 ml/h onto DEAE-Sepharase Fast Flow (Pharmacia, Uppsala, Sweden) packed in a 1.6×20 cm axial glass column pre-equilibrated with the running buffer. The column was then washed with 200 ml of the same buffer, following which it was developed with a NaCl gradient (0–0.6 M). in running buffer (pH 7.2). All eluates from the column were saved with an automated fraction collector. Ten-ml fractions were collected, and SK activity as well as protein was estimated in each. Aliquots from each faction were also analysed by SDS-PAGE to examined the relative purity of the eluted protein. The flow-through and washings were essentially devoid of SK activity, but approximately 80–85% of the loaded SK activity eluted at around 0.35 M NaCl in the gradient as a single symmetrical peak (containing a total of 42 mg protein). The specific activity of this protein was $1.1 \times 10^5$ I.U./mg. On SDS-PACE, it showed a single band co-migrating with standard natural S. equisimilis SK. A densitometric analysis of the SDS-PAGE gels revealed that the background protein/s in the final purified SK represented less than 2% of the total Coommassie stainable content. The overall SK recovery with the purification process was found to be approx. 65 percent.

The purified recombinant SK expressed in E. coli was characterized physico-chemically by several other criteria in order to compare it with natural SK. By the clot lysis procedure, it showed a specific activity of 105,000 IU/mg, under conditions where natural SK from S. equisimilis strain H46A was found to have a specific activity of 110,000 IU/mg protein. Upon reverse phase high performance liquid chromatography (RP-HPLC) on C-18 columns, both SK types were indistinguishable, showing the presence of a single symmetrical peak at the same position when eluted with a gradient of gradually increasing ACN concentration. By UV spectroscopy, the recombinant SK was found to be identical to the natural SK. The N-terminal amino acid sequence of rSK was found to be identical with that of natural SK, except for the presence of an extra methionine residue at the N-terminus (the sequencing was carried out for 25 cycles).

Example 3

Construction of a hybrid DNA polynucleotide between SK-encoding DNA and fibrin being domains 4 and 5 encoding DNA of human fibronectin, its expression in E. coli, oxidative refolding, and purification of biologically active chimeric protein.

Figure 15:
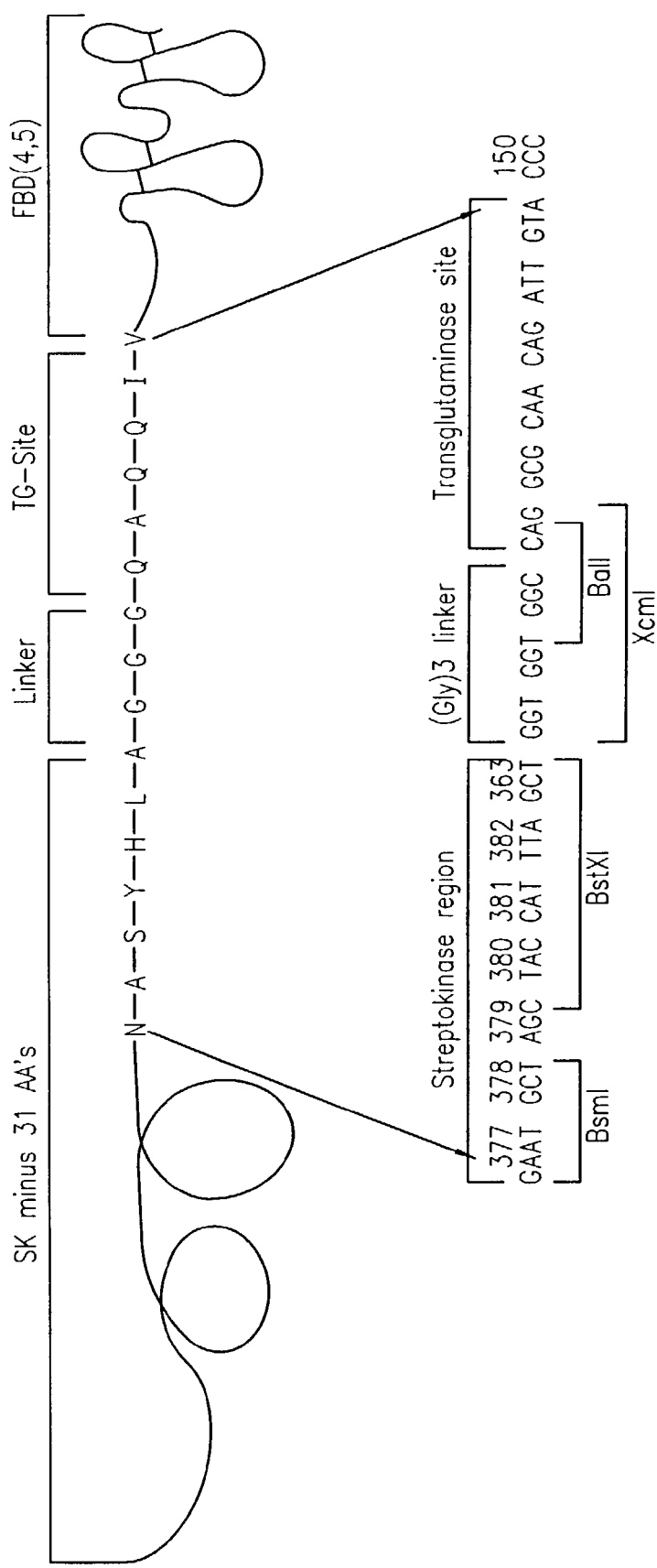
FIG. 15. Schematic depiction of the intergenic region of the chimeric SK-FBD(4,5) gene (above: SEQ ID NO:8; below: SEQ ID NO:7) highlighting the design of a gly-gly-gly sequence, a transglutaminases cross-linking site and several unique restriction enzyme sites wherein different inter-genic cassettes can be conveniently swapped into this region. Also shown is the location of the natural Bsm I site in the SK gene which was exploited as the common junction point for joining the FBD sequences to the SK gene.
Figure 16:
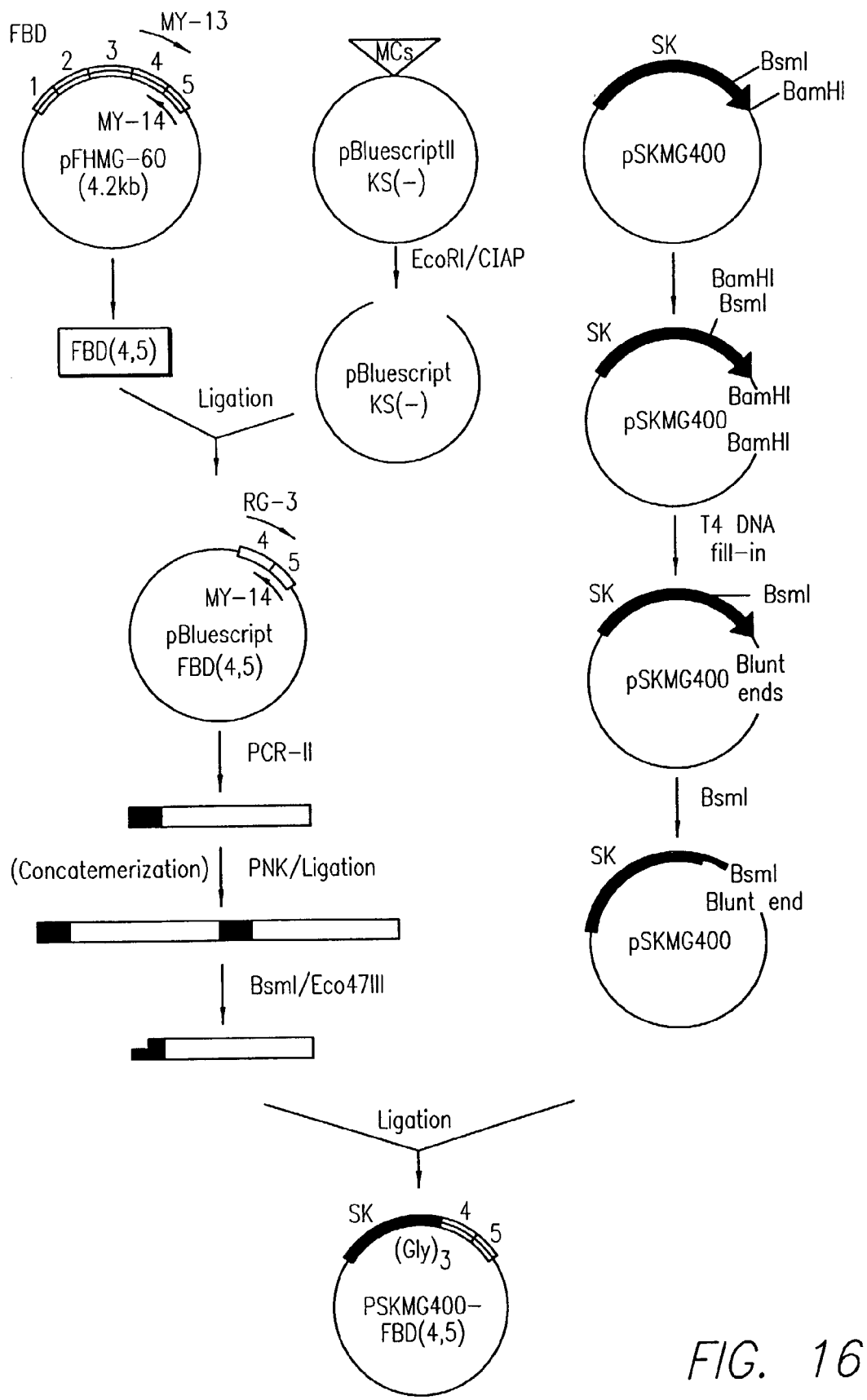
FIG. 16, Flow diagram depicting the main steps in the constriction of plasmid pSKMG400 containing the SK-FBD (4,5) hybrid DNA block composed of FBD(4,5) sequences linked to the intergenic sequences at its 5'-end, and the SK gene fused in-frame at the 3' end.

The scheme followed for the construction and expression of a chimeric (hybrid) polynucleotide DNA block formed between the DNA encoding for residues 1 to 383 of SK followed by in-frame joining to the DNA coding for the FBD 4 and 5 of human fibronectin is shown in FIG. 16. A short linker DNA segments coding for 3 glycine residues, in tandem, between the two polynucleotide-segments was incorporated into the design (termed 'intergenic sequence') (see FIG. 15) so as to provide flexibility to the expressed chimeric polypeptide product. In addition, a new terminator codon was introduced at the end of the FBD(4,5) DNA so that the hybrid ORF encoded for a polypeptide ending after the two FBDs. Thus, the design essentially had the following configuration: SK[residues 1–383]-(gly-gly-gly)-[FBS(4, 5)]. In addition, a tranglutaminase recognition site was also engineered in the gene-design directly after the intergenic sequence so that the expressed, hybrid protein could become covalently cross-linked to the fibrin strands of the clot(FIG. 15). A two-stage PCR-based experimental strategy (FIG. 16) was employed to construct the hybrid polynucleotide. A polynucleotide-block containing the sequence coding for domains 4 and 5 was first selectively amplified using the plasmid pFHMG-60 as template. The latter contained the DNA encoding for all five human FBDs (FIG. 16). This amplification reaction (PCR-I) was carried out with specifically designed forward and reverse primers with the following sequences.

```
Forward primer (MY 13):                                              (SEQ ID NO:16)
5'-CCG GAA TTC GCG CAA CAG ATT GTA CCC ATA GCT GAG AAG TGT TTT GA-3'
        Eco R1  TransglutaMINASE-        hybridizes to upstream FBD(4,5) sequences
                recognition sequence Reverse primer (MY 14):                                              (SEQ ID NO:17)
5'-GGC CTT AAG AGC GCT CTA ACG AAC ATC GGT GAA GGG GCG TCT A-3'
   'clamp' Afl II Eco 47 III stop    hybridizes to downstream FBD(4,5) sequences
                        codon
```

Note:—In the above primer sequences, the 5'-non-hybridising sequences (bold) as well as the hybridizing ones, towards the 3'-ends of the primers that are complementary to selected segments of fibronectin FBD(4,5)-encoding, DNA sequences are shown. In the 5'-non-hybridizing ends were also incorporated new R. E. sites by 'silent' mutagenesis, a The sequence of primer RG-3 is given below highlighting features incorporated in its design (bold letters denote non-hybridizing segments towards the 5'-end of the primer to distinguish these from the sequence complementary with respect to template DNA).

```
                                                                     (SEQ ID NO:18)
        5'-G AAT GCT AGC TAC CAT TTA GCT GGT GGT GGC CAG GCG CAA CAG ATT GTA CCC-3'
           Bsm I      Bst X              Xcm I Bal I   segment hybridlizing with the
           (hybridizes to SK gene at                    5'-end of DNA block from PCR-1
           codons 376-383)                   (-gly-gly-gly-)  at the TG recognition site
``` tranglutaminase(TG)-encoding site and/or stop codon sequences, as indicated above (underlined). The start of the hybridizing sequences in primer MY-13 correspond to the beginning of the sense strand sequence of FBD(4,5), namely residue 150,onwards (refer to FIG. 6 for the amino acid and DNA sequences of the fibrin binding domains of human fibronectin). In case of primer MY-14, the beginning of the hybridizing sequence (antisense) correspond exactly to the codon for residue 259 of human fibronectin (Cf. FIG. 6). The 'clamp' mentioned in the figure refers to the extra nucleotides added at the 5' end of a primer to facilitate the digestion at the nearby R.E. site which, otherwise, is poorly digested when present at or near the end of a DNA fragment generated by PCR.

Figure 4:
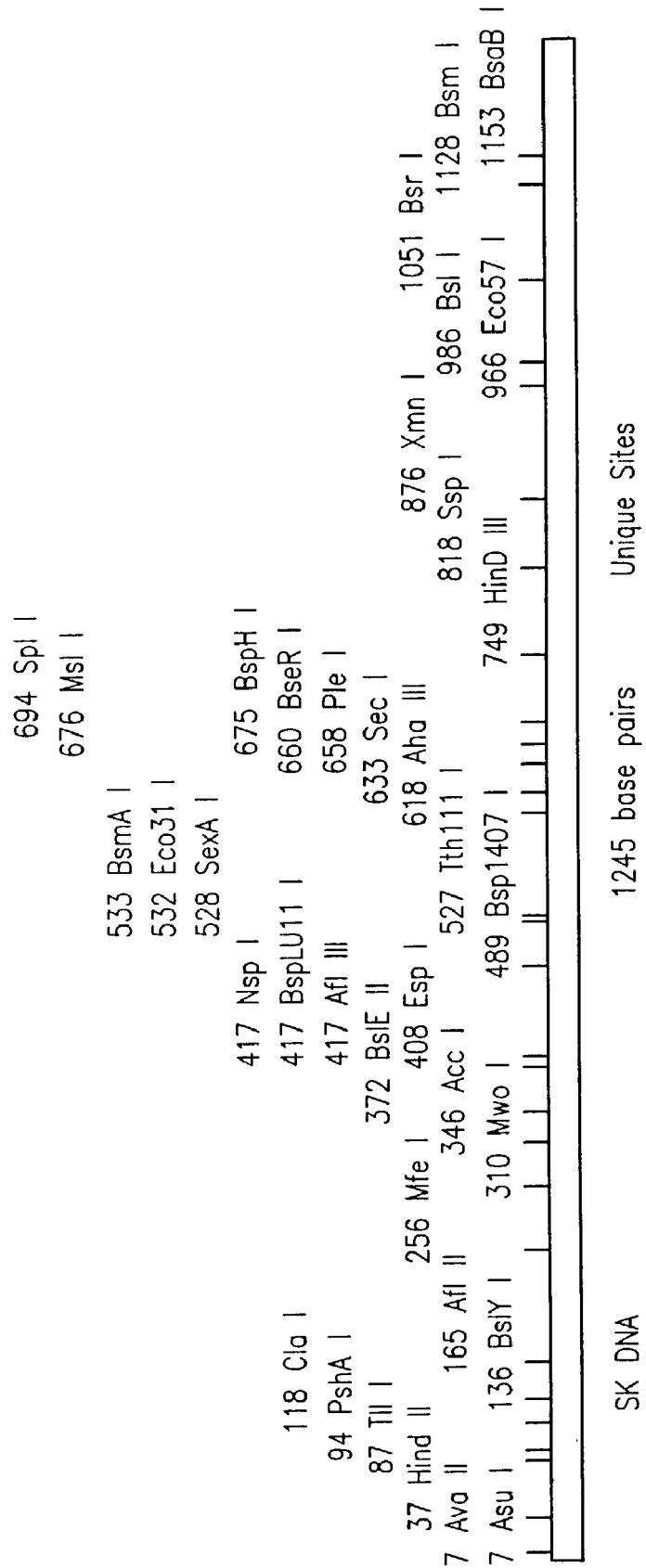
FIG. 4. Partial restriction enzyme map of *S. equisimilis* H46A DNA encoding for SK.

As described above, the forward primer contained a segment at its 3' end that was homologous with the 5' end of the DNA encoding for the FBD(4,5) sequences, and also contained a 5' (nonhybridizing) segment that encoded for a TG-recognition site as well as RE sites to facilitate the cloning of the PCR product in a plasmid vector. This plasmid, containing the FBD(4,5) gene-block and additional 5' sequences was then employed as template for a second PCR (PCR-II) using a set of primers (RG-3 and MY-14). Primer RG-3 was designed so as to contain the other desired elements of the intergenic segment viz., the codons for the gly-gly-gly residues, as well as those encoding for a small segment of SK (see FIGS. 15 and 16) directly after a unique R.E. site (Bsm I) present naturally in the C-terminal region of the native SK ORF (approximately overlapping the codons 377 and 378 of the *S. equisimilis* SK open-reading-frame; Cf. FIGS. 3 and 4). This site was chosen as the common, junction-point between the two polynucleotide blocks (i.e. SK and FBD) to be integrated. Additionally, unique restriction sites flanking the intergenic (i.e. in and around the -gly-gly-gly-) sequences were also designed into the upstream primer through translationally silent mutagenesis that could be exploited to substitute alternate oligonucleotide cassettes at the intergenic region of the hybrid polynucleotide that would provide altered flexibility and/or rigidity characteristics in the expressed polypeptide different from that provided by the (gly)$_3$ linker (Cf. FIG. 15).

The amplified DNA obtained from PCR-II using primers RG-3 and MY-14 was treated with Bsm I to "dock" it at the Bsm I site in the SK ORF in vector pSKMG400 at one end, and with Eco 47 III (which produces blunt-ends) to facilitate blunt-end cloning at the filled-in Bam HI site present after the SK open-reading-frame (ORF) in the plasmid vector (FIG. 16).

The follow reaction conditions and PCR parameters were used. PCR-I (final reaction conditions in a 100-uL reaction); 20 pmol of each of the MY-13 and MY-14 primers, pFHMG-60 vector as template (1 ng), 200 uM each of the dNTP's, Pfu polymerase 1 ul (2.5 units). Pfu polymerase was added at 94° C. i.e. a hot start for 5 min was given to avoid non-specific amplification. The following cycling conditions were employed: denaturation at 92° C. for 45 seconds, followed by annealing at 60° C. for 1 min, and extension at 72° C. for 1 min. A total number of 30 cycles were given, followed by a final extension for 10 min at 72° C. The reaction yielded a single 360 bp PCR product as seen on a 2% agarose gel alongwith standard PCR markers. The amplified product was then cloned into pBluescript II KS⁻ at the EcoRI site (refer to FIG. 16) which bad been introduced in the PCR product as a 5'-overhang. The PCR reaction mixture was purified using standard methods, and then kinased with T4 PNK enzyme. The kinased PCR product was ligated to concatamarize the PCR product in order to internalize the EcoRI site to facilitate cloning of the DNA using the procedure of Jung et al. (Jung, V., Pestka, S. B., and Pestka S., 1990, *Nucl. Acids Res.* 18:6156). The ligated DNA mixture was then digested with EcoRI followed by electrophoresis on a 2% agarose gel to check the efficiency of the ligation and digestion steps. The band representing EcoRI-digested PCR product was cut out from the gel and purified. Approximately 400 ng of the PCR product was ligated with 1 ug of pBluescriptII (KS⁻) pre-digested with EcoRI and the dephosporylated. Approximately 2 ul of the ligation mixture was directly used to transform *E coli* DH 5-alpha electrocompetent cells. The transformants were selected on LB-Amp plates containing IPTG and X-gal using blue and white colony selection. Ten white transformants were picked and taken up for minipreparation of plasmid. The plasmid DNAs were digested with EcoRI enzyme, and the digests analysed on 1.5% agarose gels. The transformants releasing 360-bp insert (the size of the PCR product) were taken as positive clones. Nine of the ten clones were found to be positive by this criterion. One of the above clones was then confirmed for the absence of any unexpected mutations by automated DNA sequencing by Sanger's procedure, and used as template for PCR-II employing RG-3 and MY-14 as primers so as to add additional sequences at the 5' end of amplified FBD sequences in the cloned PCR-I product. The PCR-I had resulted in the addition of a TG recognition size and a stop codon onto die original FBD(4,5) gene-block, whereas the stage-II PCR was carried out to effect the addition of the poly-glycine linker and overlapping SK sequences onto the FBD(4,5) gene-block. The following reaction conditions and cycling parameters were used for carrying out PCR-II. Each of the dNTP's: 200 uM, PCR-I product cloned in pBluescript II (KS⁻) as template (linearized) 260 ng, RG-3 and MY-14 as forward and reverse primers (100 pmol each), 5% DMSO (v/v), 1 ul Taq DNA polymerase (2.5 units) in a total reaction-volume of 100 ul. Cycling parameters were similar to that of PCR-I except that the annealing temperature was lowered to 58° C. An aliquot (approx. one-tenth) of the PCR-II was run on a 1.5% agarose gel to check for amplification. As the Taq polymerase does not produce blunt ended PCR products (unlike pfu polymerase) but ones with a single-base overhangs (reference), the PCR product was first filled-in, and then kinased. These two modifications carried out in a single reaction at 22° C. for 30 min using 10 units each of the T4 DNA polymerase and T4 PNK (total volume 85 ul). In addition, 8 nmol dNTP's as well as 1 mmol rATP were added to the reaction (all indicated conconcentrations are final). The reaction was stopped by adding EDTA to 10 mM followed by heating tube at 70° C. for 10 min. The filled and kinased PCR product was subjected to a phenol-chloroform treatment and precipitated with two volumes of ethanol in the presence of 0.3 M sodium acetate. The pellet was redissolved in 20 ul of dist. water. Approx. 15 ul of this DNA was ligated in order to concatemarize the PCR product. For doing the ligation, 1× Universal Buffer (supplied by Stratagene Inc.), 1 ul (of a 10 mM rATP stock) and 400 weiss units of T4 DNA ligase were added to a 2.5 ul reaction. The reaction was incubated at 16° C. overnight. The ligase was heat-inactivated at 65° C. for 10 min. The concatamerized PCR product was then first digested with Eco47 III (approx. 20 units) in a 25 ul reaction at 37° C. for 6 h and then the DNA was digested with BsmI enzyme at 65° C. for 6 h after adding ~20 units of BsmI enzyme in the same reaction. In parallel, the vector pSKMG400 (approx. 4 ug), containing the SK gene, was digested with BamHI enzyme according to standard protocol and the digested DNA was filled-in using T4 DNA polymerase in the presence of 100 uM dNTP's and 0.5 mM DTT. The reaction was incubated at 37° C. for 1 h. The reaction was stopped by heating tube at 75° C. for 10 min. Then the BamHI filled vector was digested with BsmI enzyme by incubating at 65° C. for 6 h. The vector was purified by a phenol-chloroform treatment followed by a chloroform-isoamyl extraction, followed by ethanol precipitation of the DNA. Then the Eco47III and BsmI double-digested PCR product and BamHI-digested aid filled-in plus BsmI-digested pSKMG-400 vector were ligated (refer to FIG. 16) in a 20-ul reaction by incubating at 16° C. for 14 h, after which the ligase was inactivated by heat at 70° C. for 10 min and then the DNA was precipitated with n-butanol. It was then used to transform *E. coli* XL-Blue electrocompetent cells. The transformed colonies were then selected on LB-Amp plates. Ten transformants were picked and screened for the presence of the diagnostic test, namely the release of a 372-bp fragment after digestion with NotI and BamI enzymes, in contrast to a 295-bp fragment from the control plasmid, pSKMG400 since the positive clones contained the additional FBD(4,5) segment. Eight clones from the ten selected turned out to be positive by this criterion. The positive clones were designated as pSKMG400-FBD(4,5). One of these was subjected to DNA sequencing which confirmed the presence of the expected sequence at the 5'-end, and a complete absence of any other mutation jin the rest of the gene-block.

Figure 17A:
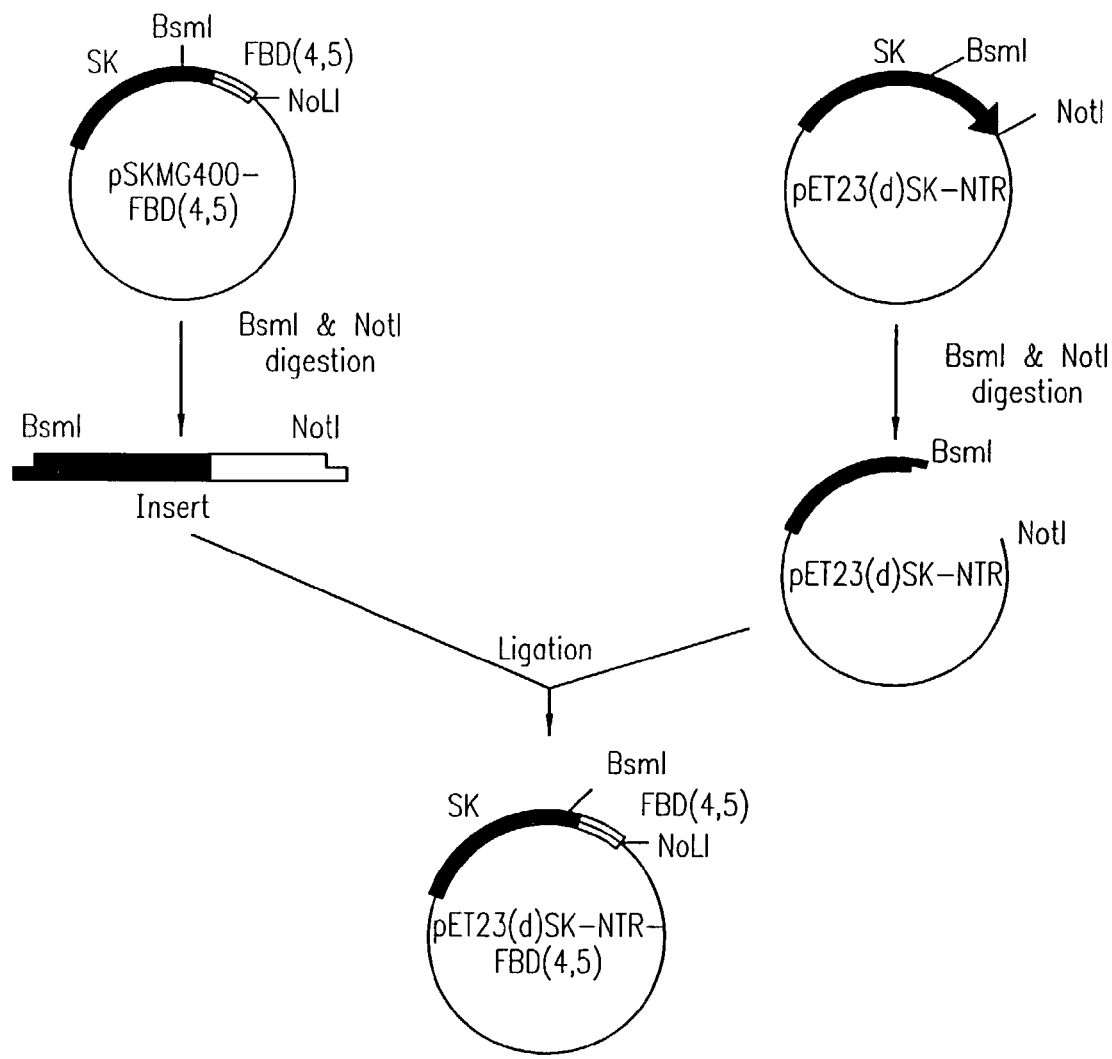
FIG. 17a. Scheme depicting the cloning of the hybrid SK-FBD(4,5) cassette into pET23(d)SK-NTR for intracellular expression of SK-FBD(4,5) chimeric protein in, E. coli.

For the expression of the SK-FBD(4,5) hybrid polynucleotide DNA intracellularly in *E coli*, the scheme shown in FIG. 17a was followed. The BsmI-NotI DNA piece from pSKMG400-FBD4-5 [beginning from that encoding for the C-terminal portion of the SK gene and carrying the intergenic linker region, the FBD(4,5) segments, and ending after the stop codon for this ORF at the Not I site originating from the multiple cloning site (MCS) of the parent vector] was transferred into plasmid pET23(d)SK-NTR digested with the same restriction enzymes. The digested vector and the DNA segment from pSKMG400-FBD(4,5) (insert) were isolated from 1% agarose gels after beta-agarase digestion, as described earlier, The vector and insert DNA then ligated by standard procedures using a vector; insert molar ratio of 1:5 (approximately 590 ng of the BsmI/NotI double-digested vector and 250 ng of the BsmI/NotI double-digested insert in a 20-ul reaction). DNA from the ligation reaction was butanol precipitated and directly used to transform *E. coli* XL-1 Blue electro-competent cells. Transformants were selected on LB-Amp plates. Ten transformants were picked up and taken up for plasmid minipreparation. The miniprep DNAs were digested with BsmI and NotI enzymes, alongwith pSKMG400-FBD(4,5) as control. Three clones gave BsmI/NotI insert equal in size to that of the insert liberated from pSKMC400-FBD(4,5). One of the clone, designated pET23(d)SK-NTR-FBD(4,5) and deposited with MTCC with accession No. BPL 0014, was then fully sequenced by automated DNA sequencing in and around the SK insert (see FIG. 17b for the gene sequence). All the 3 positive clones were transformed into *E. coli* BL-21 stain and were induced for the expression of SK-FBD(4,5) hybrid protein using the standard protocol described before. The *E. coli* BL-21 cells harboring the plasmid pET-SK-FBD(4,5) were induced with 2 mM IPTG at ~0.60D$_{600}$ and were further incubated for 3 h at 37° C. In parallel, cultures were also grown where IPTG addition was omitted (uninduced controls). Cells from 1.5 ml of the cultures were pelleted down by centrifugation and were directly lysed in 100 ul SDS-PAGE sample buffer. After high-speed centrifugation (8000 g×20 min) to pellet undissolved components, approx. 25 ul of the supernatant of each of the samples (alongwith lysate from pET23(d) SK-NTR, as positive control) was loaded onto 10% SDS-PAGE gel and subjected to electrophoretic analysis. The gels showed distinct bands of 57 kD in he IPTG-induced cultures (roughly representing 20–25% of the total Commassie-stained protein bands in the gel), indicating that the hybrid SK-FBD(4,5) fusion protein had been expressed at high levels. In the case of pET23(d)SK-NTP, harboring cultures, a band corresponding to 47 kD, the position of native SK, was observed. In parallel, SDS-PAGE gels were subjected to the plasminogen-overlay procedure, which showed distinct zones of clearance by the 57 kD hybrid protein, however, these zones were produced with a distinctly slower rate in comparison to those produced by native SK or the rSK expressed in intracellularly from pET23(d)SK-NTR.

Ten ml of LB-Amp media were inoculated with E. coli B321 cells harboring pET-SK-FN (4,5) and incubated at 37° C. for 12 h with shield (200 r.p.m.). This inoculum was used to seed 200 ml of LB-Amp medium, and incubated for 2 h at 37° C. with shaking. At this time, the $OD_{600}$ of the culture was approx. 0.600. The production of SK-FBD(4,5) protein in this culture was then induced by the addition IPTG to 2 mM, and incubation continued for another 3 h at 37° C. with shaking. The $OD_{600}$ had reached 1.2 by this time. The cell were harvested by centrifugation (8000 g×20 min) at 4° C., washed once with, ST buffer, and resuspended in approx 14 ml of the same buffer over ice. This cell suspension was then subjected to sonication in the cold (20 sec pulses with 20 sec. gaps; total time 15 min). The lysate so obtained was then centrifuged (10000 g×30 m) at 4° C. The supernatant was carefully decanted into a separate flask. This solution contained approx. 6 mg/ml protein as estimated by Bradford's method using BSA as standard, and had a total of $1.5 \times 10^4$ I.U of SK activity as measured by the chromogenic peptide procedure (see description of methods, given above). The lysate was then split into two portions of ~6 ml each to effect either air oxidation or glutathione-mediated oxidation of the SK-FBD(4,5) polypeptide. For the air oxidation, the 6 ml lysate was diluted to a total of 40 ml of solution (reaction mixture A) which contained (final concentrations): Tris-HCl (pH 7.5), 50 mM and NaCl, 150 mM. In reaction B (reoxidation using the reduced-oxidized glutathione buffer), the final volume was also 40 ml, but it also contained [besides NaCl (150 mM) and Tris-Cl (50 mM)], a mixture of GSSG and GSH (1:10 molar ratio, with GSH at 10 mM) and EDTA (1 mM), Both reactions were subjected to gentle mixing at room temperature (24 plus/minus 2° C.) for 10 min and then passed through two separate glass columns each containing 6 ml human fibrin-Sepharose at a flow rate of 20 ml/h in a recycled mode i.e. the effluent was passaged back into the column with the use of a peristaltic pump. After 18 h of passage through the respective columns, the flow of the reaction mixtures was terminated. Each column was then washed with 50 ml of binding buffer (50 mM Tris-HCl, pH 7.5, and 150 mM NaCl) followed by 50 ml each of 2 M urea (in binding buffer), followed by 6 M urea in the same buffer (to effect tightly bound protein). All washings were collected in 10 ml fraction with a fraction collector, and analyzed for protein by Bradford's method, as well as SK activity using chromogenic substrate and human plasminogen as substrates was also determined for each fraction. The total yield of protein in the 6 M urea washings was 280 ug in the case of reaction A (air oxidation), and 380 ug in case of Reaction B (GSG-GSSH mediated refolding). These two pools represented, respectively, the fibrin-binding SK-FBD(4,5) protein obtained after air oxidation or glutathione-catalyzed refolding of the intracellular protein expressed from the plasmidpET23(d)SK-FBD(4,5). The specific activity of both the fibrin-Sepharose binding protein fractions from Reaction A and B were found to be almost identical ($2.5 \times 10^4$ IU/mg and $2.1 \times 10^4$ I.U./mg, respectively). The dilute protein fraction were concentrated approx. 10-fold with centrifugation in Sartorius centristart filters. The concentrated fractions were then analyzed by SDS-PAGE, with and without reduction with beta-mercaptoethanol. On reducing SDS-PAGE (i.e. with beta-mercaptoethanol treatment of the samples), the reoxidized-refolded SK-(FN4,5), irrespective of the method of reoxidations, showed a single predominant band, but one with higher MW (~57 kD) as compared to the native SK standard (47 kD) as expected on the basis of the chimeric design of the hybrid gene. Essentially the same patterns were obtained when the SDS-PAGE was conducted without beta-mercaptoethanol, a treatment wherein any of the cystine disulfide (S—S) bridges would not be reduced to cystine —SH groups. This indicated that the refolded molecules contained essentially monomeric intra-molecular S—S bonds, and contained negligible quantities of higher molecular weight (i.e. polymeric) products formed due to inter-molecular S—S bridge formation between the SK (FN4,5) molecules as a result of the rexodiation step. When analyzed by the Ellman DTNB color reaction for thiol groups (Habeeb, A.F.S.A., 1972., Method in Enzymol. 25:457., Academic Press, New York) these fractions showed the complete absence of any free —SH group, indicating that the oxidation of the original 8 cysteines present in the reduced form of the chimeric polypeptides, to S—S bridges, was complete as a result of the reoxidation/refolding step.

Example 4

Construction of a Hybrid DNA Polynucleotide Between DNA Encoding for SK and FBD Pair 1 and 2, and Cloning and Expression of the Chimeric Polypeptide in E. coli.

Figure 18:
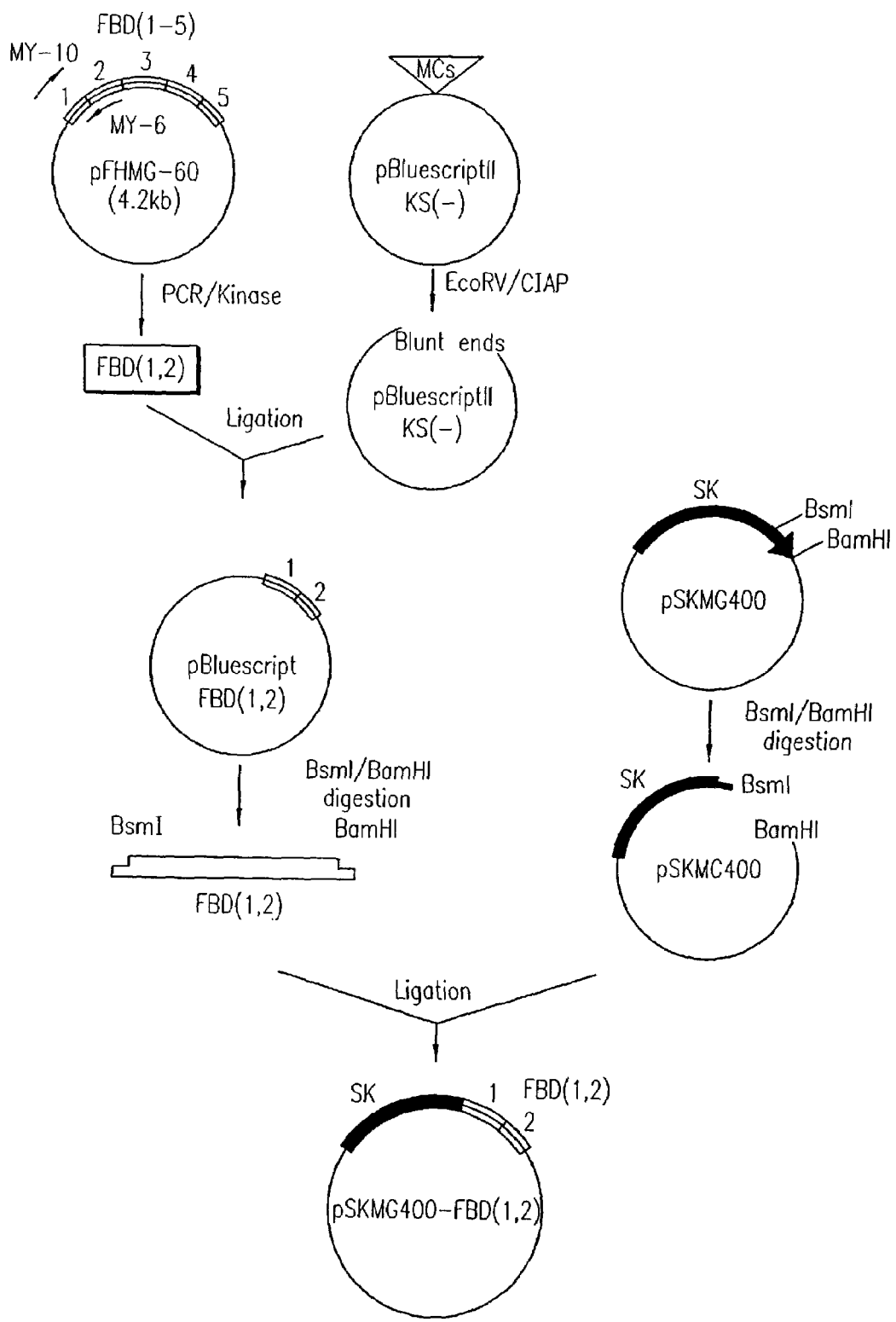
FIG. 18. Schematic flow diagram for cloning of SK-FBD (1,2) hybrid gene in pBluescript, to obtain [pSKMG400-FBD(1,2)].

The construction of a hybrid between SK and FBD pair 1 and 2-encoding polynucleotide DNA in the same translational frame involved a strategy closely similar to that utilized for hybrid construction between SK- and FBD pair 4 and 5 -encoding polynucleotide DNAs (FIG. 18). The essential 'units' used in both the constructs were similar i.e., DNA encoding residues 1 to 383 of SK, a short polynucleotide sequence encoding for polyglycine linker between the two DNA polynucleotide blocks, and a tranglutaminase (TG) recognition site for cross-linking, removal of the stop codon of the SK gene and introduction of a new stop codon at the end of the FBD segments [either FBD(4,5) or FBD (1,2) etc]. This strategy also exploited the use of the Bsm I site of the SK gene as a common junction-point for the fusion between the SK and FBD(1,2) polynucleotide segments. However, the strategy differed from that employed for constructing SK-FBD(4,5) fusion in that the amplification of the FBD (1,2) domains was carried out in one stage, unlike that of SK-FBD(4,5) wherein two consequetive PCRs with differing :5'-primers were utilized (Example 3). This was because in case of the SK-FBD(1,2) construct, a very large primer was not required as a TG recognition site is naturally present in the FN gene just at the beginning of the FBD-1 domain (Cf. FIG. 6), thereby obviating the need to engineer a TG site in the upstream primer.

The FBD pair (1,2) was amplified from the plasmid pFHMG-60 (containing all five of the FBD encoding sequences of human fibronectin) with the following two primers whose sequences are provided below. Also shown are the 5'-ends containing non-hybridizing sequences (in bold letters) and the incorporated RE sites therein to facilitate cloning and/or docking into the SK gene; the areas hybridizing with the target DNA sequences in the templates are also underlined.

```
Upstream primer, MY-10                                                          (SEQ ID NO:19)
                    SK sequence (codons 377-383; Cf.Fig. 3)
5'-G-TAC-GGA-TCC G-AAT-GCT-AGC-TAT-CAT-TTA-GCG-GGT-GGT-GGT-CAGGCG-CAG-CAA-ATG-GTT-3'
   Bam HI    Bam I                       (gly-gly-gly-)    hybrdizes at the TG-racognin.
                                                           site just before the FBD
```

```
Downstream primer, MY-6                                                    (SEQ ID NO:20)
5'-GGC-CTT-AAG-AGC-GCT-CTA-TTA-GAT-GGT-ACA-GCT-TAT-TCT-3'
  'clamp'  Eco RI Eco 47 II  Stop     sequence hybridizing with FBD(1,2)
           site              codons   codons 99-104 (Cf. Fig. 6)
```

The following conditions were used for the PCR: Each of the dNTP's: 200 uM; pFHMG-60 vector as template: 1 ng; MY-10 and MY-6 primers: 20 pmol each; pfu polymerase: 2.5 units; 1× pfu polymerase buffer (Stratagene Inc.), and a total reaction volume of 100 ul. A 'hot start' was given for 5 min at 94° C. The following cycling parameters were used: denaturation at 92° C. for 45 sec, annealing at 50° C. for 60 sec, and extension at 72° C. for another 60 sec. A total of 30 cycles were given, after which a final extension was provided at 72° C. for 10 min. The amplification of the SK-FBD (1,2) hybrid cassette was checked by loading one-tenth of the reaction mixture on a 2% agarose gel. This demonstrated that the expected DNA (369 bp) was satisfactorily amplified in the absence of any background bands. The amplified PCR product was then cloned into pBluescriptII KS(−) after purification through Qiagen PCR-purification column using the manufacturer's protocol. Approximately 2 ug of pBluescriptII KS(−) vector was digested with 10 units of Sma I restriction enzyme in 1×NEB-4 buffer in a 20-ul reaction by incubating the digestion mixture at 25° C. for 12 h. The enzyme was inactivated by heating at 55° C. for 5 min and the linearized plasmid DNA was purified after electrophoresis on a 1% agarose gel. Then, 150 ng of the SmaI-digested vector was ligated with approx. 120 ng of the purified insert DNA (PCR product) in a 25-ul reaction after adding 2.5 ul of 10× (stock) ligase buffer (New England Biolabs Inc., Massachusetts, USA), 1 ul of 10 mM rATP stock and 400 weiss units of T4 DNA ligase. The ligation, was done by incubating the reaction tube at 16° C. for 12 h. After the ligation, the ligase was inactivated by heating at 70° C. for 10 min. The DNA in the ligation mixture was precipitated with n-butanol and then dissolved in 20 ul of dist. water and approx one-third used to transform E. coli XL-Blue electrcompetent cells (Stratgene Inc., USA) by electroporation. Transformants were selected by plating on LB-Amp plates. Miniprep plasmid DNA was prepared from eight selected clones and analysed by agarose gel electrophoresis. The plasmid DNAs of the transformants were run along with pure pBluescript II KS(−) to identify positive clones with larger molecular weight (MW), signifying the presence of the PCR-generated insert DNA. Three transformants were found to be moving slower than the pBluescript DNA on 1.2% agarose electrophoresis. To further confirm that these contained the DNA insert, their plasmid DNAs were digested with EcoRI and BamHI enzymes since EcoRI and BamHI were two of the sites that were introduced in the PCR product during amplification. This showed that a 370-bp fragment, corresponding to the size of the PCR product was liberated, clearly establishing that these clones contained the desired cassette. This was finally confirmed by automated DNA sequencing by the Sanger di-deoxy chain-termination method which showed a complete correspondence with the sequence expected on the basis of the primers and the target DNA viz., FBD(1,2) along with a short stretch at its 5'-end carrying SK-specific and intergenic sequences. The sequencing also established the absence of any other mutation in the amplified DNA. The cassette subcloned in pBluescriptII KS(−) was then transferred into the SK-containing vector, pSKMG400, in order to fuse it in-frame with the SK ORF utilising the common Bsm I site. For cloning the SK-FBD(1-2) hybrid cassette into pSKMG400 vector, both vector and insert DNAs were first digested with BamHI. Roughly 2 ug of the pBluescript-FBD(1,2) and 4 ug of the pSKMG400 were digested with 8 units each of the BamHI enzyme in a 30 ul reaction utilizing buffer D of Promega. The tubes were incubated at 37° C. for 6 h. A small aliquot was run on a 0.7% agarose gel to check for the digestion. After confirming completion of digestion, the reaction was stopped by adding 0.1 volume of 100 mM EDTA. The digested samples were loaded onto 0.8% agarose gel and the desired fragments were cut out as agarose blocks. The DNA was extracted by treatment with beta-agarase as detailed before, and quantitated. Ligation reaction was set up between double-digested vector and the fragment containing the SK-FBD(1,2) cassette using ~200 ng of the vector and 30 ng of the fragment, 4 ul of the ligase buffer, 4 ul of 10 mM rATP, and ~600 Weiss units of ligase in a total volume of 40 ul. The ligation creation was incubated at 16° C. for 12 h. The ligase was inactivated by heating the tube at 70° C. for 10 min then the ligated DNA was precipitated using n-butanol, air-dried and dissolved in a small volume of sterile distilled water. For the transformation step, approx. 100 ng of the ligated DNA was used to transform E. coli XL-1 Blue electrocompetent cells which were plated on LB-Amp plates. Five colonies were picked up and used for plasmid minipreparations. The plasmid DNAs were digested with Afl II and Eco47 III restriction enzymes separately, pBluescript FBD(1,2) and pSKMG400 vectors digested with the same enzymes were kept as controls. The digestion mixtures were run on a 0.7% agarose gel along with double-digested controls. Two clones showed linearization upon Eco47 III digestion. The pBluescript FBD(1,2) control also showed linearization with Eco 47 III digestion, as expected. However, the positive clones were of higher molecular size due to the presence of SK. The pSKMG400 did not show any digestion with Eco 47 III enzyme. The positive clones also gave out an insert upon Afl II digested as anticipated from the known presence of a single Afl II site in SK and another in the FBD(1,2) segment.

Figure 19A:
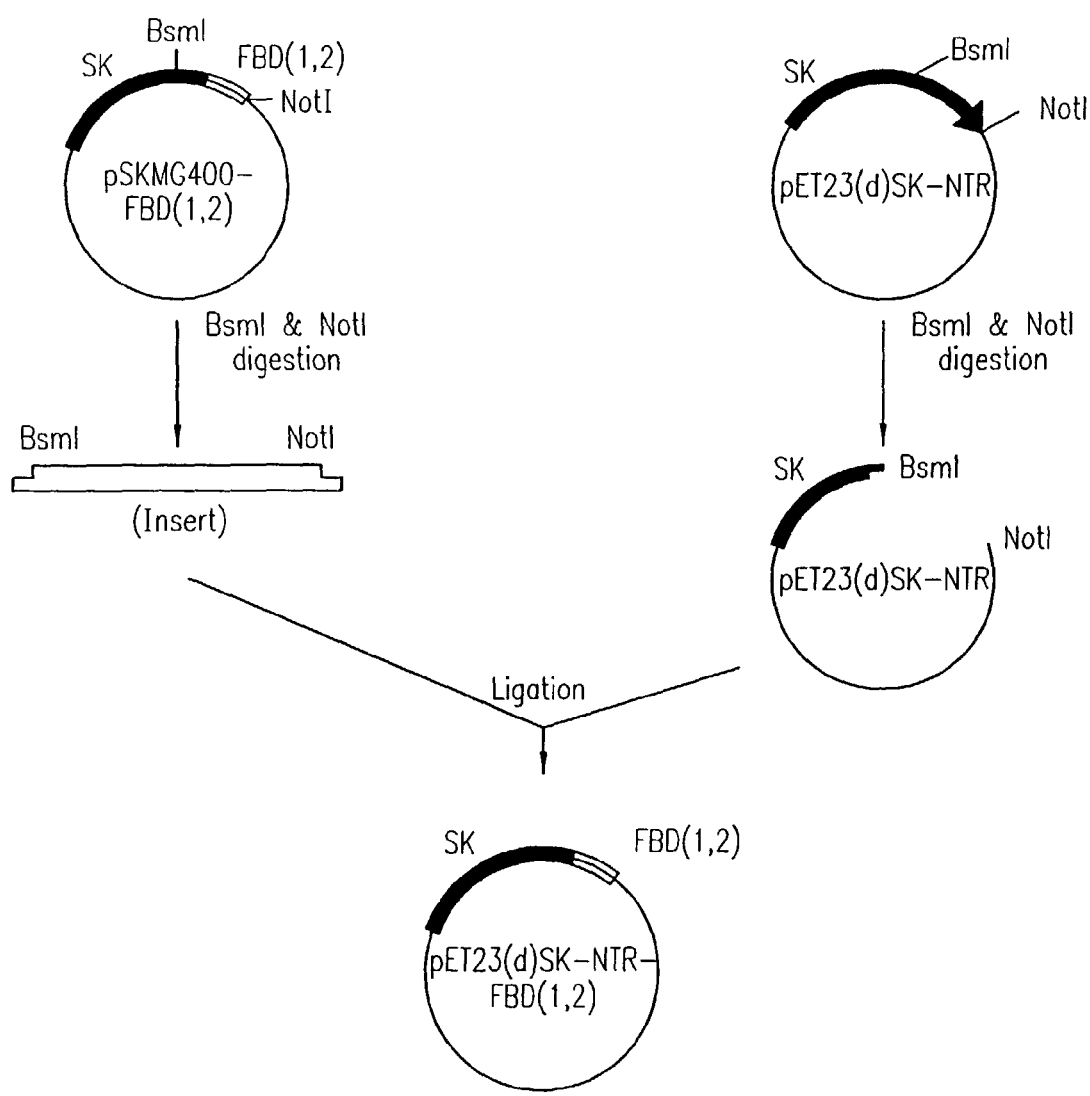
FIG. 19a. Schematic description of steps involved in the cloning of the hybrid gene-construct SK-FBD(1,2) into expression vector pET23(d)SK-NTR for intracellular expression of SK-FBD(1,2) chimera in E. coli.

For the expression of the hybrid SK-FBD(1,2) polypeptide, the Bsm I-Not I fragment from pSKMG400-FBD(1,2) was transferred into pET23(d)SK-NTR at the same sites (see FIG. 19a). Approximately 10 ug of pSKMG400-FBD(1,2) plasmid DNA was digested with 15 U of Not I enzyme in NEB-3 buffer supplemented with 1×BSA by incubating at 37° C. for 6 h in a 60-ul reaction. A second addition of Not I enzyme was again made and the reaction mixture was further incubated for another 6 h. A small aliquot was removed to check for the completion digestion by running an agarose gel. After the NotI digestion, the DNA was precipitated with ethanol and sod acetate (0.3 M). redissolved in 20 ul of dist. water and digested with 20 U of BsmI enzyme in NEB-2 buffer in a 80-ul reaction at 65° C. for 14 h after overlaying the reaction mixture with 50 ul of mineral oil to avoid evaporation. Similarly, in parallel, approx. 5 ug of the vector (pET23(d)SK-NTR) was double-digested with 20 U of Not I and 15 U of BsmI enzymes, sequentially. The linearized vector, and insert were isolated by running a 1% agarose gel and loading the above-mentioned digestion mixtures in-well-separated wells. The vector and insert bands were cut out from the agarose gel using a clean scalpel and the respective DNA fragments were purified, quantitated spectrophotometrically and ligated at a molar ratio of 1:5 of vector insert. Approximately 600 mg of the BsmI/NotI double-digested vector was ligated with 250 ng of the BsmI/NotI double-digested insert in a 20-ul reaction by adding 600 Weiss units of ligase (NEB) and 2 ul of 10× ligase buffer (also of New England biolabs, Inc.) and incubating for 14 h at 16° C. The ligation mix was then heat-inactivated at 70° C. and 15 min, and the DNA was n-butanol precipitated, air-dried, dissolved in 20 uL of sterile water and approx. one-thirds directly used to electroporate E. coli XL-1 Blue electrocompetent cells. The transformants were selected on LB-Amp plates. Ten transformants were picked up and inoculated into fresh LB-Amp for plasmid minipreparation. The miniprep DNAs were digested with BsmI and NotI enzyme along with pSKMG400-FBD(1,2) as control. Three clones were positive in terms of liberating an insert equal in size to that of the insert liberated from pSKMG400 -FBD(1,2). One of the clones was then sequenced to confirm the nucleotide sequence of the SK-FBD gene (see FIG. 19b) and designated pET23(d)SK-NTR-FBD(1,2). This has been deposited with MTCC under accession No. BPL 0014. The plasmid DNA for this clone was transformed into E. coli BL-21 strain grown in liquid culture and induced for the expression of SK-FBD(1,2) hybrid protein with IPTG, as described earlier. Cells from 1.5 ul of the induced culture were pelleted down by centrifugation and were lysed in 100 ul modified SDS-PAGE sample buffer; approx. 25 ul lysate, alongwith that from cells harbouring pET23(d) SK-NTR as control was analysed on 10% SDS-PAGE gel. In parallel, cultures were also grown where IPTG addition was omitted (uninduced controls) and similarly analysed along with induced cultures by SDS-PAGE. The gels showed distinct bands of 57 kD in the IPTG-induced cultures (roughly representing 20% of the soluble protein fraction) indicating the hybrid SK-FBD(1,2) fusion protein had been expressed at high levels intracellularly. In the case of parallel pET23(d)SK-NTR harboring cultures, a major band corresponding to 47 kD, the position of native SK was observed.

Example 5

Figure 20:
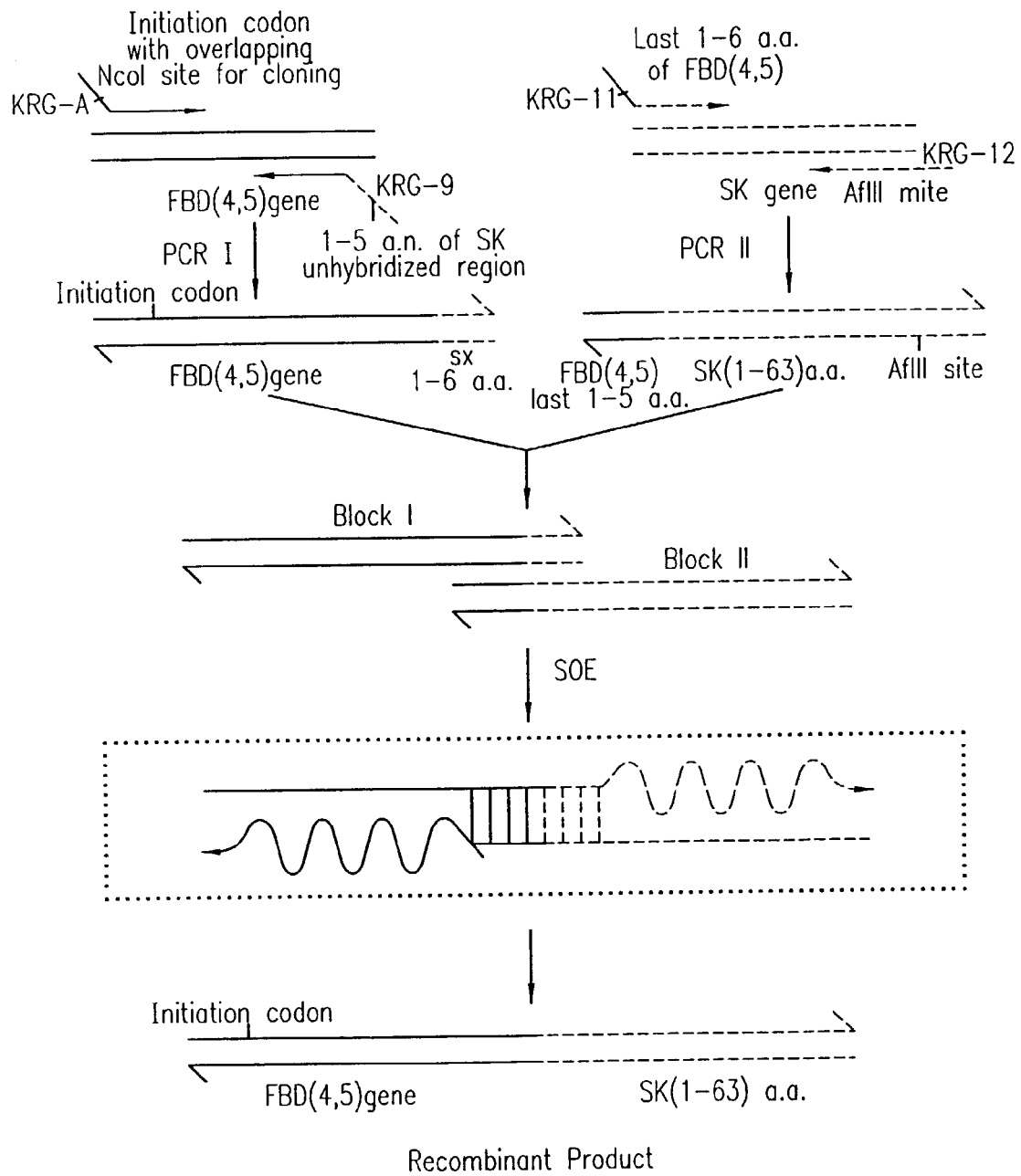
FIG. 20. Scheme of steps involved in the construction of hybrid gene block composed of DNA encoding for FBD(4, 5) and residues 1–63 of SK by the Overlap Extension PCR technique.

In-frame Fusion of DNA Segments Encoding FBD(4,5) at the N-terminal End of the Open-reading-frame Encoding for SK, and Cloning and Expression of the Hybrid Polynucleotide-construct FBD(4,5)-SK in E. coli The construction of the FBD(4,5)-SK hybrid polynucleotide DNA was accomplished by the splicing overlap extension (SOE) method, a procedure in which two (or more) DNA fragments are joined together employing PCR, without using either DNA scission or ligation (in this context, reference may be made to the following publications: Horton, R. M. Hunt, H. D., Ho, S. N., Pullen, J. K., and Pease, L. R., 1989. *Gene* 77:61). The two fragments to be joined by SOE need to have mutually complementary sequences at their respective junctions where the joining is to take place so as to form an 'overlap' (see FIG. 20). These regions of complementarity can be engineered into the two DNA fragments, or 'blocks', to be joined (in the present case, the SK and FBD sequences) through separate PCRs each employing primers specially designed for this purpose. These two PCR-generated blocks are then used in the overlap extension reaction, in a third PCR, wherein the complementary strands hybridize partially at their 3'-ends through the regions of mutual complementarity after strand separation (denaturation) and reannealing. Thus, these two DNA strands act as megaprimers on each other, and in the presence of thermostable DNA polymerase, the 3'-ends of this intermediate are extended to form the full-length (i.e. fused) segment, which may then be further amplified using the flanking primers derived from the first two PCRs used to generate the two DNA blocks. The FBD-SK polynucleotide fusions were made using four synthetic oligonucleotide PCR primers viz, KRG-8, KRG-9, KRG-11 and KRG-12 whose sequences and design are described below (see a FIG. 19 for the overall scheme followed for the construction of the chimeric gene-construct).

```
Upstream PCR-I primer KRG-8:

Transglutamate recognition site                         (SEQ ID NO:21)
                                    150       152      154
5'-CC-ATG-GTG-CAA-GCA-CAA-CAG-ATT-GTA-CCC-ATA-GCT-GAG-AAG-TGT-3'
Partial Nco I
   site                              hybridizes to begining of FBP(4) segment
                                     (codon numbers of FBD are shown as per Fig. 6)

Downstream PCR-I primer KRG-9:

sequence complementary to codons 1-5 of SK (No.'s indicated below)      (SEQ ID NO:22)
5'-CTC-AGG-TCC-AGC-AAT-ACG-AAC-ATC-GGT-GAA-GGG-GCC-AGA-T-3'
      5   4   3   2   1  259     257     255         253
                          sequence hybridizing with end of FBD(5) segment (No.'s
                          indicated
                          are codons, as per Fig. 6).

Upstream PCR-II primer, KRG-11

(SEQ ID NO:23)
            FBD(5) sequence, as overhang;        sequence hybridizing with SK gene; codon No.s
            Codon numbers (cf. Fig. 6)           (Cf. Fig. 3) are indicated.
            are indicated.
            5'-TTC-ACC-GAT-GTT-CGT-ATT-GCT-GGA-CCT-GAG-TGG-CTG-CTA-GAC-3'
                255      257 259  1    3    5    7    9
```

-continued

Upstream PCR-II primer, KRG-12

(SEQ ID NO:24)

```
5'-TGG-TTT-TGA-TTT-TGG-ACT-TAA-GCC-TTG-3'
    62    60 58      56      54
```

Note: sequence hybridizing with SK gene (codon No.'s are indicated; see Fig. 3)

As can be seen above, the upstream primer, KRG-8, was homologous to the the beginning 18 nucleotides of the 'anticoding' strand of the FBD-4 encoding DNA and also carried at its 5' end non-hybridizing DNA sequences that encoded for a Nco I site (to facilitate the 'docking' of the SOE product into the Nco I site of the expression vector, thus recreating the ORF for the FBD(4,5)-SK fusion sequences). The upstream primer also contained sequence coding for a transglutaminase cross-linking site. The downstream primer KRG-9 was designed to hybridize with the end of the FBD(5) DNA sequence, but also contained at its 5' non-hybridising end, nucleotides complementary to the first 5 codons of the ORF encoding mature S. equisimilis SK (see FIG. 6). The template used for the first PCR to obtain Block I (see FIG. 20) was FBD(4,5) cloned in pBlueScript [pSKMG400-FBD(4,5)]. The first PCR (termed PCR-I) was carried out using approx. 20 ng template and 30 pmol of each primer in a 100 ul-reaction using the buffer provided by Stratagene Inc., the supplier of the pfu thermostable polymerase. The PCR employed 25 cycles with the following conditions: 94° C. for 45 sec (denaturation step) followed by 50° C. for 1 min (annealing step), and 72 C. for 1 min (extension step). This was followed by an incubation for 4 min at 72° C. for extension of any incomplete chains. The PCR resulted in the generation of a single species of DNA, in according with the size expected from the fusion construct (368 bp), as observed by agarose gel electrophoresis; this DNA species was isolated from the gel as a small agarose block, and subjected to further purification using the agarase treatment method, described earlier.

Figure 21A:
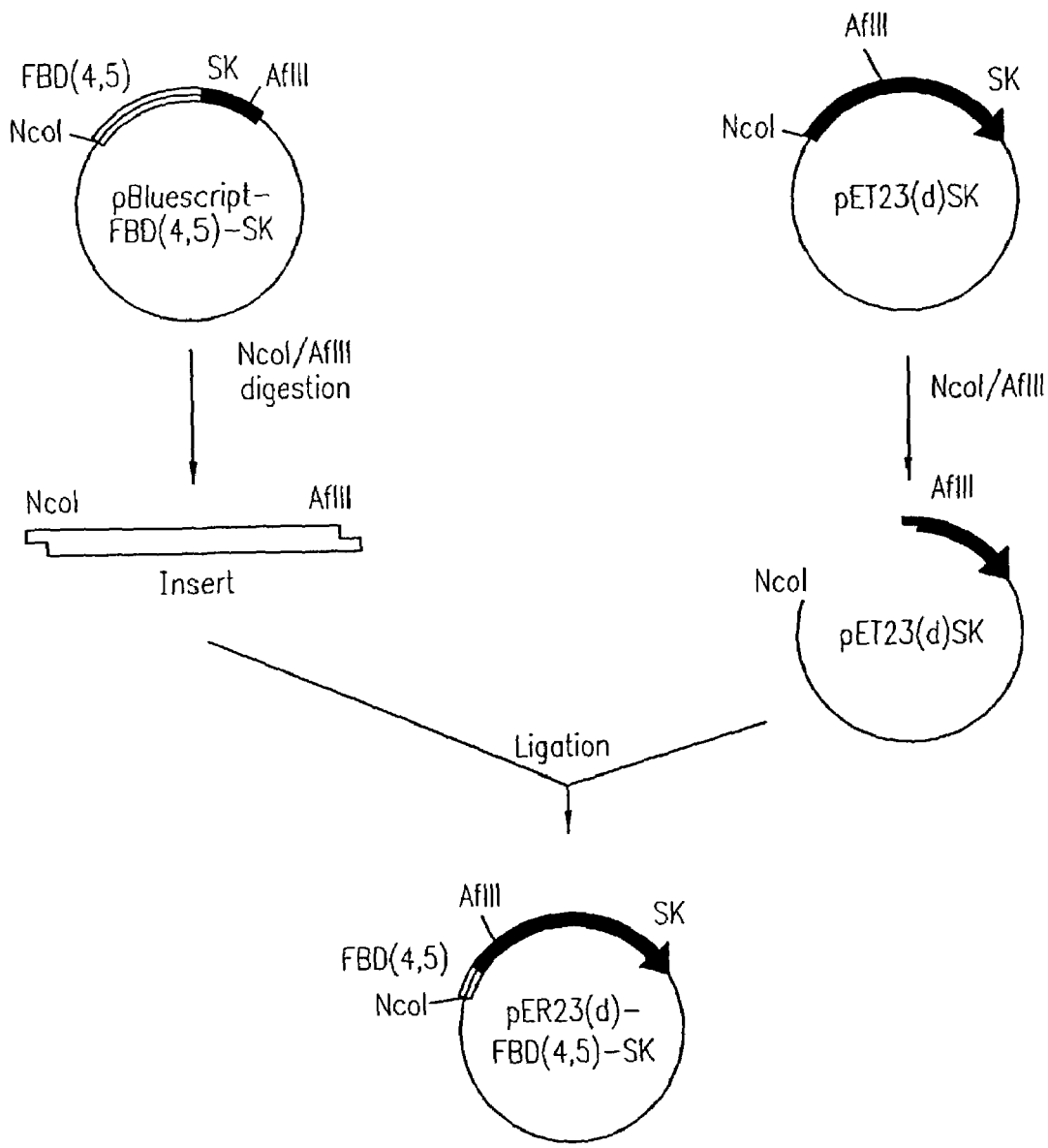
FIG. 21a. Scheme depicting steps involved in the cloning of the FBD(4,5)-SK gene block for expression of FBD(4, 5)-SK chimera in E. coli.

For obtaining the DNA Block II for the SOE reaction, only the region of the SK-encoding polynucleotide DNA corresponding to nucleotide 1 to 186 (approx. corresponding to the first 63 amino acid residues of SK; see FIG. 3) was amplified using pSKMG400 as template in PCR II, the primer set KRG 11 (upstream primer) and KRG 12 (downstream primer). This region encompasses the unique Afl II site in the SK gene (see FIG. 4). The upstream primer contained non-hybridizing bases that were homologous to the last five codons of the FBD(5)-encoding DNA (viz., codons 255–259), followed by a stretch of bases hybridizing to the first 27 bases of the anti-sense strand of the SK-encoding ORF (see FIG. 3). The downstream primer contained sequences hybridizing with the stretch of DNA encoding for residues 55–63 of SK containing the Afl II restriction site so that the SOE product could be docked back into the full-length SK-encoding polynucleotide segment contained in the vector used for the expression of the hybrid gene(see FIG. 21a). The PCR was carried out essentially as described for PCR I, above, except that 90 ng of template was chosen and the cycling conditions selected had a lower annealing temp. (43° C.) dictated by a relatively lowered $T_m$ of one of the primers. The PCR gave a single DNA band of the expected size (201 bp) on agarose gel electrophoresis, which was isolated and purified as for PCR I product (Block I). Splice overlap extension reaction (PCR III) was then carried out to obtain the hybrid DNA between the FBD and SK ORFs. In this reaction, approx. equivalent amounts of the purified DNAs from PCR I and PCR II were mixed together (representing approx. one-fifteenth of the amplified DNA obtained from PCRs I and II) in a 100-uL reaction. To bring about optimal and specific annealing between the hybridizing areas of the two partially complementary strands from the FBD(4,5) and SK 1-63 DNA blocks (see FIG. 20) (Phase I), the reaction was first carried out in the absence of any other primers, using pfu DNA polymerase and the buffer specified by its supplier, employing the following conditions: 98° C. for 2 min, slow temperature decrease (i.e. 'ramp' of 4 min) to 50° C., maintenance at 50° C. for 1 min followed by 3 min at 65° C. A 'hot start' was used for the initiation of the PCR (i.e. the DNA polymerase was added into the reaction after all other components had been added and thermally equilibrated to the highest temperature in the cycle). A total of 10 cycles were carried out first (Phase I), to allow formation of overlapped extended products. In the second phase, primers KRG 8 and KRG 12 were added under hot start conditions, and another 25cycles were given at the following cycling conditions: 94° C. for 1 min (denaturation step), 40° C. for 1 min (annealing), followed by extension at 72° C. for 1 min to amplify the fusion products. Finally, after 10 min at 72° C., an aliquot from the PCR was analysed agarose gel electrophoresis. It showed the clean appearance of the expected hybrid product (539 bp) with the absence of any other background bands. This was isolated from the agarose gel, purified and then kinased with T4 phage polynucleotide kinase by standard protocols. The kinased (i.e. 5'-phosphorylated) product was then blunt-end cloned at the Eco RV site of pBlueScript. Clones containing the SOE product were selected by restriction enzyme digestion to isolate the inserts and measuring their size by agarose gel electrophoresis. The positive clones were then sequenced to confirm the identity of their DNA inserts as well as the absence of any mutations(see FIG. 21b). After Nco I and Afl II digestion of one of these two clones, the Nco I-Afl II fragment carrying the FBD4(,5)-SK 'hybrid polynucleotide cassette' was ligated with Nco I-Afl II digested SK-expression plasmid (pET(23d)-SK) and transformation of E. coli XL-Blue cells was cored out to obtain the hybrid FBD(4,5)-SK ORF in this vector (FIG. 21a). The resultant plasmid pET23(d)-FBD(4,5)-SK has been deposited with MTCC under accession No. BPL 0015. This plasmid construct was transformed into E. coli BL-21 cells to monitor expression of the hybrid FBD-SK construct from the T7 RNA polymerase promoter-based vector, as described before. The SDS-PAGE gels showed the expression intracellularly of a protein with the expected MW (approx. 57 kD) at a level of around 20 percent of total intracellular, soluble protein.

Example 6

In-frame Fusion of DNA Segments Encoding for FBD Segments 4 and 5 at Both the Ends of the DNA ORF Encoding for SK, and Cloning and Expression of the Hybrid Polynucleotide-construct so Formed, FBD(4,5)-SK-FBD(4, 5), in E. coli.

Figure 22A:
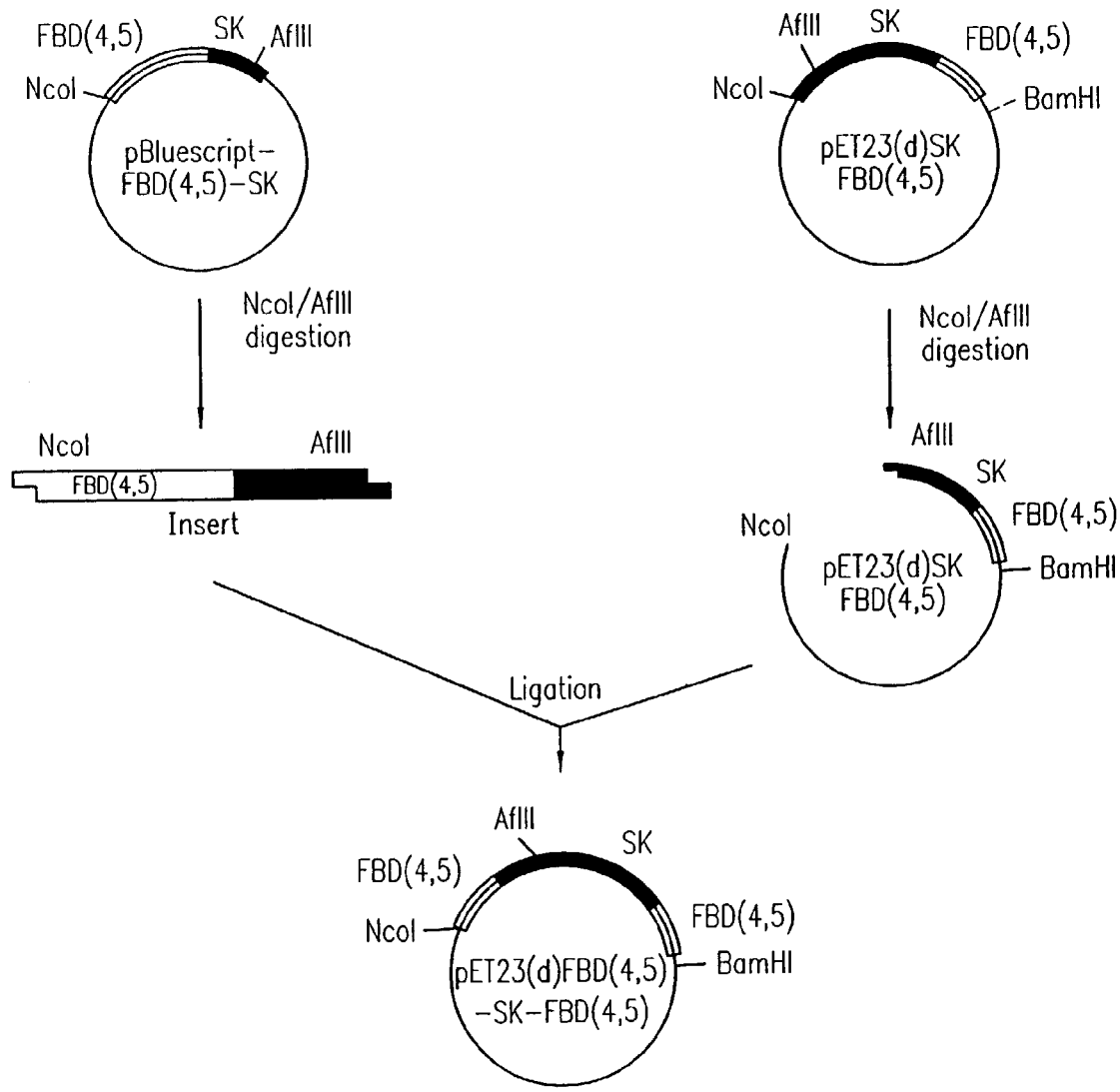
FIG. 22a. Flow chart depicting schematically the steps involved in the construction of FBD(4,5)-SK-FBD(4,5) hybrid gene in pET23(d) expression vector.

The steps involved in the construction of a SK-FBD polynucleotide hybrid wherein the FBD(4,5) domains were fused in-frame simultaneously at both ends (i.e. the N- and C-termini) of the SK-encoding ORF [i.e. FBD(4,5)-SK-FBD (4,5)] are shown schematically in FIG. 22a. It is based on the cloning of the FBD(4,5)-SK(1-57 residues) cassette obtained from pBlueScript-FBD(4,5)-SK vector, described in Example 5 (above). into pET-(23d)SK-FBD(4,5) at the beginning of the ORF for SK. Approximately 5 ug each of pET(23 d)SK-FBD(4,5) and pBlueScriptFBD(4,5)-SK plasmid DNA were digested with Afl II and Nco 1 restriction endonucleases and the digests were electrophoresed on 1.2% agarose gels alongwith standard DNA size markers by standard methods. In each case, two fragments were observed, corresponding to the vector DNAs (expected size, 5012 bp) devoid of the Nco I-Afl II fragment, and the latter fragment [approx. 520 bp in the case of pBlueScriptFBD(4, 5)-SK and 140 bp in case of pET-(23d)SK-FBD(4,5)] released from the parent vectors as a result of the doubledigestion (see FIG. 22a showing the Afl II and Nco I sites in the two vectors). The NcoI-Afl II fragment from pBlueScript FBD(4,53SK, containing the FBD(4,5)-SK(1-57 residues) cassette, to be used as insert, and the NcoI-AflII digested vector DNA from pET-(23d)SK-FBD(4,5) were isolated from the agarose gel and purified. Both fragments were then subjected to ligation using T4 DNA ligase under standard conditions using a molar ratio of 1:2 of vector to insert DNA. The ligation mixture was then transformed into electrocompetent E. coli XL-1 Blue cells. Positive clones, with both ends of SK fused with the FBD(4,5) domains, were selected on the basis of difference in size from the parent vectors, as well as to ability to yield the expected fragment (containing FBD sequences at both ends of the insert) after digestion with Nco I and Bam HI enzymes (see FIG. 22a). The veracity of the constructs was then established by subjecting one of the selected clones to automated DNA sequencing using Sanger's di-deoxy method to sequence the entire hybrid ORF (see FIG. 22b). This demonstrated that the construct had the expected design and sequence, with one 'set' of FBD4,5 domain fused at the beginning of the SK-encoding polynucleotide, and another at its end (i.e. after DNA encoding for residue 383). This plasmid construct has been designated pET23(d)FBD(4,5)-SK-FBD(4.5)], and deposited with MTCC (Accession No. BPL 0016 in host E. coli XL-Blue). It was also used to transform E. coli strain BL-21 electro-competent cells, in order to express the FBD-SK-FBD hybrid construct intracellularly in E. coli. The hybrid gene was then expressed in E. coli intracellularly after induction with IPTG exactly as described earlier, and the cell lysates analysed by SDS-PAGE. These showed the expression of a polypeptide of approx: MW 65 kD as expected from the incorporation of the two FBD segments at each ends of the SK (I-383) gene. The level of expression of this protein was observed to be approx. 20–25 percent of the total soluble protein fraction.

Example 7

Purification of Various Chimeric Constructs Formed SK and FBDs after Expression in E. coli and Refolding, and Testing of Their Affinity for Human Fibrin.

Figure 23:
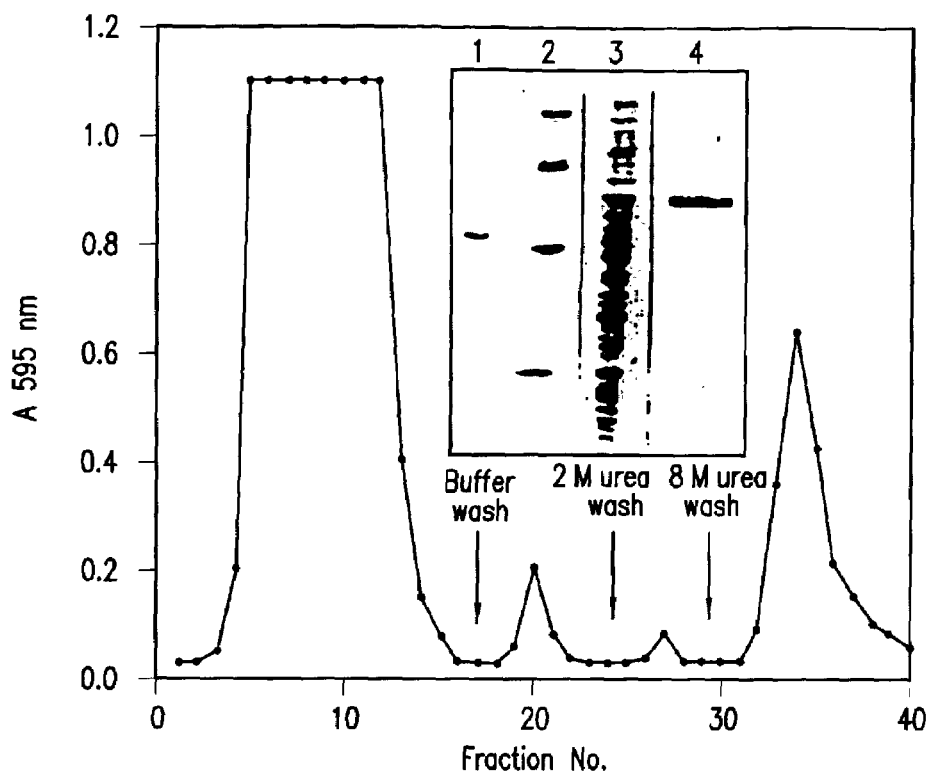
FIG. 23. Purification of SK-FBD(4,5) protein expressed in E. coli by a one-step affinity chromatographic procedure.

Fifty ml LB-Amp (containing 100 ug/ml of ampicillin per ml) were seeded with E. coli cells harbouring either pET23 (d)-SKFBD(4,5), pET23(d)-SKFBD(1,2), pET-23(d)FBD (4,5)-SK or pET23(d)-FBD(4,5)-SK-FBD(4,5) plasmid constructs in separate flasks (150 ml capacity). The inoculation was done from the respective glycerol stocks, and the culture was incubated at 37° C. for 12 h on a rotary shaker (200 r.p.m.). This pre-inoculum was used to seed fresh LB-amp at 5% (v/v) level (one liter total for each type of E. coli BL-21 cells harbouring one of the different plasmid constructs described above with 500 ml medium per 2 liter conical flask), and the cultures shaken as above at 37° C. for approx. 2 h 30 min. at which time the OD600 of the cultures had reached a value of 1.0–1.1. The expression of the chimeric SK/FBD polypeptides in the cultures were then induced by the addition of IPTG to 1 mM, and continuing further the incubation for another 3 h. Cells from all four cultures were then harvested by high-speed centrifugation (8000 g×30 min) at 4° C., and washed once with 500 ml cold ST buffer (pH 7.5). Finally, each cell pellet was suspended in cold 15 ml ST buffer, pH 8.0. The wet-weight of the pellets obtained from 1 liter cultures varied between 4.3–4.5 g. Each cellsuspension was then subjected to ultra-sonication to effect cell-lysis using standard methods. The lysates so obtained (approx. 28 ml each) were subjected to high-speed centrifugation at 4° C. to pellet any unlysed cells and/or cell debris. The protein conc. in the supernatants varied between 15.0 to 16.0 mg/ml. These were then diluted to a final protein of 1 mg/ml using distilled water, together with the addition of the following additional components (final concentrations in the diluted mix are given): Tris-Cl, pH 8.0, 50 mM; NaCl 150 mM; EDTA 1 mM; mixture of reduced and oxidized glutathione 123:50 mg. To these refolding mixtures (approx. 400 ml each) were then added 30 ml (packed volume) of fibrin-Sepharose beads pre-equilibrated with 50 mM Tris-Cl, pH 8.0. The mixtures were at 22° C. for 16 h to effect reoxidation/refolding. The solutions were then passed through 50 ml-volume axial glass columns fitted with fritted glass disks (to retain the Sepharose-beads). The packed fibrin-Sepharose beds were then washed with approx 170 ml binding buffer (50 mM tris-Cl, pH 8.0, and 150 mM NaCl), followed by 100 ml of 2 M urea (in binding buffer), and finally the fibrin-bound protein was eluted with 6 M urea (in binding buffer). All the washing/elution steps were carried out at a flow rate of ~30 ml/h using a peristaltic pump assembly. The chromatographic profile in case of SK-FBD (4,5) fibrin-Sepharose affinity purification, and analysis of the different fractions, are shown on FIG. 23. Similar results were obtained in case of the other SK-FBD constructs. A total of 3.8 mg of protein was eluted alongwith the 6 M urea-wash in the case of SK-FBD(4,5), whereas for SK-FBD (1,2) approx. 4 mg, for FBD(4,5)-SK 3.5 mg, and for FBD(4,5)-SK-FBD(4,5) 6.2 mg of protein was obtained at the 6 M urea elution step. In case of the SK control, no protein was found to elute alongwith the 6 M urea. The removal of the urea, and concentration of the protein, was effected by ultrafiltration through 10 kD cut-off membranes. Aliquots of each of the four fibrin-specific SK-FBD chimeric products were then subjected to SDS-PAGE analysis on 10 percent acrylamide gels with and without reduction with beta-mercaptoethanol to determine their relative purities as well as monomeric/polymeric character. Standard molecular weight marker proteins as well as pure native SK from S. equisimilis were also run on the same gels. The SDS-PAGE analysis, either in the presence or absence of reducing agent, showed all of the fibrin-Sepharose eluted chimeric product to be essentially pure and monomeric; in all cases, a single prominent band stained with Coomassie Blue and very few faint background bands visible (not more than 2–5% cumulatively), The MWs of the refolded protein were completely in accord with those from theoretical considerations i.e. extrapolated from the MW of individual domains of FBD, the SK portion, and linker sequence, if present. The SK-FBD(4,5) and SK-FBD(1,2) bands moved with the same mobility on SDS-PAGE, with an apparent MW of around 55 kD; however, the FBD-(4,5)-SK construct showed a slightly lowered mobility as compared to either SK-FBD(4,5) or SK-FBD(1,2). This was in accord with the fact that whereas the former two hybrid constructs contained approx. 31 amino acid residues' deletion at the C-terminal end of the SK moeity of the hybrid, the FBD(4,5)-SK construct had full-length SK integrated in its design (see Examples, above). The FBD(4,5)-SK-FBD(4,5) construct, containing four FBDs alongwith SK, moved with a MW corresponding to 60 kD on SDS-PAGE. In the absence of beta-mercaptoethanol, the MW's calculated for all four hybrids were approximately the same as observed in the presence of beta-mercaptoethanol, indicating that the constructs obtained after refolding and binding with fibrin-Sepharose contained essentially monomeric forms of the polypeptides.

The specific activities of the purified protein for PG activation, as determined by the chromogenic assay were: $2.2 \times 10^4$ I.U./mg for SK-FBD(4,5), $1.8 \times 10^4$ I.U./mg for SK-FBD(1,2), $4 \times 10^4$ I.U./mg in case of FBD(4,5)-SK and $5 \times 10^2$ I.U./mg for FBD(4,5)-SK-FBD(4,5), respectively. Under the same conditions, native S. equisimilis SK, or SK purified from E. coli (Met-SK) as described in Example 2, above, showed a much higher activity ($\sim 1.0 \times 10^5$ I.U/mg). The reason for the apparently lowered specific activities in case of the chimeric proteins was revealed when these were assayed by a single-phase, continuous spectrophotometric assay by directly determining their rates (slopes) for HPG activation by standard methods (Wohl, R. C., Summaria, L., and Robbins, K. C., 180, J. Biol, Chem. 255:2005). These assays revealed that whereas native SK or E. coli-expressed Met-SK did not display an appreciable lag in the progress curves obtained for the PG activation reactions (less than 1 min), all of the hybrid proteins displayed significant initial periods in their PG activation profiles (varying from 7 to 25 min depending on the construct) wherein little or no plasmin formation occurred. However, after the initial lags, the PG activation proceeded with a high rate, generating slopes closely similar to those obtained with native SK (see below).

Example 8

Functional Characterization of the Chimeric Proteins in Terms of Their Altered Kinetics of Plasminogen Activation and Fibrin Clot Dissolution The proteins prepared in Example 7, above, as well as native and Met-SK (as controls) were examined with respect to their PG activation kinetics. This essentially entailed the study of the time-course of PG activation by the various SK/FBD chimeras and the determination of their steady-state kinetic constants for PG activation. A one-stage assay method was used to measure the activation of HPG; reference in this context may be made to several publications in the literature e.g., Shi, G. Y., Chang, B. I., Chen, S. M., Wu, D. H. and Wu H. L., 1994, Biochem. J. 304:235; Wu, H. L., Shi, G. Y., and Bender, M. L., 1987, Proc. Nati. Acad. Sci. 84: 9292; Wohl, R. C., Summaria, L., and Robbing, K. C., 1980, J. Bid. Chem. 255: 2005; Nihalani, D., Raghava, G. P. S., Sahni, G., 1997, Prot. Sci. 6:1284). Briefly, it involved the addition of the activator proteins to be studied in a small aliquot (~5 ul) into 100 ul-volume microvette containing 1 uM of HPG in assay buffer (50 mM Tris-Cl buffer, pH 7.5, containing 0.5 mM chromogenic peptide substrate and 0.1 M NaCl). The protein aliquots were added after addition of all other components into the cuvette and bringing the spectrophotometric absorbance to zero. The change in absorbance at 405 nm was then measured as a function of time in a Shimadzu UV-160 model spectrophotometer. While SK showed a rapid PG activation kinetics, the kinetics for SK-FBD chimeric protein displayed a characteristic lag, or delay, in the initial phase of the rate of PG activation that was clearly different from the rates seen with SK. This property viz., initial delay in HPG activation, as well as its magnitude, was largely independent of the amount of the chimeric protein employed in the assay, as well as the concentration of HPG in the reaction. Another notable feature was that the lag-times associated with the different chimeric proteins under the same conditions. In the case of SK-FBD( 1,2) and SK-FBD(4,5) the lag period corresponded to 10–12 mm, for FBD(4,5)-SK 7–8 mm and 20–25 mm in case of FBD(4,5)-SK-FBD(4,5). Under the same conditions (~1 uM HPG, 1–2 nM of protein), native SK or Met-SK displayed very little lag period (i.e. less than 1 min duration) during PG activation.

The mechanism of the initial lag in the various SK-FBD chimeras was investigated by examining the SDS-PAGE profiles of various aliquots withdrawn from plasminogen activation reactions withdrawn at different time-intervals after the mixing of SK or SK-FBD chimeric protein with human PG. These showed that the appearance of rapid PG activation following the lag period closely coincided with the cleavage of the FBD portion from the rest of the molecule (SK portion) as evidenced by a reduction of the molecular weight of the hybrid. That the proteolysis was mediated by trace amounts of plasmin in the system was evident by the observation that either removal of trace plasmin by passage of the human PG through soybean trypsin inhibitor agarose (a material that selectively binds plasmin and does not bind plasminogen) led to very high periods of lag for all of the hybrid proteins [viz., from 10–12 min to approx. 25 min. for SK-FBD (1,2), SK-FBD (4,5, and FBD(4,5)-SK; to approx 35 mm for FBD(4,5)-SK-FBD(4,5) from an initial value of approx. 20 min]. Alternatively, the addition of small quantities of quantities of performed human plasmin into the PG activation reactions (made by the conversion of PG to plasmin with agarose-immobilized urokinase) reduced the lag periods associated with the different SK-FBD chimeras.

To determine the steady-state kinetic parameters for HPG activation of the activated forms of the hybrids, fixed amounts of SK or SK-FBD chimeric protein (1 nM) were added to the assay buffer containing various concentrations of HPG (ranging from 0.035 to 2.0 uM) in the 100 uL assay micro-cuvette as described above. The change in absorbance (representing velocity, v) was then measured spectrophotometrically at 405 nM for a period of 30 min. at 22° C. All determinations were done in triplicates and their averages taken for analysis. The kinetic parameters for HPG activation were then calculated (using the linear portion of the progress curves) from inverse, Lineweaver-Burke plots using standard procedures (Wohl, R. C., Summaria, L., and Robbins, K. C., 1980., J. Biol. Chem. 255: 2005), the 1/v value is plotted on the ordinate axis and 1/S value is plotted on the abscissa, S representing the (varying) concentration of substrate (HPG) employed for the reaction/s. From these plots, the $K_m$ for HPG ($K_{plg}$) and maximal velocities (at saturating HPG concentrations) were determined (set forth in the following Table).

These data clearly show that once fully activated after completion of the initial lag, all the chimeric constructs became significantly active in terms of their PG activation abilities in comparison to SK.

TABLE

Steady-state kinetic parameters for HPG activation by SK and SK-FBD hybrid proteins*

| Activator protein | $k_{plg}$ (μM) | Maximal activity# | Lag (min) |
|---|---|---|---|
| nSK | 0.14 ± 0.02 | 100.0 | 1.0 |
| Met-SK | 0.18 ± 0.01 | 95.5 ± 52.0 | |
| SK-FBD(4,5) | 0.15 ± 0.02 | 52 ± 4 | 10.0 |
| SK-FBD(1,2) | 0.18 ± 0.03 | 58 ± 5 | 10.5 |
| FBD(4,5)-SK | 0.16 ± 0.02 | 65 ± 4 | 8.0 |
| FBD(4,5)-SK-FBD(4,5) | 0.20 ± 0.03 | 45 ± 4 | 18.0 |

*The parameters were calculated from the linear phases of the reaction progress curves after the abolishment of the lag phases.
Expressed relative to the activity of native SK from Streptococcus sp. (ATCC 12449), taken as 100 percent.

In a separate series of experiments, the rates of proteolytic dissolution of radiolabelled fibrin clots in vitro was examined to test whether, like native SK, the SK-FBD chimeric proteins could also efficiently break down fibrin to soluble products, a fundamental biological property of all thrombolytic agents, and also to examine if the altered PG activation kinetics observed with synthetic peptide substrate, described above (i.e. slow initial rates, followed by rates close to those observed for native SK) were also reflected at the level of clot lysis.

Radioactive fibrin clots were first prepared by mixing 400 ul of cold fibrinogen (2.5 mg/ml stock) with 50 ul of $^{125}$I-labelled fibrinogen containing $9 \times 10^5$ cpm (specific activity $7.2 \times 10^5$ cpm/ug protein) and adding to a solution (150 ul) containing 100 ug HPG and 0.25 N.I.H. units of thrombin (Sigma). All solutions were made in 0.1 M citrate phosphate buffer, pH 7.5, containing 0.8 percent BSA (BSA-citrate buffer). The final volume of the clotting reaction was adjusted to a total volume of 1 ml with BSA-citrate buffer. The clot was formed by incubating the mixture in a glass tube at 37° C. for 2 min. The clot was then washed thrice with 2 ml of TNT buffer (50 mM Tris-Cl buffer, pH 7.5, containing 38 mM NaCl and 0.01 percent Tween-80) for 3 min at 37° C. When required non-radioactive fibrin clots were prepared exactly as described above but omitting the inclusion of $^{125}$I-labelled fibrinogen from the clotting mixture. The effect of the thrombolytic agent (native SK or SK-FBD hybrid) was then studied in terms of release of radioactivity from the clot kept either in a plasma milieau or in presence of excess human fibrinogen as described below.

Figure 24:
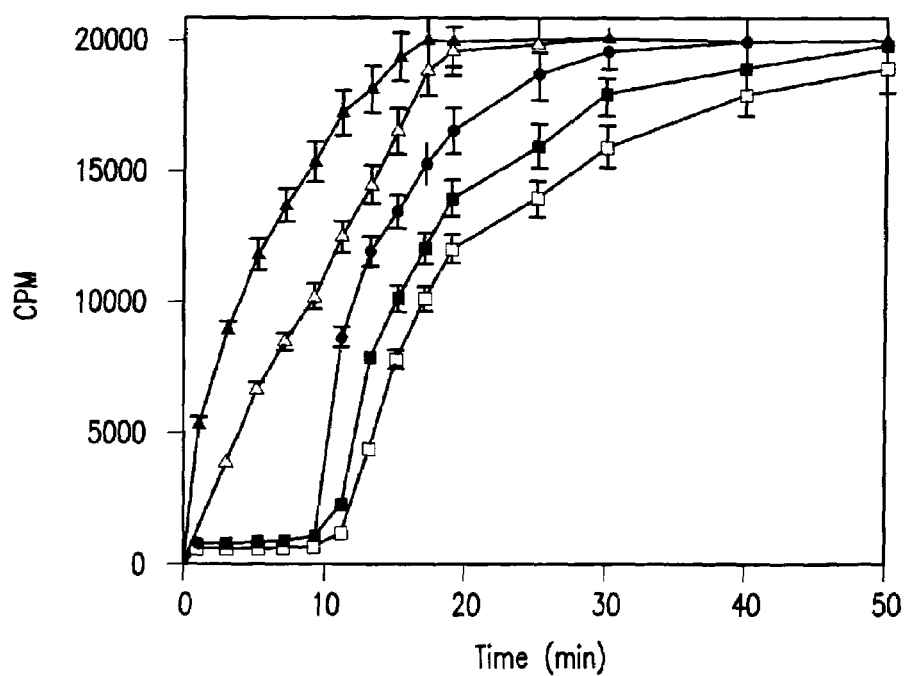
FIG. 24. Clot lysis by purified SK-FBD(4,5) chimeric protein in a plasma milieau.

Clot lysis of pre-formed fibrin clots suspended in human plasma was carried out by suspending $^{125}$I-labelled and extensively washed clots in 2 ml citrated human plasma, pre-warmed at 37° C., and adding different amounts of either SK or a given SK-FBD-hybrid protein. The reaction tubes were rotated slowly at 37° C. in a water bath and 0.1 ml aliquots of the soluble fraction were removed at regular intervals to measure the $^{125}$I-fibrin degradation products released by measuring the amount of radioactivity using a gamma counter. The total radioactivity in each clot was determined by measuring the radioactivity of the respective tube before withdrawing any aliquot prior to the addition of thrombolytic agent. A comparison of the dissolution kinetics of radio-labelled fibrin clots by native SK and the various SK-FBD chimeric proteins in plasma milieau also clearly showed that the lag displayed by the latter during the PG activation assays was essentially preserved during clot lysis also. While SK caused relatively rapid dissolution of the fibrin and a plateauing of the dissolution reaction at or around 15 min, a prolonged lag in the case of the SK-FBD (4,5) hybrid protein (approx. 10 min) was evident at the same protein concentration (representative data for these two proteins are shown in FIG. 24). In the case of the other hybrids, the lag-times in plasma were essentially as seen with PG activation assays viz. 10 min for SK-FBD(1,2), 8 min for FBD(4,5)-SK, and 18 min for FBD(4,5)-SK-FBD (4,5).

Clot lysis in the presence of an excess of human fibrinogen was also carried out by measuring the rate of dissolution of radio-labelled fibrin clot by SK or SK-FBD protein in the presence of various concentrations of human fibrinogen (1–4 mg/ml) and 100 nM of either SK or SK-FBD hybrid protein. Clot lysis was also performed in the presence of fixed fibrinogen concentration (2 mg/ml) but employing different concentrations of SK/SK-FBD protein (ranging from 50 to 200 nM). The reactions were incubated at 37° C. in a water bath with gentle shaking, and the release of $^{125}$I-fibrin degradation products as a function of time was measured in the supernatant, as described above. All of the hybrid proteins were able, like SK, to dissolve the fibrin clots in a dose-dependent manner; however, there was a distinct lag in the case of the SK-FBD hybrids closely similar to that seen with clot lysis in plasma milieau. The lag period varied with construct design viz., in case of SK an absence of any appreciable lag was observed (less than 2 min.). The lag times for SK-FBD(4,5) and SK-FBD(1,2) were 10–11 min; for FBD(4,5)-SK 7–8 min; and 18–20 min for FBD(4,5)-SK-FBD(4,5).

Advantages of the Invention

The advantage of the present invention lies in its disclosure of the design of structurally defined SK-FBD chimeric polynucleotide DNAs in which the translational in-frame fusion of the DNAs encoding SK, or its modified forms, and those for the minimally essential human Fibronectin gene that are capable of possessing significant fibrin affinity on their own, such as those FBDs that possess independent fibrin binding capability (e.g., "finger" domains 4 and 5 of human fibronectin) has been carried out in such a manner that the polypeptide/s expressed from these polynucleotide constructs possess fibrin affinity (which SK, on its own, does not possess) together with a delayed PG activation kinetics (unlike SK which show an immediate activation of PG).

The simultaneous presence of the afore-mentioned properties in the same PG activator confers distinct advantages into the resultant proteins. Soon after injection into the body, whilst the chimeric PG activator proteins are still in an inactive or partially active state, they will bind to the pathological fibrin clot during their sojourn through the vascular system in an inactive/partially active state. However, after an initial lag, these will become fully activated in the immediate vicinity of the clot, thereby obviating the systemic PG activation coincident with natural SK administration. Whilst the former property would be expected to confer on the thrombolytic agent/s an ability to target itself to the immediate locale of the pathological clot and thus help build up therapeutically effective concentrations of the activator therein, the initially slowed kinetics of PG activation would result in an overall diminished generation of free plasmin in the circulation prior to their localization to the site of circulatory impedance induced by the pathological fibrin clot. The net result shall be a continued and more efficient fibrinolysis at the target sustained by considerably lowered therapeutically effective dosages of the thrombolytic agent.

The invention claimed is:

1. A chimeric polypeptide comprising the following components:
   (a) a streptokinase component capable of plasminogen activation; and
   (b) a fibrin-binding component, wherein said fibrin-binding component is fibrin-binding domains 4 and 5 of fibronection or is fibrin-binding domains 1 and 2 of fibronection;
   wherein said streptokinase component and said fibrin-binding component are fused via a peptide bond and are linked through a region that is sufficiently flexible so as to allow plasmin-dependent activation of the streptokinase component,
   wherein said chimeric polypeptide is encoded by a polynucleotide selected from the group consisting of SEQ ID NO: 9, SEQ ID NO: 10, SEQ ID NO: 11, and SEQ ID NO: 12.

2. A pharmaceutical composition comprising the chimeric polypeptide of claim 1, and a stabilizer.

3. The pharmaceutical composition of claim 2, wherein said stabilizer is human serum albumin or mannitol.

* * * * *

SEQUENCE LISTING

<160> NUMBER OF SEQ ID NOS: 28

<210> SEQ ID NO 1
<211> LENGTH: 1245
<212> TYPE: DNA
<213> ORGANISM: Streptococcus equisimilis
<220> FEATURE:
<221> NAME/KEY: CDS
<222> LOCATION: (1)...(1242)

<400> SEQUENCE: 1

```
att gct gga cct gag tgg ctg cta gac cgt cca tct gtc aac aac agc      48
Ile Ala Gly Pro Glu Trp Leu Leu Asp Arg Pro Ser Val Asn Asn Ser
  1               5                  10                  15 caa tta gtt gtt agc gtt gct ggt act gtt gag ggg acg aat caa gac      96
Gln Leu Val Val Ser Val Ala Gly Thr Val Glu Gly Thr Asn Gln Asp
             20                  25                  30 att agt ctt aaa ttt ttt gaa atc gat cta aca tca cga cct gct cat     144
Ile Ser Leu Lys Phe Phe Glu Ile Asp Leu Thr Ser Arg Pro Ala His
         35                  40                  45 gga gga aag aca gag caa ggc tta agt cca aaa tca aaa cca ttt gct     192
Gly Gly Lys Thr Glu Gln Gly Leu Ser Pro Lys Ser Lys Pro Phe Ala
 50                  55                  60 act gat agt ggc gcg atg tca cat aaa ctt gag aaa gct gac tta cta     240
Thr Asp Ser Gly Ala Met Ser His Lys Leu Glu Lys Ala Asp Leu Leu
 65                  70                  75                  80 aag gct att caa gaa caa ttg atc gct aac gtc cac agt aac gac gac     288
Lys Ala Ile Gln Glu Gln Leu Ile Ala Asn Val His Ser Asn Asp Asp
                 85                  90                  95 tac ttt gag gtc att gat ttt gca agc gat gca acc att act gat cga     336
Tyr Phe Glu Val Ile Asp Phe Ala Ser Asp Ala Thr Ile Thr Asp Arg
            100                 105                 110 aac ggc aag gtc tac ttt gct gac aaa gat ggt tcg gta acc ttg ccg     384
Asn Gly Lys Val Tyr Phe Ala Asp Lys Asp Gly Ser Val Thr Leu Pro
        115                 120                 125 acc caa cct gtc caa gaa ttt ttg cta agc gga cat gtg cgc gtt aga     432
Thr Gln Pro Val Gln Glu Phe Leu Leu Ser Gly His Val Arg Val Arg
    130                 135                 140 cca tat aaa gaa aaa cca ata caa aac caa gcg aaa tct gtt gat gtg     480
Pro Tyr Lys Glu Lys Pro Ile Gln Asn Gln Ala Lys Ser Val Asp Val
145                 150                 155                 160 gaa tat act gta cag ttt act ccc tta aac cct gat gac gat ttc aga     528
Glu Tyr Thr Val Gln Phe Thr Pro Leu Asn Pro Asp Asp Asp Phe Arg
                165                 170                 175 cca ggt ctc aaa gat act aag cta ttg aaa aca cta gct atc ggt gac     576
Pro Gly Leu Lys Asp Thr Lys Leu Leu Lys Thr Leu Ala Ile Gly Asp
            180                 185                 190 acc atc aca tct caa gaa tta cta gct caa gca caa agc att tta aac     624
Thr Ile Thr Ser Gln Glu Leu Leu Ala Gln Ala Gln Ser Ile Leu Asn
        195                 200                 205 aaa aac cac cca ggc tat acg att tat gaa cgt gac tcc tca atc gtc     672
Lys Asn His Pro Gly Tyr Thr Ile Tyr Glu Arg Asp Ser Ser Ile Val
    210                 215                 220 act cat gac aat gac att ttc cgt acg att tta cca atg gat caa gag     720
Thr His Asp Asn Asp Ile Phe Arg Thr Ile Leu Pro Met Asp Gln Glu
225                 230                 235                 240 ttt act tac cgt gtt aaa aat cgg gaa caa gct tat agg atc aat aaa     768
Phe Thr Tyr Arg Val Lys Asn Arg Glu Gln Ala Tyr Arg Ile Asn Lys
                245                 250                 255
```

```
aaa tct ggt ctg aat gaa gaa ata aac aac act gac ctg atc tct gag    816
Lys Ser Gly Leu Asn Glu Glu Ile Asn Asn Thr Asp Leu Ile Ser Glu
        260                 265                 270 aaa tat tac gtc ctt aaa aaa ggg gaa aag ccg tat gat ccc ttt gat    864
Lys Tyr Tyr Val Leu Lys Lys Gly Glu Lys Pro Tyr Asp Pro Phe Asp
            275                 280                 285 cgc agt cac ttg aaa ctg ttc acc atc aaa tac gtt gat gtc gat acc    912
Arg Ser His Leu Lys Leu Phe Thr Ile Lys Tyr Val Asp Val Asp Thr
    290                 295                 300 aac gaa ttg cta aaa agt gag cag ctc tta aca gct agc gaa cgt aac    960
Asn Glu Leu Leu Lys Ser Glu Gln Leu Leu Thr Ala Ser Glu Arg Asn
305                 310                 315                 320 tta gac ttc aga gat tta tac gat cct cgt gat aag gct aaa cta ctc   1008
Leu Asp Phe Arg Asp Leu Tyr Asp Pro Arg Asp Lys Ala Lys Leu Leu
                325                 330                 335 tac aac aat ctc gat gct ttt ggt att atg gac tat acc tta act gga   1056
Tyr Asn Asn Leu Asp Ala Phe Gly Ile Met Asp Tyr Thr Leu Thr Gly
            340                 345                 350 aaa gta gag gat aat cac gat gac acc aac cgt atc ata acc gtt tat   1104
Lys Val Glu Asp Asn His Asp Asp Thr Asn Arg Ile Ile Thr Val Tyr
355                 360                 365 atg ggc aag cga ccc gaa gga gag aat gct agc tat cat tta gcc tat   1152
Met Gly Lys Arg Pro Glu Gly Glu Asn Ala Ser Tyr His Leu Ala Tyr
370                 375                 380 gat aaa gat cgt tat acc gaa gaa gaa cga gaa gtt tac agc tac ctg   1200
Asp Lys Asp Arg Tyr Thr Glu Glu Glu Arg Glu Val Tyr Ser Tyr Leu
385                 390                 395                 400 cgt tat aca ggg aca cct ata cct gat aac cct aac gac aaa           1242
Arg Tyr Thr Gly Thr Pro Ile Pro Asp Asn Pro Asn Asp Lys
                405                 410 taa                                                                1245

<210> SEQ ID NO 2
<211> LENGTH: 414
<212> TYPE: PRT
<213> ORGANISM: Streptococcus equisimilis

<400> SEQUENCE: 2

Ile Ala Gly Pro Glu Trp Leu Leu Asp Arg Pro Ser Val Asn Asn Ser
1               5                   10                  15

Gln Leu Val Val Ser Val Ala Gly Thr Val Glu Gly Thr Asn Gln Asp
            20                  25                  30

Ile Ser Leu Lys Phe Phe Glu Ile Asp Leu Thr Ser Arg Pro Ala His
        35                  40                  45

Gly Gly Lys Thr Glu Gln Gly Leu Ser Pro Lys Ser Lys Pro Phe Ala
    50                  55                  60

Thr Asp Ser Gly Ala Met Ser His Lys Leu Glu Lys Ala Asp Leu Leu
65                  70                  75                  80

Lys Ala Ile Gln Glu Gln Leu Ile Ala Asn Val His Ser Asn Asp Asp
                85                  90                  95

Tyr Phe Glu Val Ile Asp Phe Ala Ser Ala Thr Ile Thr Asp Arg
            100                 105                 110

Asn Gly Lys Val Tyr Phe Ala Asp Lys Asp Gly Ser Val Thr Leu Pro
        115                 120                 125

Thr Gln Pro Val Gln Glu Phe Leu Leu Ser Gly His Val Arg Val Arg
    130                 135                 140

Pro Tyr Lys Glu Lys Pro Ile Gln Asn Gln Ala Lys Ser Val Asp Val
145                 150                 155                 160
```

```
Glu Tyr Thr Val Gln Phe Thr Pro Leu Asn Pro Asp Asp Phe Arg
                165                 170                 175

Pro Gly Leu Lys Asp Thr Lys Leu Leu Lys Thr Leu Ala Ile Gly Asp
            180                 185                 190

Thr Ile Thr Ser Gln Glu Leu Leu Ala Gln Ala Gln Ser Ile Leu Asn
        195                 200                 205

Lys Asn His Pro Gly Tyr Thr Ile Tyr Glu Arg Asp Ser Ser Ile Val
    210                 215                 220

Thr His Asp Asn Asp Ile Phe Arg Thr Ile Leu Pro Met Asp Gln Glu
225                 230                 235                 240

Phe Thr Tyr Arg Val Lys Asn Arg Glu Gln Ala Tyr Arg Ile Asn Lys
                245                 250                 255

Lys Ser Gly Leu Asn Glu Glu Ile Asn Asn Thr Asp Leu Ile Ser Glu
            260                 265                 270

Lys Tyr Tyr Val Leu Lys Lys Gly Glu Lys Pro Tyr Asp Pro Phe Asp
        275                 280                 285

Arg Ser His Leu Lys Leu Phe Thr Ile Lys Tyr Val Asp Val Asp Thr
    290                 295                 300

Asn Glu Leu Leu Lys Ser Glu Gln Leu Leu Thr Ala Ser Glu Arg Asn
305                 310                 315                 320

Leu Asp Phe Arg Asp Leu Tyr Asp Pro Arg Asp Lys Ala Lys Leu Leu
                325                 330                 335

Tyr Asn Asn Leu Asp Ala Phe Gly Ile Met Asp Tyr Thr Leu Thr Gly
            340                 345                 350

Lys Val Glu Asp Asn His Asp Asp Thr Asn Arg Ile Ile Thr Val Tyr
        355                 360                 365

Met Gly Lys Arg Pro Glu Gly Glu Asn Ala Ser Tyr His Leu Ala Tyr
    370                 375                 380

Asp Lys Asp Arg Tyr Thr Glu Glu Arg Glu Val Tyr Ser Tyr Leu
385                 390                 395                 400

Arg Tyr Thr Gly Thr Pro Ile Pro Asp Asn Pro Asn Asp Lys
                405                 410

<210> SEQ ID NO 3
<211> LENGTH: 777
<212> TYPE: DNA
<213> ORGANISM: Homo sapiens
<220> FEATURE:
<221> NAME/KEY: CDS
<222> LOCATION: (1)...(777)

<400> SEQUENCE: 3 cag gct cag caa atg gtt cag ccc cag tcc ccg gtg gct gtc agt caa      48
Gln Ala Gln Gln Met Val Gln Pro Gln Ser Pro Val Ala Val Ser Gln
 1               5                  10                  15 agc aag ccc ggt tgt tat gac aat gga aaa cac tat cag ata aat caa     96
Ser Lys Pro Gly Cys Tyr Asp Asn Gly Lys His Tyr Gln Ile Asn Gln
            20                  25                  30 cag tgg gag cgg acc tac cta ggt aat gtg ttg gtt tgt act tgt tat    144
Gln Trp Glu Arg Thr Tyr Leu Gly Asn Val Leu Val Cys Thr Cys Tyr
        35                  40                  45 gga gga agc cga ggt ttt aac tgc gaa agt aaa cct gaa gct gaa gag    192
Gly Gly Ser Arg Gly Phe Asn Cys Glu Ser Lys Pro Glu Ala Glu Glu
    50                  55                  60 act tgc ttt gac aag tac act ggg aac act tac cga gtg ggt gac act    240
Thr Cys Phe Asp Lys Tyr Thr Gly Asn Thr Tyr Arg Val Gly Asp Thr
65                  70                  75                  80
```

```
tat gag cgt cct aaa gac tcc atg atc tgg gac tgt acc tgc atc ggg        288
Tyr Glu Arg Pro Lys Asp Ser Met Ile Trp Asp Cys Thr Cys Ile Gly
                85                  90                  95 gct ggg cga ggg aga ata agc tgt acc atc gca aac cgc tgc cat gaa        336
Ala Gly Arg Gly Arg Ile Ser Cys Thr Ile Ala Asn Arg Cys His Glu
            100                 105                 110 ggg ggt cag tcc tac aag att ggt gac acc tgg agg aga cca cat gag        384
Gly Gly Gln Ser Tyr Lys Ile Gly Asp Thr Trp Arg Arg Pro His Glu
        115                 120                 125 act ggt ggt tac atg tta gag tgt gtg tgt ctt ggt aat gga aaa gga        432
Thr Gly Gly Tyr Met Leu Glu Cys Val Cys Leu Gly Asn Gly Lys Gly
    130                 135                 140 gaa tgg acc tgc aag ccc ata gct gag aag tgt ttt gat cat gct gct        480
Glu Trp Thr Cys Lys Pro Ile Ala Glu Lys Cys Phe Asp His Ala Ala
145                 150                 155                 160 ggg act tcc tat gtg gtc gga gaa acg tgg gag aag ccc tac caa ggc        528
Gly Thr Ser Tyr Val Val Gly Glu Thr Trp Glu Lys Pro Tyr Gln Gly
                165                 170                 175 tgg atg atg gta gat tgt act tgc ctg gga gaa ggc agc gga cgc atc        576
Trp Met Met Val Asp Cys Thr Cys Leu Gly Glu Gly Ser Gly Arg Ile
            180                 185                 190 act tgc act tct aga aat aga tgc aac gat cag gac aca agg aca tcc        624
Thr Cys Thr Ser Arg Asn Arg Cys Asn Asp Gln Asp Thr Arg Thr Ser
        195                 200                 205 tat aga att gga gac acc tgg agc aag aag gat aat cga gga aac ctg        672
Tyr Arg Ile Gly Asp Thr Trp Ser Lys Lys Asp Asn Arg Gly Asn Leu
    210                 215                 220 ctc cag tgc atc tgc aca ggc aac ggc cga gga gag tgg aag tgt gag        720
Leu Gln Cys Ile Cys Thr Gly Asn Gly Arg Gly Glu Trp Lys Cys Glu
225                 230                 235                 240 agg cac acc tct gtg cag acc aca tcg agc gga tct ggc ccc ttc acc        768
Arg His Thr Ser Val Gln Thr Thr Ser Ser Gly Ser Gly Pro Phe Thr
                245                 250                 255 gat gtt cgt                                                            777
Asp Val Arg <210> SEQ ID NO 4
<211> LENGTH: 259
<212> TYPE: PRT
<213> ORGANISM: Homo sapiens

<400> SEQUENCE: 4

Gln Ala Gln Gln Met Val Gln Pro Gln Ser Pro Val Ala Val Ser Gln
 1               5                   10                  15

Ser Lys Pro Gly Cys Tyr Asp Asn Gly Lys His Tyr Gln Ile Asn Gln
            20                  25                  30

Gln Trp Glu Arg Thr Tyr Leu Gly Asn Val Leu Val Cys Thr Cys Tyr
        35                  40                  45

Gly Gly Ser Arg Gly Phe Asn Cys Glu Ser Lys Pro Glu Ala Glu Glu
    50                  55                  60

Thr Cys Phe Asp Lys Tyr Thr Gly Asn Thr Tyr Arg Val Gly Asp Thr
65                  70                  75                  80

Tyr Glu Arg Pro Lys Asp Ser Met Ile Trp Asp Cys Thr Cys Ile Gly
                85                  90                  95

Ala Gly Arg Gly Arg Ile Ser Cys Thr Ile Ala Asn Arg Cys His Glu
            100                 105                 110

Gly Gly Gln Ser Tyr Lys Ile Gly Asp Thr Trp Arg Arg Pro His Glu
        115                 120                 125
```

Thr Gly Gly Tyr Met Leu Glu Cys Val Cys Leu Gly Asn Gly Lys Gly
            130                 135                 140

Glu Trp Thr Cys Lys Pro Ile Ala Glu Lys Cys Phe Asp His Ala Ala
145                 150                 155                 160

Gly Thr Ser Tyr Val Val Gly Glu Thr Trp Glu Lys Pro Tyr Gln Gly
                165                 170                 175

Trp Met Met Val Asp Cys Thr Cys Leu Gly Glu Gly Ser Gly Arg Ile
            180                 185                 190

Thr Cys Thr Ser Arg Asn Arg Cys Asn Asp Gln Asp Thr Arg Thr Ser
        195                 200                 205

Tyr Arg Ile Gly Asp Thr Trp Ser Lys Lys Asp Asn Arg Gly Asn Leu
    210                 215                 220

Leu Gln Cys Ile Cys Thr Gly Asn Gly Arg Gly Glu Trp Lys Cys Glu
225                 230                 235                 240

Arg His Thr Ser Val Gln Thr Thr Ser Ser Gly Ser Gly Pro Phe Thr
                245                 250                 255

Asp Val Arg

<210> SEQ ID NO 5
<211> LENGTH: 1377
<212> TYPE: DNA
<213> ORGANISM: Streptococcus equisimilis

<400> SEQUENCE: 5
gcacccgtgg ccaggaccca acgctgcccg agatctcgat cccgcgaaat taatacgact    60
cactataggg agaccacaac ggtttccctc tagaaataat tttgtttaac tttaagaagg   120
agatatacca tgattgctgg acctgagtgg ctgctagacc gtccatctgt caacaacagc   180
caattggttg ttagcgttgc tggtactgtt gaggggacga atcaagacat tagtcttaaa   240
ttttttgaaa tcgatctaac atcacgacct gctcatggag aaagacaga gcaaggctta   300 agtccaaaat caaaccatt tgctactgat agtggcgcga tgtcacataa acttgagaaa   360
gctgacttac taaaggctat tcaagaacaa ttgatcgcta acgtccacag taacgacgac   420
tactttgagg tcattgattt tgcaagcgat gcaaccatta ctgatcgaaa cggcaaggtc   480
tactttgctg acaagatgg ttcggtaacc ttgccgaccc aacctgtcca agaattttg   540 ctaagcggac atgtgcgcgt tagaccatat aaagaaaaac caatacaaaa ccaagcgaaa   600
tctgttgatg tggaatatac tgtacagttt actcccttaa accctgatga cgatttcaga   660
ccaggtctca agatactaa gctattgaaa acactagcta tcggtgacac catcacatct   720
caagaattac tagctcaagc acaaagcatt ttaaacaaaa accacccagg ctatacgatt   780
tatgaacgtg actcctcaat cgtcactcat gacaatgaca ttttccgtac gattttacca   840
atggatcaag agtttactta ccgtgttaaa atcgggaac aagcttatag gatcaataaa   900
aaatctggtc tgaatgaaga aataaacaac actgacctga tctctgagaa atattacgtc   960
cttaaaaaag gggaaaagcc gtatgatccc tttgatcgca gtcacttgaa actgttcacc   1020
atcaaatacg ttgatgtcga taccaacgaa ttgctaaaaa gtgagcagct cttaacagct   1080
agcgaacgta acttagactt cagagattta tacgatcctc gtgataaggc taaactactc   1140
tacaacaatc tcgatgcttt tggtattatg gactatacct taactggaaa agtagaggat   1200
aatcacgatg acaccaaccg tatcataacc gtttatatgg gcaagcgacc cgaaggagag   1260
aatgctagct atcatttagc ctatgataaa gatcgttata ccgaagaaga acgagaagtt   1320

-continued

```
tacagctacc tgcgttatac agggacacct atacctgata accctaacga caaataa        1377

<210> SEQ ID NO 6
<211> LENGTH: 1327
<212> TYPE: DNA
<213> ORGANISM: Streptococcus equisimilis

<400> SEQUENCE: 6
taatacgact cactataggg agaccacaac ggtttccctc tagaaataat tttgtttaac        60
tttaagaagg agatatacca tgatagctgg tcctgaatgg ctactagatc gtccttctgt       120
aaataacagc caattggttg ttagcgttgc tggtactgtt gaggggacga atcaagacat       180
tagtcttaaa ttttttgaaa tcgatctaac atcacgacct gctcatggag gaaagacaga      240
gcaaggctta agtccaaaat caaaaccatt tgctactgat agtggcgcga tgtcacataa      300
acttgagaaa gctgacttac taaaggctat tcaagaacaa ttgatcgcta acgtccacag      360
taacgacgac tactttgagg tcattgattt tgcaagcgat gcaaccatta ctgatcgaaa      420
cggcaaggtc tactttgctg acaaagatgg ttcggtaacc ttgccgaccc aacctgtcca      480 agaattttg ctaagcggac atgtgcgcgt tagaccatat aaagaaaaac caatacaaaa       540
ccaagcgaaa tctgttgatg tggaatatac tgtacagttt actcccttaa accctgatga     600
cgatttcaga ccaggtctca agatactaa gctattgaaa acactagcta tcggtgacac       660
catcacatct caagaattac tagctcaagc acaaagcatt ttaaacaaaa accacccagg      720
ctatacgatt tatgaacgtg actcctcaat cgtcactcat gacaatgaca ttttccgtac      780
gattttacca atggatcaag agtttactta ccgtgttaaa aatcgggaac aagcttatag      840
gatcaataaa aaatctggtc tgaatgaaga aataaacaac actgacctga tctctgagaa      900
atattacgtc cttaaaaag gggaaaagcc gtatgatccc tttgatcgca gtcacttgaa       960
actgttcacc atcaaatacg ttgatgtcga taccaacgaa ttgctaaaaa gtgagcagct     1020
cttaacagct agcgaacgta acttagactt cagagattta tacgatcctc gtgataaggc     1080
taaactactc tacaacaatc tcgatgcttt tggtattatg gactatacct taactggaaa     1140
agtagaggat aatcacgatg acaccaaccg tatcataacc gtttatatgg gcaagcgacc     1200
cgaaggagag aatgctagct atcatttagc ctatgataaa gatcgttata ccgaagaaga    1260
acgagaagtt tacagctacc tgcgttatac agggacacct atacctgata accctaacga    1320
caaataa                                                               1327

<210> SEQ ID NO 7
<211> LENGTH: 52
<212> TYPE: DNA
<213> ORGANISM: Artificial Sequence
<220> FEATURE:
<223> OTHER INFORMATION: Chimeric gene
<220> FEATURE:
<221> NAME/KEY: CDS
<222> LOCATION: (2)...(49)

<400> SEQUENCE: 7 g aat gct agc tac cat tta gct ggt ggt ggc cag gcg caa cag att gta   49
  Asn Ala Ser Tyr His Leu Ala Gly Gly Gly Gln Ala Gln Gln Ile Val
  1               5                  10                  15 ccc                                                                   52

<210> SEQ ID NO 8
<211> LENGTH: 16
<212> TYPE: PRT
```

<210> SEQ ID NO 8
<211> LENGTH: 16
<212> TYPE: PRT
<213> ORGANISM: Artificial Sequence
<220> FEATURE:
<223> OTHER INFORMATION: Chimeric peptide

<400> SEQUENCE: 8

Asn Ala Ser Tyr His Leu Ala Gly Gly Gly Gln Ala Gln Gln Ile Val
1               5                   10                  15

<210> SEQ ID NO 9
<211> LENGTH: 1541
<212> TYPE: DNA
<213> ORGANISM: Artificial Sequence
<220> FEATURE:
<223> OTHER INFORMATION: Hybrid cassette

<400> SEQUENCE: 9

| | | | | | | |
|---|---|---|---|---|---|---|
| tttgtttaac | tttaagaagg | agatatacca | tgatagctgg | tcctgaatgg | ctactagatc | 60 |
| gtccttctgt | aaataacagc | caattggttg | ttagcgttgc | tggtactgtt | gaggggacga | 120 |
| atcaagacat | tagtcttaaa | ttttttgaaa | tcgatctaac | atcacgacct | gctcatggag | 180 |
| gaaagacaga | gcaaggctta | agtccaaaat | caaaaccatt | tgctactgat | agtggcgcga | 240 |
| tgtcacataa | acttgagaaa | gctgacttac | taaaggctat | tcaagaacaa | ttgatcgcta | 300 |
| acgtccacag | taacgacgac | tactttgagg | tcattgattt | tgcaagcgat | gcaaccatta | 360 |
| ctgatcgaaa | cggcaaggtc | tactttgctg | acaaagatgg | ttcggtaacc | ttgccgaccc | 420 |
| aacctgtcca | agaattttg | ctaagcggac | atgtgcgcgt | tagaccatat | aaagaaaaac | 480 |
| caatacaaaa | ccaagcgaaa | tctgttgatg | tggaatatac | tgtacagttt | actcccttaa | 540 |
| accctgatga | cgatttcaga | ccaggtctca | aagatactaa | gctattgaaa | cactagcta | 600 |
| tcggtgacac | catcacatct | caagaattac | tagctcaagc | acaaagcatt | ttaaacaaaa | 660 |
| accacccagg | ctatacgatt | tatgaacgtg | actcctcaat | cgtcactcat | gacaatgaca | 720 |
| ttttccgtac | gattttacca | atggatcaag | agtttactta | ccgtgttaaa | aatcgggaac | 780 |
| aagcttatag | gatcaataaa | aaatctggtc | tgaatgaaga | aataaacaac | actgacctga | 840 |
| tctctgagaa | atattacgtc | cttaaaaaag | gggaaaagcc | gtatgatccc | tttgatcgca | 900 |
| gtcacttgaa | actgttcacc | atcaaatacg | ttgatgtcga | taccaacgaa | ttgctaaaaa | 960 |
| gtgagcagct | cttaacagct | agcgaacgta | acttagactt | cagagattta | tacgatcctc | 1020 |
| gtgataaggc | taaactactc | tacaacaatc | tcgatgcttt | tggtattatg | gactatacct | 1080 |
| taactggaaa | agtagaggat | aatcacgatg | acaccaaccg | tatcataacc | gtttatatgg | 1140 |
| gcaagcgacc | cgaaggagag | aatgctagct | accatttagc | tggtggtggc | caggcgcaac | 1200 |
| agattgtacc | catagctgag | aagtgttttg | atcatgctgc | tgggacttcc | tatgtggtcg | 1260 |
| gagaaacgtg | ggagaagccc | taccaaggct | ggatgatggt | agattgtact | tgcctgggag | 1320 |
| aaggcagcgg | acgcatcact | tgcacttcta | gaaatagatg | caacgatcag | gacacaagga | 1380 |
| catcctatag | aattggagac | acctggagca | agaaggataa | tcgaggaaac | ctgctccagt | 1440 |
| gcatctgcac | aggcaacggc | cgaggagagt | ggaagtgtga | gaggcacacc | tctgtgcaga | 1500 |
| ccacatcgag | cggatctggc | cccttcaccg | atgttcgtta | g | | 1541 |

<210> SEQ ID NO 10
<211> LENGTH: 1661
<212> TYPE: DNA
<213> ORGANISM: Artificial Sequence
<220> FEATURE:
<223> OTHER INFORMATION: Hybrid cassette

```
<400> SEQUENCE: 10 gcaacccgc cagcctagcc gggtcctcaa cgacaggagc acgatcatgc gcacccgtgg      60
ccaggaccca acgctgcccg agatctcgat cccgcgaaat taatacgact cactataggg    120
agaccacaac ggtttccctc tagaaataat tttgtttaac tttaagaagg agatatacca    180
tgattgctgg acctgagtgg ctgctagacc gtccatctgt caacaacagc caattggttg    240
ttagcgttgc tggtactgtt gaggggacga atcaagacta tagtcttaaa ttttttgaaa    300
tcgatctaac atcacgacct gctcatggag gaaagacaga gcaaggctta agtccaaaat    360
caaaaccatt tgctactgat agtggcgcga tgtcacataa acttgagaaa gctgacttac    420
taaaggctat tcaagaacaa ttgatcgcta acgtccacag taacgacgac tactttgagg    480
tcattgattt tgcaagcgat gcaaccatta ctgatcgaaa cggcaaggtc tactttgctg    540
acaaagatgg ttcggtaacc ttgccgaccc aacctgtcca agaattttg ctaagcggac     600 atgtgcgcgt tagaccatat aaagaaaaac caatacaaaa ccaagcgaaa tctgttgatg    660
tggaatatac tgtacagttt actccttaa accctgatga cgatttcaga ccaggtctca     720
aagatactaa gctattgaaa acactagcta tcggtgacac catcacatct caagaattac    780
tagctcaagc acaaagcatt ttaaacaaaa accacccagg ctatacgatt tatgaacgtg    840
actcctcaat cgtcactcat gacaatgaca ttttccgtac gattttacca atggatcaag    900
agtttactta ccgtgttaaa atcgggaac aagcttatag gatcaataaa aaatctggtc      960
tgaatgaaga aataaacaac actgacctga tctctgagaa atattacgtc cttaaaaaag    1020
gggaaaagcc gtatgatccc tttgatcgca gtcacttgaa actgttcacc atcaaatacg    1080
ttgatgtcga taccaacgaa ttgctaaaaa gtgagcagct cttaacagct agcgaacgta    1140
acttagactt cagagattta tacgatcctc gtgataaggc taaactactc tacaacaatc    1200
tcgatgcttt tggtattatg gactatacct taactggaaa agtagaggat aatcacgatg    1260
acaccaaccg tatcataacc gtttatatgg gcaagcgacc cgaaggagag aatgctagct    1320
atcatttagc cggtggtggt caggcgcagc aaatggttca gccccagtcc ccggtggctg    1380
tcagtcaaag caagcccggt tgttatgaca atggaaaaca ctatcagata aatcaacagt    1440
gggagcggac ctacctaggt aatgtgttgg tttgtacttg ttatggagga agccgaggtt    1500
ttaactgcga aagtaaacct gaagctgaag agacttgctt tgacaagtac actgggaaca    1560
cttaccgagt gggtgacact tatgagcgtc ctaaagactc catgatctgg gactgtacct    1620
gcatcggggc tgggcgaggg agaataagct gtaccatcta a                        1661

<210> SEQ ID NO 11
<211> LENGTH: 1782
<212> TYPE: DNA
<213> ORGANISM: Artificial Sequence
<220> FEATURE:
<223> OTHER INFORMATION: Hybrid cassette

<400> SEQUENCE: 11
tcgcttcacg ttcgctcgcg tatcggtgat tcattctgct aaccagtaag gcaacccgc      60 cagcctagcc gggtcctcaa cgacaggagc acgatcatgc gcacccgtgg ccaggaccca    120
acgctgcccg agatctcgat cccgcgaaat taatacgact cactataggg agaccacaac    180
ggtttccctc tagaaataat tttgtttaac tttaagaagg agatatacca tggtgcaagc    240
acaacagatt gtacccatag ctgagaagtg ttttgatcat gctgctggga cttcctatgt    300
ggtcggagaa acgtgggaga aggcagcgga cgcatcactt gcacttctag aaatagatgc    360
```

```
aacgatcagg acacaaggac atcctataga attggagaca cctggagcaa gaaggataat    420
cgaggaaacc tgctccagtg catctgcaca ggcaacggcc gaggagagtg gaagtgtgag    480
aggcacacct ctgtgcagac cacatcgagc ggatctggcc ccttcaccga tgttcgtatt    540
gctggacctg agtggctgct agaccgtcca tctgtcaaca acagccaatt ggttgttagc    600
gttgctggta ctgttgaggg gacgaatcaa gacattagtc ttaaattttt tgaaatcgat    660
ctaacatcac gacctgctca tggaggaaag acagagcaag cttaagtccc aaaatcaaaa    720
ccatttgcta ctgatagtgg cgcgatgtca cataaacttg agaaagctga cttactaaag    780
gctattcaag aacaattgat cgctaacgtc cacagtaacg acgactactt tgaggtcatt    840
gattttgcaa gcgatgcaac cattactgat cgaaacggca aggtctactt tgctgacaaa    900
gatggttcgg taaccttgcc gacccaacct gtccaagaat ttttgctaag cggacatgtg    960
cgcgttagac catataaaga aaaccaata caaaaccaag cgaaatctgt tgatgtggaa   1020
tatactgtac agtttactcc cttaaaccct gatgacgatt tcagaccagg tctcaaagat   1080
actaagctat tgaaaacact agctatcggt gacaccatca catctcaaga attactagct   1140
caagcacaaa gcattttaaa caaaaaccac ccaggctata cgatttatga acgtgactcc   1200
tcaatcgtca ctcatgacaa tgacattttt cgtacgattt taccaatgga tcaagagttt   1260
acttaccgtg ttaaaaatcg ggaacaagct tataggatca ataaaaaatc tggtctgaat   1320
gaagaaataa acaacactga cctgatctct gagaaatatt acgtccttaa aaaggggaa    1380 aagccgtatg atccctttga tcgcagtcac ttgaaactgt tcaccatcaa atacgttgat   1440
gtcgatacca acgaattgct aaaaagtgag cagctcttaa cagctagcga acgtaactta   1500
gacttcagag atttatacga tcctcgtgat aaggctaaac tactctacaa caatctcgat   1560
gcttttggta ttatggacta taccttaact ggaaaagtag aggataatca cgatgacacc   1620
aaccgtatca taaccgttta tatgggcaag cgacccgaag gagagaatgc tagctatcat   1680
ttagcctatg ataaagatcg ttataccgaa gaagaacgag aagtttacag ctacctgcgt   1740
tatacaggga cacctatacc tgataaccct aacgacaaat aa                      1782

<210> SEQ ID NO 12
<211> LENGTH: 2096
<212> TYPE: DNA
<213> ORGANISM: Artificial Sequence
<220> FEATURE:
<223> OTHER INFORMATION: Hybrid cassette

<400> SEQUENCE: 12
cgaagaccat tcatgttgtt gctcaggtcg cagacgtttt gcagcagcag tcgcttcacg     60
ttcgctcgcg tatcggtgat tcattctgct aaccagtaag gcaaccccgc cagcctagcc    120
gggtcctcaa cgacaggagc acgatcatgc gcacccgtgg ccaggaccca acgctgcccg    180
agatctcgat cccgcgaaat taatacgact cactataggg agaccacaac ggtttccctc    240
tagaaataat tttgtttaac tttaagaagg agatatacca tggtgcaagc acaacagatt    300
gtacccatag ctgagaagtg ttttgatcat gctgctggga cttcctatgt ggtcggagaa    360
acgtgggaga aggcagcgga cgcatcactt gcacttctag aaatagatgc aacgatcagg    420
acacaaggac atcctataga attggagaca cctggagcaa gaaggataat cgaggaaacc    480
tgctccagtg catctgcaca ggcaacggcc gaggagagtg gaagtgtgag aggcacacct    540
ctgtgcagac cacatcgagc ggatctggcc ccttcaccga tgttcgtatt gctggacctg    600
```

-continued

```
agtggctgct agaccgtcca tctgtcaaca acagccaatt ggttgttagc gttgctggta    660
ctgttgaggg gacgaatcaa gacattagtc ttaaattttt tgaaatcgat ctaacatcac    720
gacctgctca tggaggaaag acagagcaag gcttaagtcc aaaatcaaaa ccatttgcta    780
ctgatagtgg cgcgatgtca cataaacttg agaaagctga cttactaaag gctattcaag    840
aacaattgat cgctaacgtc cacagtaacg acgactactt tgaggtcatt gattttgcaa    900
gcgatgcaac cattactgat cgaaacggca aggtctactt tgctgacaaa gatggttcgg    960
taaccttgcc gacccaacct gtccaagaat ttttgctaag cggacatgtg cgcgttagac   1020
catataaaga aaaaccaata caaaaccaag cgaaatctgt tgatgtggaa tatactgtac   1080
agtttactcc cttaaaccct gatgacgatt tcagaccagg tctcaaagat actaagctat   1140
tgaaaacact agctatcggt gacaccatca catctcaaga attactagct caagcacaaa   1200
gcattttaaa caaaaccac ccaggctata cgatttatga acgtgactcc tcaatcgtca   1260
ctcatgacaa tgcatttttc cgtacgattt taccaatgga tcaagagttt acttaccgtg   1320
ttaaaaatcg ggaacaagct tataggatca ataaaaaatc tggtctgaat gaagaaataa   1380
acaacactga cctgatctct gagaaatatt acgtccttaa aaagggggaa aagccgtatg   1440 atcccttga tcgcagtcac ttgaaactgt tcaccatcaa atacgttgat gtcgatacca   1500
acgaattgct aaaagtgag cagctcttaa cagctagcga acgtaactta gacttcagag   1560
atttatacga tcctcgtgat aaggctaaac tactctacaa caatctcgat gcttttggta   1620
ttatggacta taccttaact ggaaaagtag aggataatca cgatgacacc aaccgtatca   1680
taaccgttta tatgggcaag cgacccgaag gagagaatgc tagctaccat ttagctggtg   1740
gtggccaggc gcaacagatt gtacccatag ctgagaagtg ttttgatcat gctgctggga   1800
cttcctatgt ggtcggagaa acgtgggaga agccctacca aggctggatg atggtagatt   1860
gtacttgcct gggagaaggc agcggacgca tcacttgcac ttctagaaat agatgcaacg   1920
atcaggacac aaggacatcc tatagaattg gagacacctg gagcaagaag gataatcgag   1980
gaaacctgct ccagtgcatc tgcacaggca acggccgagg agagtggaag tgtgagaggc   2040
acacctctgt gcagaccaca tcgagcggat ctggcccctt caccgatgtt cgttag        2096
```

<210> SEQ ID NO 13
<211> LENGTH: 53
<212> TYPE: DNA
<213> ORGANISM: Artificial Sequence
<220> FEATURE:
<223> OTHER INFORMATION: Synthetically generated primer

<400> SEQUENCE: 13

```
catgatagct ggtcctgaat ggctactaga tcgtccttct gtaaataaca gcc            53
```

<210> SEQ ID NO 14
<211> LENGTH: 53
<212> TYPE: DNA
<213> ORGANISM: Artificial Sequence
<220> FEATURE:
<223> OTHER INFORMATION: Synthetically generated primer

<400> SEQUENCE: 14

```
aattggctgt tatttacaga aggacgatct agtagccatt caggaccagc tat            53
```

<210> SEQ ID NO 15
<211> LENGTH: 25
<212> TYPE: DNA
<213> ORGANISM: Artificial Sequence
<220> FEATURE:
<223> OTHER INFORMATION: Synthetically generated primer

<400> SEQUENCE: 15
cagccaattg gttgttagcg ttgct     25

<210> SEQ ID NO 16
<211> LENGTH: 47
<212> TYPE: DNA
<213> ORGANISM: Artificial Sequence
<220> FEATURE:
<223> OTHER INFORMATION: Synthetically generated primer

<400> SEQUENCE: 16
ccggaattcg cgcaacagat tgtacccata gctgagaagt gttttga     47

<210> SEQ ID NO 17
<211> LENGTH: 43
<212> TYPE: DNA
<213> ORGANISM: Artificial Sequence
<220> FEATURE:
<223> OTHER INFORMATION: Synthetically generated primer

<400> SEQUENCE: 17
ggccttaaga gcgctctaac gaacatcggt gaagggcgt cta     43

<210> SEQ ID NO 18
<211> LENGTH: 52
<212> TYPE: DNA
<213> ORGANISM: Artificial Sequence
<220> FEATURE:
<223> OTHER INFORMATION: Synthetically generated primer

<400> SEQUENCE: 18
gaatgctagc taccatttag ctggtggtgg ccaggcgcaa cagattgtac cc     52

<210> SEQ ID NO 19
<211> LENGTH: 59
<212> TYPE: DNA
<213> ORGANISM: Artificial Sequence
<220> FEATURE:
<223> OTHER INFORMATION: Synthetically generated primer

<400> SEQUENCE: 19
gtacggatcc gaatgctagc tatcatttag cgggtggtgg tcaggcgcag caaatggtt     59

<210> SEQ ID NO 20
<211> LENGTH: 39
<212> TYPE: DNA
<213> ORGANISM: Artificial Sequence
<220> FEATURE:
<223> OTHER INFORMATION: Synthetically generated primer

<400> SEQUENCE: 20
ggccttaaga gcgctctatt agatggtaca gcttattct     39

<210> SEQ ID NO 21
<211> LENGTH: 44
<212> TYPE: DNA
<213> ORGANISM: Artificial Sequence
<220> FEATURE:
<223> OTHER INFORMATION: Synthetically generated primer

<400> SEQUENCE: 21
ccatggtgca agcacaacag attgtaccca tagctgagaa gtgt     44

<210> SEQ ID NO 22
<211> LENGTH: 40
<212> TYPE: DNA
<213> ORGANISM: Artificial Sequence
<220> FEATURE:
<223> OTHER INFORMATION: Synthetically generated primer

<400> SEQUENCE: 22
ctcaggtcca gcaatacgaa catcggtgaa ggggccagat                    40

<210> SEQ ID NO 23
<211> LENGTH: 42
<212> TYPE: DNA
<213> ORGANISM: Artificial Sequence
<220> FEATURE:
<223> OTHER INFORMATION: Synthetically generated primer

<400> SEQUENCE: 23
ttcaccgatg ttcgtattgc tggacctgag tggctgctag ac                 42

<210> SEQ ID NO 24
<211> LENGTH: 27
<212> TYPE: DNA
<213> ORGANISM: Artificial Sequence
<220> FEATURE:
<223> OTHER INFORMATION: Synthetically generated primer

<400> SEQUENCE: 24
tggttttgat tttggactta agccttg                                  27

<210> SEQ ID NO 25
<211> LENGTH: 20
<212> TYPE: DNA
<213> ORGANISM: Artificial Sequence
<220> FEATURE:
<223> OTHER INFORMATION: Synthetically generated primer

<400> SEQUENCE: 25
attgctggac ctgagtggct                                          20

<210> SEQ ID NO 26
<211> LENGTH: 18
<212> TYPE: DNA
<213> ORGANISM: Artificial Sequence
<220> FEATURE:
<223> OTHER INFORMATION: Synthetically generated primer

<400> SEQUENCE: 26
tggttttgat tttggact                                            18

<210> SEQ ID NO 27
<211> LENGTH: 45
<212> TYPE: DNA
<213> ORGANISM: Streptococcus equisimilis

<400> SEQUENCE: 27
atgattgctg gaccttagtg gctgctagac cgtccatctg tcaac              45

<210> SEQ ID NO 28
<211> LENGTH: 43
<212> TYPE: DNA
<213> ORGANISM: Streptococcus equisimilis

```
<400> SEQUENCE: 28
atgatagctg gtctgaatgc tactagatcg tccttctgta aat                    43
```